(12) United States Patent
Rottier et al.

(10) Patent No.: US 9,796,996 B2
(45) Date of Patent: Oct. 24, 2017

(54) MEANS AND METHODS FOR DISTINGUISHING FECV AND FIPV

(75) Inventors: Petrus Josephus Marie Rottier, Utrecht (NL); Hui-wen Chang, Utrecht (NL); Herman F. Egberink, Utrecht (NL)

(73) Assignee: UNIVERSITEIT UTRECHT HOLDING B.V., Utrecht (NL)

( * ) Notice: Subject to any disclaimer, the term of this patent is extended or adjusted under 35 U.S.C. 154(b) by 193 days.

(21) Appl. No.: 13/522,863

(22) PCT Filed: Jan. 18, 2011

(86) PCT No.: PCT/NL2011/050027
§ 371 (c)(1),
(2), (4) Date: Sep. 28, 2012

(87) PCT Pub. No.: WO2011/087366
PCT Pub. Date: Jul. 21, 2011

(65) Prior Publication Data
US 2013/0071833 A1    Mar. 21, 2013

(30) Foreign Application Priority Data
Jan. 18, 2010   (EP) ..................... 10151001

(51) Int. Cl.
*C12Q 1/70* (2006.01)
*C12Q 1/04* (2006.01)
*A61K 39/00* (2006.01)

(52) U.S. Cl.
CPC ............. *C12Q 1/04* (2013.01); *C12Q 1/701* (2013.01); *A61K 39/00* (2013.01); *C12Q 2600/156* (2013.01)

(58) Field of Classification Search
None
See application file for complete search history.

(56) References Cited

U.S. PATENT DOCUMENTS 5,670,156 A * 9/1997 Olsen .................. A61K 39/215
                                                              424/204.1
6,280,974 B1 * 8/2001 Miller et al. ................. 435/69.3
(Continued)

FOREIGN PATENT DOCUMENTS

JP        7327683      12/1995
WO    WO92/08487    * 5/1992
(Continued)

OTHER PUBLICATIONS

GenBank: ACT10896.1-Spike protein of Feline Corona Virus wherein amino acid position 1049 is not a methionine: Submitted by Spiro et al. of J.Craig Venter Institute: Apr. 2009.*
(Continued)

*Primary Examiner* — Janet L Andres
*Assistant Examiner* — M. Franco Salvoza
(74) *Attorney, Agent, or Firm* — Matthew P. Fredercik; Reed Smith LLP

(57) ABSTRACT

The invention provides methods and means for distinguishing FECV and FIPV, and methods and means for determining whether FIPV is present in a sample. Further provided are primers and probes for detecting FIPV specific nucleic acid sequences encoding a spike protein, antibodies for detecting a FIPV, and an immunogenic composition and use thereof for eliciting an immune response against a feline coronavirus, preferably a FIPV.

32 Claims, 13 Drawing Sheets

(56) References Cited

U.S. PATENT DOCUMENTS

Figure 1:
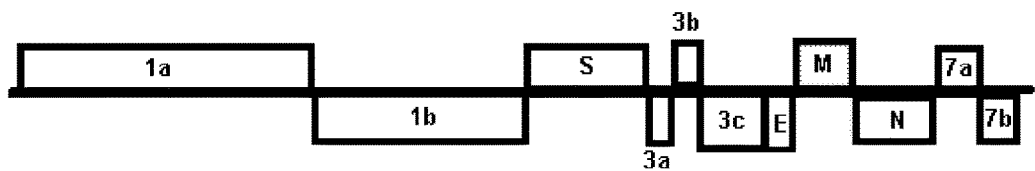

| | | | |
|---|---|---|---|
| 9,044,486 B2* | 6/2015 | Whittaker | A61K 38/55 |
| 2004/0063093 A1 | 4/2004 | Miller | |
| 2006/0051744 A1* | 3/2006 | Austin et al. | 435/5 |
| 2006/0083755 A1* | 4/2006 | Motokawa | A61K 39/215 424/204.1 |
| 2011/0190273 A1* | 8/2011 | Dewerchin | C12Q 1/485 514/218 |

FOREIGN PATENT DOCUMENTS

| | | |
|---|---|---|
| WO | 1994013836 | 6/1994 |
| WO | 1995008575 | 3/1995 |
| WO | 1997020054 | 6/1997 |
| WO | 2002066686 | 8/2002 |
| WO | WO2004096842 | * 11/2004 |
| WO | WO2005/116250 | * 12/2005 |

OTHER PUBLICATIONS

Tekes et al., "Genome Organization and Reverse Genetic Analysis if a Type I Feline Coronavirus," Journal of Virology, vol. 82, No. 4: pp. 1851-1859 (2008).*
Addie et al., "Persistence and transmission of natural type I feline coronavirus infection," Journal of General Virology, 84; 2735-2744 (2003).*
Kipar et al., "Feline Infectious Peritonitis: Still an Enigma?", Veterinary Pathology vol. 51(2): 505-526 (2014).*
Balint et al., "Recombinant feline coronaviruses as vaccine candidates confer protection in SPF but not in conventional cats," Veterinary Microbiology, 169: 154-162 (2014).*
Cornell Feline Health Center, "Feline Infectious Peritonitis," Cornell University College of Veterinary Medicine, available at http://www.vet.cornell.edu/fhc/Health_Information/brochure_ftp.cfm (2014).*
Pedersen, "An update on feline infectious peritonitis: Virology and immunopathogenesis," The Veterinary Journal 201:123-132 (2014).*
Spiro, et al., 2009, J. Craig Venter Institute, 9704 Medical Center Drive, Rockville, MD 20850, USA, spike protein [Feline coronavirus UU10] sequence, Gene Bank [online], National Center for Biotechnology Information [retreived on Jul. 30, 2014], GenBank Accession No. ACT10937.
McArdle, et al., 1995, Independent Evaluation of a Modified Live FIPV Vaccine Under Experimental Conditions (University of Liverpool Experience). Feline Practice, vol. 23, No. 3, pp. 67-71.
Barany, F. (1991) Genetic disease detection and DNA amplification using cloned thermostable ligase. Proc. Natl. Acad. Sci. USA 88: 189-193.
Baron H, Fung S, Aydin A, Bähring S, Luft FC, Schuster H. Oligonucleotide ligation assay (OLA) for the diagnosis of familial hypercholesterolemia. Nat Biotechnol. Oct. 1996; 14(10):1279-82.
Boom R, Sol CJ, Salimans MM, Jansen CL, Wertheim-van Dillen PM, van der Noordaa J. Rapid and simple method for purification of nucleic acids. J Clin Microbiol. Mar. 1990;28(3):495-503.
Brown MA, Troyer JL, Pecon-Slattery J, Roelke ME, O'Brien SJ. Genetics and pathogenesis of feline infectious peritonitis virus. Emerg Infect Dis. 2009;15(9):1445-52.
Chomczynski P, Sacchi N. Single-step method of RNA isolation by acid guanidinium thiocyanate-phenol-chloroform extraction. Anal Biochem. Apr. 1987;162(1):156-9.
Compton, J. (1991) Nucleic acid sequence-based amplification. Nature 1991, 350:91-92.
Crain PF, McCloskey JA. Applications of mass spectrometry to the characterization of oligonucleotides and nucleic acids [Review]. Curr Opin Biotechnol 1998;9:25-34.
Day IN, Spanakis E, Palamand D, Weavind GP, O'Dell SD. Microplate-array diagonal-gel electrophoresis (MADGE) and melt-MADGE: tools for molecular-genetic epidemiology. Trends Biotechnol. Jul. 1998;16(7):287-90.

Devereux J, Haeberli P, Smithies O. A comprehensive set of sequence analysis programs for the VAX. Nucleic Acids Res. Jan. 11, 1984;12(1 Pt 1):387-95.
Dye C, Siddell SG. Genomic RNA sequence of feline coronavirus strain FCoV C1Je. J Feline Med Surg. Jun. 2007;9(3):202-13.
Fan,J.B., Chen,X., Halushka,M.K., Berno,A., Huang,X., Ryder,T., Lipshutz,R.J., Lockhart,D.J. and Chakravarti,A. (2000) Parallel genotyping of human SNPs using generic high-density oligonucleotide tag arrays. Genome Res., 10, 853-860.
Fehr D, Holznagel E, Bolla S, Hauser B, Herrewegh AA, Horzinek MC, Lutz H. Placebo-controlled evaluation of a modified life virus vaccine against feline infectious peritonitis: safely and efficacy under field conditions. Vaccine. Jul. 1997;15(10):1101-9.
Fischer SG, Lerman LS. Separation of random fragments of DNA according to properties of their sequences. Proc Natl Acad Sci U S A. Aug. 1980;77(8):4420-4.
Guatelli, J.C., Whitf[iota]eld, KM., Kwoh, D.Y., Barringer, K. J., Richman, D.D., Gingeras, T.R. (1990) Isothermal, in vitro amplification of nucleic acids by a mutienzyme reaction modeled after retroviral replication. Proc. Natl. Acad. Sd. USA 87:1874-1878.
Kennedy, M., Boedeker, N., Gibbs, P., Kania, S. (2001) Deletions in the 7a ORF of feline coronavirus associated with an epidemic of feline infectious peritonitis. Vet. Microbiol. 81, 227-234.
Kwoh, D.Y., Davis, G.R., Whitefield, K.M., Chappelle, H.L., DiMichele, L. J., Gingeras, T.R. (1989) Transcription-Based Amplification System and Detection of Amplified Human Immunodeficiency Virus Type 1 with a Bead- Based Sandwich Hybridization Format. Proc. Natl Acad. Sd. USA, 86, 1173-1177.
Makino R, Yazyu H, Kishimoto Y, Sekiya T, Hayashi K. F-SSCP: fluorescence-based polymerase chain reaction-single-strand conformation polymorphism (PCR-SSCP) analysis. PCR Methods Appl. Aug. 1992;2(1):10-3.
Morlan J, Baker J, Sinicropi D. Mutation detection by real-time PCR: a simple, robust and highly selective method. PLoS One. 2009;4(2):e4584.
Pedersen NC. A review of feline infectious peritonitis virus infection: 1963-2008. Feline Med Surg. Apr. 2009;11(4):225-58.
Poland AM, Vennema H, Foley JE, Pedersen NC. Two related strains of feline infectious peritonitis virus isolated from immunocompromised cats infected with a feline enteric coronavirus. J Clin Microbiol. Dec. 1996;34(12):3180-4.
Rottier PJ, Nakamura K, Schellen P, Volders H, Haijema BJ. Acquisition of macrophage tropism during the pathogenesis of feline infectious peritonitis is determined by mutations in the feline coronavirus spike protein. J Virol. Nov. 2005;79(22):14122-30.
Sanger, F., Nicklen, S., Coulson, A.R. (1977) DNA sequencing with chain-terminating inhibitors. Proc. Natl. Acad. Sci. U.S.A. 74;5463-5467.
Vennema H, Poland A, Foley J, Pedersen NC. Feline infectious peritonitis viruses arise by mutation from endemic feline enteric coronaviruses. Virology. Mar. 30, 1998;243(1):150-7.
Walker, G.T., Fraiser, M.S., Schram, J.L., Little, M.C., Nadeau, J.G., Malinowski, D. P. (1992) Strand displacement amplification—an isothermal, in vitro DNA amplification technique Nucleic Acids Res 20:1691-1696.
Fakhrai-Rad H, Pourmand N, Ronaghi M. Pyrosequencing: an accurate detection platform for single nucleotide polymorphisms. Hum Mutat. May 2002;19(5):479-85.
Haijema, B. J., P. J. Rottier, and R. J. de Groot. 2007. Feline coronaviruses: a tale of two-faced types, p. 183-203. In V. Thiel (ed.), Coronaviruses. Molecular and cellular biology. Caister Academic Press, Norfolk, United Kingdom.
Lizardi, P.M., Guerra, C.E., Lomeli, H., Tussie-Luna, I., Kramer, F. R. (1988) Exponential amplification of recombinant RNA hybridization probes. Biotechnology 6, 1197-1202.
Motokawa K, Hohdatsu T, Hashimoto H, Koyama H. Comparison of the amino acid sequence and phylogenetic analysis of the peplomer, integral membrane and nucleocapsid proteins of feline, canine and porcine coronaviruses. Microbiol Immunol. 1996;40(6):425-33.

(56) References Cited

OTHER PUBLICATIONS

Mullis, K.B., Faloona, F.A. (1987) Specific synthesis of DNA in vitro via a polymerasecatalyzed chain reaction. Meth. Enzymol. 155:335-350.

* cited by examiner

Figure 2A

Nucleotide sequence of feline coronavirus spike gene derived from the sequence of NC_012955

```
            10         20         30         40         50         60         70         80         90        100
ATGATGTTGT TAATACTTGC GCTTCTTAGT ACCGCTCACT CTGAAGATGC GCCTCATGGT GTTACATTAC CACAATTTAA CACTTCCCAT GACAATGCCA    100
AGTTTGAACT TAATTTTTAC AATTTCTTAC AAACTTGGGA TATACCACCA AACACTGAAA CTATTCTTGG CCATATTCTA TGGCTATCTA CTGAAGGTGT    200
CAATTGTGGG TGGCATAATT TTGCTTTCCA GCAACATGAT GCCCTAAATG GTAAGTATGC CTACATAAAT AGAGTTGGCC TCGCAAAACT TGGGTATACC    300
GGGCTCACT TTGACGTACG AGAACGTAT TATGATGACG GCAGTGGGA GCAGCCTCAT GTTGCCGTTA AAATCTGCCA TTGGAAACCA GGTAACATAA    400
ACAGTTACT AATGGTTTTA CAAGACAACK TTGAGGAGAA TCAGCCTCAT GTTCTCTCAT TTTAACCGGA GGTTCTCATT GGACCACCAA GTTCTTACCA    500
TCAATTAGT GTTAATCTAG CAGATATTTTA GGTGGCACTA TTTACTAAAGT GTGGGTAGAC AACGATTGGA GTGTTGTTGA AGCTAGTATT TGGCTTCCAG    600
TGGACTGATA CATCTGTAGA TATTACATGC AATTTGTCAA CCGCACCACT TATTATGCCT ACAATAATAC GTTGTTGTTCA AGCTAGTATT TCCCATTATT    700
AAGTGAGTGC TAGCTATGGC TATTACATGG ACTGTGCTGG TTATGCTAAG AATGTCTTTG TGCCAAATGA TGGCAAAGCT TCTCTTTTAG ATTTACAGTT    800
CTGTTATCAG ATAAATCCAC TTTAAGTGCT AATGATGTCT TCTGCCCAA GGACGTGTTC TTAGTAAACA ACCTGTTCTT GTACAGTGCC TTAGGCCCGT GCCAACGTGG TCTCTTTTAG TAACTGGTTT    900
CTGCTGGTG ATAAATCCAC TTTAAGTGCT AATGATGTCT TCTGCCCCAA CGTTACGCCG AAGTTTAGT GGTTCAACCT GACACAGAGA TCACTGATTT TCAACCGCA    1000
GTCAAGTT GATGATCAGT TGTATTTTAC AATTTGAAGAT AACACAAAGG CATCCATAGC ACGCTTTATT TTGTTTTGCC AGTGTCTAGT TCACTGATTT TCAACCGCA    1100
AATCAAAGCG TCTCTCACAT CCCATTTTGA TGGATCCATT TTTGTTAATG GTTATAAATA ACTGCTTTCTA GTTCTGTTGT GGGTAGACAG TTCTTGGGTA    1200
TACTGCCACC AACTGTCCGA GAGTTGCAT TCGGCAGAGA GGTTTGGACC ATAGCTTACA CCAACTATAC AGATGTAATG TTTCAGTTTA TCACCTATCA AGAGTGTTAA    1300
CTTCCCATC AGTTCAGTAG AGAATTATGG CTTTTGGACC CTTTTGGACC ATAGCTTACA CCAACTATAC AGATGTAATG GTGGATGTTA ATGGCACTGG TATCACTAGG    1400
TTATTCTATT GCGACTCACC CCTCAATAGA ATCAAGTGTC AACAATTGAA GCATGAGCTA GTCACGTTAC CCAGATGGAT TTTATTCGC TAGCATGCTT GTTAAAAAGG    1500
ATCTACCTAA GACATTTGTA ACTATGCCAC AGTTTTATGA TTGGATGAAT TGGTTTGAAA TAGCCCAGGC GTCACGTTAC TAATGGCAGT GAATGATACT GAAAAGGGA AGGATATCAT    1600
TTTGCTAAG GTGCCGAAC TAGCCATCAT CTATAAGTAA AAGGTTTGTA CATTTTGAAA TAGCCCAGGC TAACGCAGT GTAACTAATG TTACTAGCCT GTGTGTGCA    1700
ACAAGACAAT TGGCTCTATT CTATAAGTAT AAACTTTGTG TTTTGATGTG AACCCATCTG TACTTATTCC AATTTAGTAG AGTACAAAA TTATGACTGC CCTTTTTCAC    1800
CACAACACAGTT TTCGCTACTA TTACTGTTTC TTACAAGGAG GGTGCTATGA TAACGACCAT TAACCGCAGC GCCGAAGCCG TAAGTGGTCG TTAGTTCATG ATGTTAAGTG    1900
GCCACACAG AATGCACTGA TATGGATTTC AGGGCACAGG AAAATTTAAG CATTATTAGA AATACCACAT CAGCGAAGCG CAAGATTGGT TTCAAGATAT TTCCAATTTA    2000
GTAAAAGATG TTCACTTCTT GCGTTAAGA TATGGATTTC AGGGCACAGG CTGTTTGAGT TTGTAAATCA TGCCCATGGA AATACCACAT TGCCAGCAG TGATTAATGA TACTACACGT    2100
CAGTAGTGT TGAYCTTCTT GCGTTAAGA ATAGCACTAC TCAAACTGAT CTGTTTGAGT TTGTAAATCA CACAAGTGA CACAAGATCAC CAAGCAGCAG TGATTAATGA TACTAATGA    2200
CGAGATGTG GGAGCTATAA CAGCCATCAA TCAAATCTAT CGCTTTAAGA AGTGGAATAA TGACACTTCG TGCCATGTGA AAAAGATCAC GCAGATCAC ACCAATAACA    2300
CCAACCACCT ATACTATGCC ACAATTCTAT TACATAACAA AGTGGAATAA GGTTGAAATT GTGGATCATA GTATAGGAGT CGTCTACCAT CACTTATTCT TCCTTTGCTA    2400
TTTGTAATAC TGGTGAAATT AGATATGTTA GGCGGAATAC ATTCAGATTC GTCAGACAAT AGTGAAATGC TGTCAAACCT TATCAAACCT GTTTCAACAG GCAACATATC    2500
AATACCTAAA AATTTCACTG TTGCAGTGCA ACTTCAGCTT GTGTTGAAAG TTTAACAGTA AGTGTTGTG CTTAACCCTG AGTATGTCTG CAATGGTAAC    2600
AGACATTGCC TTAACTTGTT AACACAATAC CACAGTTTAC AGCTTGCAAC TGTTGAAAAG TTTAACAGTA CTGTTGTAGG GTGCACGCCT GAATCTTTA ATGCTAAGG    2700
ATATGATTAC AGTATCAGAT AATTTGTTAC CAACTAGCAT TGGTAAGAGG TGGTAAGACG TCAGCTATTG AAGATCTATT TGCCCAATAT GCTATGGTT TCTATTTTGA    2800
CGGTTTGAGA AATTTGTTAC AAAAGTGCTC TTCTGGCACT GATGTTGCAG GTAAGGTTCA AGGCTATTTG TGCCCAATAT GCTCTGTTAC GCCGGTCTTGG CACTGTTGAC    2900
GATGACTATA AAAAGTGCTC TTCTGGCACT GATGTTGCAG TCAGCTATTG AAGATCTATT TACAAATGGCA ACCTGGTGTT GGCGTTCTTGG GTGGATGACA    3000
ATAAGATGGC CATGCACGTC GCCTCTTTAA TAGGAGGTAT GGCTATGGGC TCTATTACAT CGGCTGTAGC TGTTCCTTTT GCCATGCAAG TGCAGGCTAG    3100
```

Figure 2A continued

```
ACTTAACTAT GTCGCATTAC AAACTGATGT ACTACAGGAA AACCAGAAAA TACTTGCTAA TGCTTTTAAT AATGCCATTG GTAACATCAC ACTAGCGCTT 3300
GGAAAAGTTT CCAATGCTAT TACAACCATC TCAGATGGTT TTAATAGTAT GGCCTCAGCA TTGACTAAGA TTCAGAGTGT AGTTAATCAA CAGGTGAAG 3400
CGTTGAGTCA ACTTACCAGT CAGTTGCAGA AAAATTTCCA GGCCATTAGT AGTTCTATTG CTGAAATTTA TAATAGACTG GAAAAAGTAG AAGCTGATGC 3500
TCAAGTTGAC CGTCTCATTA CTGGTAGATC GGCAGCACTT AATGCTTATG TGTCTCAAAC TTTAACTCAG TATGCTGAAG TTAAGGCTAG TAGGCACCTG 3600
GCAATGGAGA AAGTAATGA TCTCAGTCGG ATAGGTATGG GTTCTGTGGA AATGGAACAC ACCTATTCTC ACTTGTCAAT TCTGCACCTG 3700
ATGGTTTACT TTTCTTTCAC ACAGTGTTAC TTCCTACGGA ATGGAAGAG GTGACGGCAT GGTCAGGAAT ATGTGTTAAT GACACATATG CATATGTGTT 3800
GAAAGACTTT GAATATTCTA TTTTAGCTA TAATGGCACG TATATGGTAA CTCCTCGTAA TATGTTTCAA CTAGAAAAC CTCAGATGAG TGATTTCGTG 3900
CAAATTACGA GTGTGAGGT GACTTTTCTG AACCACTACA ATACGAAATT TCAAGAGATT GTGATTGATT TTAATCAGAC CTGGAAATCT CAACAAGACT ATCGTGATA 4000
TGCTTGAACA ATATAATCCT AATTACACAA CACCTGAATT ACATCTACAG GAGCTACAGC AGTACATTGA CAACCTTGT AAAGCTAAAC CTCACTGCAG AAATAGACCA 4100
ATTAGAACAA CTTATGCTAA AGAGCAGACA ACCTTACTAA TATGCGCCAT TATGTGTGCC ATTAGTAGTA GTATTCTGCA TACCATTGT ACTGTTTTGC TGTCTGAGTA 4200
AGGGTGAAA CTTATGCTAA AGAGCAGACA ACCTTACTAA TATGCGCCAT TATGTGTGCC ATTAGTAGTA GTATTCTGCA TACCATTGT ACTGTTTTGC TGTCTGAGTA 4300
CTGGCTGTTG TGGGTGTTTT GGTTGTCTTG GAAGTTGTTG CAATTCTCTT TGTAGTAGAA GACAATTTGA AAGTTACGAA CCCATCGAAA AGTTCACAT 4400
TCATTAA                                                                                                        4407
```

Nucleotide sequence of feline coronavirus spike gene derived from the sequence of NC_012952

```
         10         20         30         40

Figure 2A continued

```
CTTCTCCATC AGTTCAGTAG AGAATTATGG CTTTTTGGACC ATAGCTTACA CCAACTATAC AGATGTAATG GTGGATGTTA ATGGCACTGG TATCACTAGT 1500
TTATTCTATT GCGACTCACC CCTCAATAGA ATCAAGTGTC AACAATTGAA GCATGAGCTA CCAGATGGAT TTTATTCTGC TAGCAGCTTT GTTAAAAAGG 1600
ATCTACCTAA GACATTTGTA ACTATGCCAC AGTTTTATGA TTGGATGAAT GTCACGTTAC ATGTCGTGTT ATGTCGTGTT GAATGATACT GAAAAGGGGA AGGATATCAT 1700
TTTGGCTAAG GCTGCCGAAC TAGCATCACT TGCTAATGTA CATTTTGAAA AAGTCCAGGC TAGCCCAGGC GTAACTAATG TTACTAGCCT GTGTGTGCAA 1800
ACAAGACAAT TGGCTCTATT CTATAAGTTAC CTATAAGTTAC ACTAGCTTAC AAGCTTTGTA TACTTATTCC AATTTAGTAG AGTTACAAAA TTATGACTGC CCTTTTCAC 1900
CACAACAGTT TAATAATTAT CTGCAGTTCG AAACTTTGTG TTTTGATGTG AACCCCATCTG TCGCAGGCTG TAAGTGGTCG CAGCTGGGTT TTAGTTCATG ATGTTAAGTG 2000
GCGCACACAG TTCGCTACTA TTACTGTTTC TTACAAGGAG GGTGCTATGA TAACGACCAT CATTATTAGA GCCGAAGGCG AATACCACCT CAAGATTAGT TTCAAGATAT TACTACACAT 2100
GTAAAAGATG AATGCACTGA TTACAATATA TATGGATTTC AGGGCACACAG CTTTAACAGA TCTAACAGCA CAAGCAGCTG TGATTAACGA 2200
CCATTAGTGG TGACCTTCTT GCCTTTAAAA ACAGTACTAC AGGTGAAATT TTCACTGTGG TGCCATGTGG CACACAATCA AGAAGATCAC GTAGGTCAAC CTCCGACACA 2300
GTAAAAACCT ATACTATGCC GGAGCTATAA TCAAACAGAT CTGTTTGAGT TTGTGAATCA CACACAATCA AGAAGATCAC CGTCTGTCAT TACATATTCT TCCTTTGCTA 2400
TTTGTAATAC TGGTGAAATT AAATATGTTA AGTCACTAA AGTGGAATAA TGACACCTTG ACTAATTGTA CGTCTGTCAT GTTCAAACCT GCAACATATC 2500
AATCCTAAG AATTTCACTG TTGCAGTTCG GGCGAATAAT ATTCAGATTC AAGTCAACTC TGTCGTTGTG GATTTGTCTA AGTATGTTTG CAATGGTAAC 2600
AGACATTGCC TTACTTTGCT AACACAATAT ACTTCAGCTT GTCAAACAAT TGAAAATGCC CTTAGTCTTG GTGCACGTCT TGAATCTTTG ATGCTTAAGG 2700
ATATGATTAC AGTATCAGAT CACAGTTTAA AGCTTGCAAC TGGTAAGAGG TGTTAACAGTA CTGTTGTAGG CTTGGTGGTT TCTATTTTGA 2800
CGGTTTGAGA GATTTGTTAC CACCTAGCAT TGGTAAGAGG TCTTATTG TCTATTACAT CAGCTGTCGC TAATGTTTT ACCTGGCGTC CACTGTTGAT 2900
GATGATTATA AAAAGTGCTC AGCTGGTACA GATGTTGCAG AACCAGAAAA AACCAGAAAA TACTTGCTAA CGTCTGTCGC AATGCCATTG GCTATGCAAG GTAAATTCGG ACAGCCTAG 3000
ATAAGATGGC CATGGAACT AAACTGATGT ACTACAGGAA TCAACCATTAT GGCCTCAGCA TTGACTAAGA TTGAACCATTG GTAACATTAC ACTAGCGTT 3100
ACTTAACTAT GTCGCATTAC TACAACCATA CAGTTGCAGA AAAATTTCCA GGCCATTAGT AGTTCTATTG CTGAAATTA GAAAAAGTAG AAGCTGATGC 3200
GGAAAAGTTT CCAATGAGT ACTTACCAGT CAGTTGCAGA AAAATTTCCA GGCCATTAGT AATGCTTATG TCTCTCAAAC TTTAACTCAG TAAGGCTAG TAGGCAACTG 3400
CGTTGAGTCA CGTTCATTA CTGGTAGATT ATAGGTATGG GTTCTGTGGA GTTCTGTGGA GTTCTGTGGA AATGGAACAC ACTTGTCAAT TCTGCACCTG 3500
GCAATGGAGA AAGTTAATGA GTGTGTAAA TCTCAGTCGG TTCCTACGGA ATGGAAGAG GTGCAGGAAT ATGTGTTAAT GACACATATG CATATGTGTT 3600
ATGGTTACT TTCTTGCAC ACAGTGTAC TTTTAGCTA TAATGGTACG TATATGGTAC CTCCTCGTAA TATGTTTCAA CTCACAGAAC CTCAGAGAG CATATGTGTT 3700
GAAAGACTTT GAATATTCTA TTTTAGCTA AACACTACAT ATACGACACT AGATTTACAG GTGATTGATT TATGTTTCAA GTGATTGATT TATGTTTCAA CTCAGAGAC CTCAGAGAG CATATGTGTT 3800
CAAATTACGA GATGTGAAGT GACTTTCTG AACACTACAT ATACGACACT AGATTTACAG AGCTTACAG AGCTTACAGC GAGCTACAGC TCAACCAGAA CAATCTTAAT TAACAAGACT ATGCTGATA 3900
TGCTTGAGCA ATATAATCCT AATTACACAA ACCTCACCAC TATAGCACGT GAGCTACAGC AGTACATTGA CAATCTTAAT AAGACGCTAG TTGACCTCGA AATAGACCA 4000
ATTAGAACAG CGAGCTGACA CTTATGTAAA ATGGCCTTGG TATGTGTGGC TACTGATCGG ATTAGTAGTA GTATTCTGCA ACCATTGTT ACTGTTTGC TGTCTGAGTA 4100
AGGATTGAAA CTTATGTAAA TGGGTGTTT GAAGTTGTG CAATTCTCTT CAATTCTCTT GTATTCAGAA GACAATTTGA CCCATCGAA AGGTTCACAT 4300
CTGGCTGTTG TGGGTGTTT GAAGTTCTTG CAATTCTCTT CAATTCTCTT GTGATGATT GACAATTTGA AGTTACGAA CCCATCGAA AGGTTCACAT 4400
TCATTAA 4407
```

Figure 2B

YP_003038574

```
   1 mmllilalls tahsedaphg vtlpqfntsh dnakfelnfy nflqtwdipp ntetilggyl
  61 pycaegvncg whnfafqqhd alngkyayin sqnlgipnvh gvyfdvrery yddgvweavd
 121 rvgllixihg kshysllmvl qdnxeenqph vavkichwkp gnissyhqfs vnlgdsgqcv
 181 fnrrfsldtk ltaddfygfq wtdtsvdiyl ggtitkvwvd ndwsvveasi shywsgasyg
 241 yymqfvnrtt yyaynntggs nythlqlsec ssdycagyak nvfvpidgki pesfsfsnwf
 301 llsdkstlvq grvlskqpvl vqclrpvptw snntavvhfk ndvfcpnvta evlrfnlnfs
 361 dsdvytessi ddqlyftfed ntnasiacys sanvtdfqpa nqsvshipfg ktdhayfcfa
 421 tfsssvvgrq flgilpptvr efafgrdgsi fvngykyfsl spiksvnfsi ssvenygfwt
 481 iaytnytdvm vdvngtgitr lfycdsplnr ikcqqlkhel pdgfysasml vkkdlpktfv
 541 tmpqfydwmn vtlhvvlndt ekgkdiilak aaelaslanv hfeiaqangs vtnvtslcvq
 601 trqlalfyky tsvqglytys nlvelqnydc pfspqqfnny lqfetlcfdv npsvagckws
 661 lvhdvkwrtq fatitvsyke gamittmpka qlgfqdisnl vkdectdyni ygfqgtgiir
 721 nttsrlvagl yytsvsgdll afknsttgei ftvvpcdlta qaavindeiv gaitainqtd
 781 lfefvnhtss krsrrsapit pttytmpqfy yitkwnndts snctstitys sfaicntgei
 841 ryvnvtkvei vddsigvikp vstgnisipk nftvavqaey iqiqvkpvvv dcakyvcngn
 901 rhclnlltqy tsacqtiena lnlgarlesl mlkdmitvsd hslelatvek fnstvvgger
 961 lggfyfdglr nllptsigkr saiedllfnk vvtsglgtvd ddykkcssgt dvadlvcaqy
1021 yngimvlpgv vddnkmamyt asliggmamg sitsavavpf amqvqarlny valqtdvlqe
1081 nqkilanafn naignitlal gkvsnaitti sdgfnsmasa ltkiqsvvnq qgealsqlts
1141 qlqknfqais ssiaeiynrl ekveadaqvd rlitgrlaal nayvsqtltq yaevkasrql
1201 amekvnecvk sqsdrygfcg ngthlfslvn sapdgllffh tvllptewee vtawsgicvn
1261 dtyayvlkdf eysifsyngt ymvtprnmfq prkpqmsdfv qitscevtfl nttytkfqei
1321 vidyidinkt ivdmleqynp nyttpelhlq leifnqtkln ltaeidqleq radnltniah
1381 elqqyidnln ktlvdlewln rvetyvkwpw yvwlliglvv vfciplllfc clstgccgcf
1441 gclgsccnsl csrrqfesye piekvhih
```

YP_003038543

```
   1 mmllilalls tahsedaphg vtlpqfntsh gndkfelnfy nflqtwdipp ntetifggyl
  61 pycaegvncg whnfasqqhd alngkyayin sqnlgipnvh gvyfdvrery yddgvwdavd
 121 rvglliaihg kshysllmvl qdnveenqph vavkichwkp gnissyhqfs vnlgdsgqcv
 181 fnrrfsldtk ltadgfygfq wtdtsvdiyl ggtitkvwvd ndwsvveasi shfwsgtsyg
 241 yymqfvnrtt yyxynntlgs nythlqlsec ssdycagyak nvfvpvggki pesysfsnwf
 301 llsdkstlvq grvlskqpvl vqclrpvptw snntavvhfk ndvfcpnvta evlrfnlnfs
 361 dsdvytessi ddqlyftfed ntnasiacys sanvtdlqpa nqsvshipfg ktdyayfcfa
 421 tfsssvvgrq flgilpptvr efafgrdgsi fvngykyfsl ppiksvnfsi ssvenygfwt
 481 iaytnytdvm vdvngtgits lfycdsplnr ikcqqlkhel pdgfysasml vkkdlpktfv
 541 tmpqfydwmn vtlhvvlndt ekgkdiilak aaelaslanv hfeiaqangs vtnvtslcvq
 601 trqlalfyky tslqglytys nlvelqnydc pfspqqfnny lqfetlcfdv npsvagckws
 661 lvhdvkwrtq fatitvsyke gamittmpka qlgfqdisnl vkdectdyni ygfqgtgiir
 721 nttsrlvagl yytsisgdll afknsttgei ftvvpcdlta qaavindeiv gaitavnqtd
 781 lfefvnhtqs rrsrrstsdt vktytmpqfy yitkwnndtl tnctsvitys sfaicntgei
 841 kyvnvtkvei vddsigvikp vstgnisipk nftvavqaey iqiqvkpvvv dcakyvcngn
 901 rhcltlltqy tsacqtiena lslgarlesl mlkdmitvsd hslklatvek fnstvvgger
 961 lggfyfdglr dllppsigkr sviedllfnk vvtsglgtvd ddykkcsagt dvadlvcaqy
1021 yngimvlpgv vddnkmamyt asliggmalg sitsavavpf amqvqarlny valqtdvlqe
1081 nqkilanafn naignitlal gkvsnaitti sdgfnimasa ltkiqsvvnq qgealsqlts
1141 qlqknfqais ssiaeiynrl ekveadaqvd rlitgrlaal nayvsqtltq yaevkasrql
1201 amekvnecvk sqsdrygfcg ngthlfslvn sapdgllffh tvllptewee vtawsgicvn
```

Figure 2B continued

```
1261 dtyayvlkdf eysifsyngt ymvtprnmfq prxpqmsdfv qitrcevtfl nttyttfqei
1321 vidyidinkt iadmleqynp nyttpeldlq ieifnqtkln ltaeidqleq radnlttiar
1381 elqqyidnln ktlvdlewln rietyvkwpw yvwlliglvv vfciplllfc clstgccgcf
1441 gclgsccnsl csrrqfesye piekvhih
```

MEANS AND METHODS FOR DISTINGUISHING FECV AND FIPV

This application is the United States National Stage of International Application No. PCT/NL2011/050027, filed Jan. 18, 2011, which was published as International Publication No. WO 2011/087366, and which claims benefit of European Patent Application No. 10151001.4 filed Jan. 18, 2010 and European Patent Application No. 10151340.6 filed Jan. 21, 2010. The European Patent Application No. 10151001.4 and European Patent Application No. 10151340.6 are incorporated by reference in their entirety herewith.

The invention relates to the field of veterinary diagnosis, more specifically the invention relates to the field of feline coronaviruses and identification thereof.

Feline coronaviruses (FCoVs) are common pathogens of domestic and non-domestic Felidae, including but not limited to cats, lions, tigers, leopards, jaguars, lynxes, caracals, cheetahs, cougars and servals. In domestic multi-cat environments up to 90% FCoV seropositivity is reached. FCoV are closely related to canine coronavirus (CCoV) and transmissible gastroenteritis virus (TGEV) of swine. Two serotypes, I and II, exist of FCoV of which serotype I predominates, with 80-95% of FCoV infections. Type II FCoV presumably results from RNA recombination in animals doubly infected by serotype I FCoV and CCoV, during which a CCoV spike gene or part thereof is incorporated into the FCoV genome, apparently an infrequently occurring event. Feline enteric coronavirus (FECV) is the most common pathotype of FCoV, for both serotype I and serotype II. FECV is mainly confined to the intestines, spreads via the oral-fecal route, and is highly contagious. FECV infection generally occurs unapparently; sometimes, however, it causes symptoms such as mild enteritis (Haijema et al., 2007).

In the 1970's feline infectious peritonitis (FIP), a (then) rare but serious disease in cats, was reported to be caused by a feline coronavirus, which was called feline infectious peritonitis virus (FIPV). Contrary to FECV, FIPV is highly virulent. FIPV infection can be either granulomatous (dry) or effusive (wet) and is a progressive and usually fatal disease. Symptoms of FIP include failure to thrive in young cats, lameness, fluctuating fever, inappetence and weight loss resulting in death (Pedersen 2009). A dramatic dysregulation of the adaptive immune system accompanies progression of FIP as demonstrated by hypergammaglobulinemia and depletion of lymphoid and peripheral T cells (Haijema et al., 2007). Whereas FECV is confined to the gut, FIPV is able to infect—and replicate in—monocytes and macrophages causing systemic disease with multiple organs being affected.

Two prevailing theories exist about the origin of FIPV. According to the "mutation hypothesis", FIPV originates from FECV by de novo mutation in infected felines resulting in a highly virulent FIP virus. The mutation giving rise to FIPV has not been identified but has been proposed to be in the non structural 3c, 7a or 7b genes (see FIG. 1), which encode proteins with unknown function (Vennema et al., 1998, Poland et al., 1996, Kennedy et al., 2001, Pedersen 2009). Therefore it is thought that a mutation in the 3c, 7a or 7b gene or a combination of mutations in these genes alters the biological properties of the virus allowing the enteric coronavirus to infect monocytes and macrophages thereby spreading infection to the organs and causing FIP (Pedersen 2009): the transition of FECV to FIPV. The mutation hypothesis has not been formally proven.

According to another theory, two distinct strains of FECV circulate in natural populations, a virulent and an avirulent strain, and only felines infected by the virulent strain will develop FIP (Brown et al., 2009). Brown et al. (2009) isolated viral sequences from cats suffering from FIP, and from FECV infected but asymptomatic (healthy) cats. Using phylogenetic analyses they found that distinct viral sequences are present in sick cats and healthy cats. Dye and Siddell (2007) compared the viral sequences of feline coronavirus isolated from jejunum and from liver of a cat suffering from FIP. According to the mutation theory, FECV is confined to the intestines, while FIPV, which is able to infect macrophages and monocytes, is present in the liver. Yet, Dye and Siddell found 100% nucleotide identity and thus questioned the mutation hypothesis according to which the liver coronavirus is a mutated jejunum coronavirus. They suggested that in cats suffering from FIP the same virulent feline coronavirus strain was present in both liver and jejunum.

Previously, the present inventors identified a number of differences in the spike protein of tissue culture-adapted serotype II feline coronaviruses FECV 79-1683 and FIPV 79-1146 (Rottier et al., 2005). The FIPV 79-1146 contained several mutations in the C-terminal domain of the spike protein, the S2 domain. However, FECV 79-1683 and FIPV 79-1146 are not prototypical feline coronaviruses and are thus not representative for the serotype I FECV and FIPV most cats are infected with (Pedersen 2009). Firstly, the serotype II feline coronaviruses originate from RNA recombination of canine and feline coronaviruses and contain the canine coronavirus spike protein. Spike proteins of feline and canine coronaviruses have only approximately 45% amino acid sequence identity (Motokawa et al., 1996). Secondly, FECV 79-1683 and FIPV 79-1146 are tissue culture-adapted to cell lines other than macrophages. Because FIPV infects monocytes and macrophages in vivo, tropism of these laboratory strains differs from prototypical feline coronaviruses. Thirdly, FIPV 79-1146, unlike serotype I FIPV which infects monocytes and macrophages, is exceptionally virulent by every common route of infection (Pedersen 2009). Fourthly, FECV 79-1683 cannot be qualified as a true FECV as argued extensively by Pedersen in his recent review (Pedersen, 2009). Notably, FECV 79-1683 lacks most of the 7b gene, which is present in non-tissue culture-adapted strains of FECV and has a deleterious mutation in its 3c gene, indicating that it may have originated from an FIPV.

Feline coronavirus infection is generally demonstrated by the presence of antibodies in the blood. An effective treatment or vaccine for FIPV infection does not exist. Cats developing FIP die within days or weeks—in the case of effusive FIP—or months, in the case of dry or granulomatous FIP. A commercially available vaccine consisting of a temperature sensitive mutant of a FIPV strain has not convincingly proven its protective efficacy in a number of immunization studies (McArdle et al., 1995; Fehr et al., 1997). Furthermore, up to date there is no diagnostic test to discriminate between FECV and FIPV. A further complicating factor is that the clinical picture of FIP is highly variable and, as a consequence, the disease cannot easily be established unequivocally. The diagnosis is often a presumptive one, based on anamnestic, clinical and non-specific laboratory parameters. Because there is no specific diagnostic test for FIPV, it is often also not possible to discriminate between FIP and other diseases with overlapping symptoms. Both diagnostic tests for and vaccines against FIPV are highly needed due to the progressive and debilitating course of FIP.

It is an aim of the present invention to provide means and methods for distinguishing FIPV and FECV.

The present inventors found that FIPV harbours a specific alteration relative to FECV in the spike protein at amino acid position 1049 as depicted in FIG. 2B (SEQ ID NO:8 and SEQ ID NO:9).

The invention therefore provides a method for identifying feline infectious peritonitis virus (FIPV) comprising determining the identity of an amino acid of a feline coronavirus spike protein at a position corresponding to amino acid position 1049 as depicted in FIG. 2B (SEQ ID NO:8 and SEQ ID NO:9), and identifying the feline coronavirus as FIPV if the determined identity of the amino acid is not a methionine. According to this method of the invention, FECV is identified if the determined identity of the amino acid is methionine.

With identifying FIPV or FECV is meant the identification of a virulent (FIPV) or an avirulent (FECV) type feline coronavirus. Identification is carried out by determining the identity of an amino acid and/or nucleic acid sequence of said feline coronavirus.

A feline coronavirus nucleic acid sequence comprises a chain of nucleotides, preferably (c)DNA or RNA, that is part of a feline coronavirus or obtained from a feline coronavirus, either directly, or after processing, such as for example by using reverse transcriptase PCR, and/or amplification.

A feline coronavirus spike protein is a feline coronavirus membrane protein comprising an ectodomain. The spike protein is one of the four canonical structural proteins of coronavirus and is responsible for attachment to and entry of the virus into cells during infection.

FIPV from lesions of cats with pathologically confirmed FIP were compared genetically with FECV obtained from asymptomatic cats. Typical lesions of FIP were (pyo)granulomatous lesions presented in different internal organs mainly in spleen, liver, lung, kidney, or mesenteric lymph node. Due to the high mutation rates of RNA viruses, numerous differences were observed between individual FECV and FIPV sequences. However, in all 47 FECV faeces or plasma isolates, the amino acid at position 1049 of the spike protein as depicted in FIG. 2B is a methionine, whereas in 52 out of 54 FIPV lesion isolates an alteration of the amino acid at position 1049 as depicted in FIG. 2B is present resulting in an amino acid at this position other than methionine. It was later found that five sequences classified as derived from healthy cats were actually derived from blood samples of cats with confirmed FIP (Q093501030_326B_4546.scf, Q093501032_327B_4546.scf, Q093501036_321S_4546.scf, Q093501038_321A_4546.scf and Q093501046_K11_019.ab1), meaning that the identity of the amino acid at a position corresponding to position 1049 as depicted in FIG. 2B was determined and demonstrated to be methionine in 42, instead of 47, samples from FECV faeces or plasma isolates from healthy cats.

The nucleic acid sequence encoding the methionine at position 1049 of the spike protein of FECV corresponds to the codon comprising nucleotide positions 3145, 3146 and/or 3147 of the gene encoding a feline coronavirus spike protein as depicted in FIG. 2A. The nucleotide sequence encoding the methionine in the FECV spike protein at position 1049 as depicted in FIG. 2A is adenine-thymine-guanine (a-t-g), which corresponds with the sequence adenine-uridine-guanine (a-u-g) in the viral genomic RNA. Any substitution of at least one nucleotide in this nucleotide codon results in an amino acid other than methionine in the spike protein of FECV at position 1049 as depicted in FIG. 2B. According to the present invention the identified nucleotide and/or amino acid sequence at nucleotide positions 3145, 3146 and/or 3147 of the gene encoding a feline coronavirus spike protein, and amino acid position 1049 respectively as depicted in FIGS. 2A and 2B is used to discriminate between FIPV and FECV. With the present invention for the first time a polymorphism of the feline coronavirus that enables distinguishing FECV and FIPV has been identified in prototypical serotype I FECV and FIPV.

The present inventors further found that a significant part of the small percentage of FIPV which do not harbour the specific alteration relative to FECV in the spike protein at amino acid position 1049 as depicted in FIG. 2B, harbours a specific alteration relative to FECV in the spike protein at amino acid position 1051 as depicted in FIG. 2B. In these cases, a serine at this position appeared to be substituted. Thus, the specific alteration at amino acid position 1051 also provides an approach to identify FIPV.

The invention therefore also provides a method for identifying feline infectious peritonitis virus (FIPV) comprising determining the identity of an amino acid of a feline coronavirus spike protein at a position corresponding to amino acid position 1051 as depicted in FIG. 2B, and identifying the feline coronavirus as FIPV if the determined identity of the amino acid is not a serine. Also provided is a method for determining whether feline infectious peritonitis virus (FIPV) is present in a sample, comprising determining whether said sample comprises a feline coronavirus, and if a feline coronavirus is present determining the identity of an amino acid in a spike protein of said feline coronavirus at a position corresponding to amino acid position 1051 as depicted in FIG. 2B, and determining that FIPV is present if said amino acid is not serine.

In a set of 97 cats with pathologically confirmed FIP, in 87 out of 97 FIPV lesion isolates an alteration of the amino acid at position 1049 as depicted in FIG. 2B is present resulting in an amino acid at this position other than methionine. In five of the ten FIPV lesion isolates in which a methionine was present at position 1049 as depicted in FIG. 2B, an alteration of the amino acid at position 1051 as depicted in FIG. 2B was present resulting in an amino acid at this position other than serine. The nucleic acid sequence encoding the serine at position 1051 of the spike protein of FECV corresponds to the codon comprising nucleotide positions 3151, 3152 and 3153 of the gene encoding a feline coronavirus spike protein as depicted in FIG. 2A. Serine is encoded by the nucleotide codons t/u-c-t/u, t/u-c-c, t/u-c-a, t/u-c-g, c-g-t/u and c-g-c. Any substitution of one or more nucleotides in this nucleotide codon resulting in a nucleotide sequence other than these codons results in an amino acid other than serine in the spike protein of FECV at position 1051 as depicted in FIG. 2B. According to the present invention the identified nucleotide and/or amino acid sequence at either nucleotide positions 3151, 3152 and/or 3153 of the gene encoding a feline coronavirus spike protein, and/or amino acid position 1051 of the Spike protein respectively, as depicted in FIGS. 2A and 2B is also used to discriminate between FIPV and FECV. In a preferred embodiment, an alteration of a serine at an amino acid position corresponding to position 1051 as depicted in FIG. 2B is the result of a replacement of the nucleobase thymine at a position corresponding to nucleotide position 3151 as depicted in FIG. 2A with the nucleobase guanine.

In one embodiment, the identity of the amino acids in a spike protein of a feline coronavirus at positions corresponding to amino acid positions 1049 and 1051 as depicted in FIG. 2B are both determined. If the identity of both these amino acids is determined, a high accuracy in distinguishing FIPV and FECV is obtained. In one embodiment, the identity of the amino acids at positions 1049 and 1051 as depicted in FIG. 2B is determined in one test. However, it is also possible to determine the identity of these amino acid sequentially. For instance, first the identity of the amino acid at a position corresponding to position 1049 as depicted in FIG. 2B is determined. If the presence of a methionine is detected at this position, subsequently the identity of the amino acid at a position corresponding to position 1051 as depicted in FIG. 2B is preferably determined. If the presence of an amino acid other than a methionine is detected at this position, determining the identity of the amino acid at a position corresponding to position 1051 as depicted in FIG. 2B can be omitted. However, the identity of the amino acid at this position may also be determined in that case.

A nucleic acid sequence of the spike gene (nucleotides 1-4407) of feline coronavirus comprising the nucleotides 20395-24801 as defined in the sequence of gene accession number NC_012955 (Feline coronavirus UM10, complete genome) and nucleotides 20382-24788 as defined in the sequence of gene accession number NC_012952 (Feline coronavirus UU8, complete genome) is presented in FIG. 2A. Nucleotides 20395-24801 of NC_012955 encode the feline coronavirus spike protein (YP_003038574). Nucleotides 20382-24788 of NC_012952 encode the feline coronavirus spike protein (YP_003038543). Thus, nucleotides 3145, 3146 and 3147 of the gene encoding the spike protein as used throughout the description and as depicted in FIG. 2A correspond to nucleotides 23539, 23540 and 23541 of the complete genome as defined in the sequence of NC_012955 and/or nucleotides 23526, 23527 and 23528 of the complete genome as defined in the sequence of NC_012952. Nucleotides 3151, 3152 and 3153 of the gene encoding the spike protein as used throughout the description and as depicted in FIG. 2A correspond to nucleotides 23545, 23546 and 23547 of the complete genome as defined in the sequence of NC_012955 and/or nucleotides 23532, 23533 and 23534 of the complete genome as defined in the sequence of NC_012952.

The amino acid sequence of a feline coronavirus spike protein referring to the amino acid numbering defined in the sequences of YP_003038574 and YP_003038543 which are partial translations of NC_012955 and NC_012952 respectively is presented in FIG. 2B. The numbering of amino acid positions as used throughout the description refers to the amino acid positions as defined in YP_003038574 and/or YP_003038543. A skilled person is able to identify the nucleotide and amino acid positions in any given feline coronavirus sequence which correspond to the nucleotide positions 3145, 3146 and/or 3147 and amino acid position 1049 and the nucleotide positions 3151, 3152 and/or 3153 and amino acid position 1051 as depicted in FIG. 2A or 2B, for instance using alignment software such as "Align 2" or "Bioconductor".

The symptoms of FIP include for instance the accumulation of ascitic fluid within the abdomen (only in effusive FIP), retarded growth, lack of appetite, fever, weight loss and diarrhea. As indicated herein above, similar symptoms are also observed with cats suffering from other diseases, making unequivocal diagnosis of FIP so far impossible. Now that a polymorphism has been identified for feline coronavirus spike protein that allows for determining the presence of FIPV in a sample it can be determined whether a feline, for instance a cat, suffers from FIP. Because currently there is no treatment for FIP, and the course of the disease is progressive and debilitating resulting inevitably in death, it can be decided to euthanize said cat when the animal has been demonstrated to carry FIPV. In addition, the cat or cattery owner can take proper measures to prevent possible spread of the infection and/or reduce predisposing conditions such as stress. However, when FIPV has been demonstrated to be absent in a cat, feline infectious peritonitis can be eliminated as a possible cause of the disease. Therefore, in that case the cat should not be euthanized but diagnostic approaches could be continued and the animal could be provided with treatment for the possible alternative disease(s) the symptoms of which resemble those of FIP. Such treatment can for instance be further symptomatic treatment or application of antibiotics to counteract a possible bacterial cause of the disease.

Further provided by the invention is therefore a method for determining whether feline infectious peritonitis virus (FIPV) is present in a sample, comprising preferably from a feline or from a substance that has been in contact with a feline, determining whether said sample comprises a feline coronavirus and, if a feline coronavirus is present, determining the identity of an amino acid in a spike protein of said feline coronavirus at a position corresponding to amino acid position 1049 and/or 1051 as depicted in FIG. 2B, and determining that FIPV is present if said amino acid at amino acid position 1049 is not methionine and/or if said amino acid at amino acid position 1051 is not serine.

A sample comprising feline enteric coronavirus, feline infectious peritonitis virus, feline coronavirus (spike) protein or feline coronavirus nucleic acid can be obtained from any feline directly or indirectly. Such a sample can for instance be obtained from any feline tissue or fluid or excretion product. Feline tissues, fluids or excretion products from which such sample is obtained include but are not limited to FIP lesions, blood, white blood cells, blood plasma, blood serum, saliva, ascites, urine, faeces, skin, muscle, lymph nodes and liver. A sample according to the invention that is obtained indirectly from a feline may comprise any material that contains feline tissue, fluid or excretion product, such as for instance soil or cat litter. In a preferred embodiment of the invention a sample is obtained from a FIP lesion, faeces, blood and/or ascites. In a more preferred embodiment a sample is obtained from white blood cells. Blood samples are relatively easy obtained from an animal, and white blood cells are easily isolated from a blood sample subsequently. The present inventors found that in 29 out 31 white blood cell samples obtained from cats in which an alteration of the amino acid at a position corresponding to amino acid position 1049 as depicted in FIG. 2B was detected in a FIP lesion sample, the alteration of said amino acid was also present in the white blood cell sample. Thus, the detection of an alteration of an amino acid is accurately detected in feline white blood cell samples.

When a feline is suspected of suffering from a feline coronavirus infection, a feline coronavirus nucleic acid encoding a spike protein, whereby the nucleic acid comprises the nucleotide positions 3145, 3146 and/or 3147 and/or the nucleotide positions 3151, 3152 and/or 3153 as depicted in FIG. 2A can be detected in a sample from said feline. A sample from said feline may comprise feline coronavirus nucleic acid, or isolated feline coronavirus nucleic acid. Optionally a feline coronavirus nucleic acid comprising nucleotide positions 3145, 3146 and/or 3147 and/or the nucleotide positions 3151, 3152 and/or 3153 of the gene encoding a feline coronavirus spike protein as depicted in FIG. 2A is amplified before detection. A sample according to the invention may further comprise feline coronavirus or feline coronavirus proteins, including but not limited to the spike protein.

According to the present invention the presence of methionine at a position corresponding to amino acid position 1049 of a feline coronavirus as depicted in FIG. 2B is indicative of FECV and the presence of any amino acid other than methionine at said position is indicative of FIPV. Thus the presence of alanine, arginine, asparagine, aspartic acid, cysteine, glutamic acid, glutamine, glycine, histidine, isoleucine, leucine, lysine, phenylalanine, proline, serine, threonine, tryptophan, tyrosine and/or valine at a position corresponding to amino acid position 1049 of a feline coronavirus as depicted in FIG. 2B is indicative of FIPV. In a preferred embodiment of the invention said amino acid other than methionine is leucine. The presence of any amino acid other than serine at a position corresponding to amino acid position 1051 of a feline coronavirus as depicted in FIG. 2B is indicative of FIPV. Thus the presence of alanine, arginine, asparagine, aspartic acid, cysteine, glutamic acid, glutamine, glycine, histidine, isoleucine, leucine, lysine, methionine, phenylalanine, proline, threonine, tryptophan, tyrosine and/or valine at a position corresponding to amino acid position 1051 of a feline coronavirus as depicted in FIG. 2B is indicative of FIPV. In a preferred embodiment of the invention said amino acid other than serine is alanine.

The presence of the nucleobase adenine (a) at a position corresponding to nucleotide position 3145 of the gene encoding a feline coronavirus spike protein as depicted in FIG. 2A, the nucleobase thymine (t) at a position corresponding to nucleotide position 3146 of the gene encoding a feline coronavirus spike protein as depicted in FIG. 2A and the nucleobase guanine (g) at the position corresponding to nucleotide position 3147 of the gene encoding a feline coronavirus spike protein as depicted in FIG. 2A is indicative of FECV and the presence of any nucleobases other than adenine (a) at a position corresponding to nucleotide position 3145 of the gene encoding a feline coronavirus spike protein as depicted in FIG. 2A, and/or any nucleobase other than thymine (t) at a position corresponding to nucleotide position 3146 of the gene encoding a feline coronavirus spike protein as depicted in FIG. 2A and/or any nucleobase other than guanine (g) at the position corresponding to nucleotide position 3147 of the gene encoding a feline coronavirus spike protein as depicted in FIG. 2A is indicative of FIPV. Thus, the presence of nucleobase thymine (t), and/or cytosine (c), and/or guanine (g) at a position corresponding to nucleotide position 3145 of the gene encoding a feline coronavirus spike protein as depicted in FIG. 2A, and/or nucleobases adenine (a), and/or cytosine (c), and/or guanine (g) at a position corresponding to nucleotide position 3146 of the gene encoding a feline coronavirus spike protein as depicted in FIG. 2A, and/or nucleobases adenine (a), and/or thymine (t), and/or cytosine (c) at a position corresponding to nucleotide position 3147 of the gene encoding a feline coronavirus spike protein as depicted in FIG. 2A is indicative of FIPV. Feline coronavirus is an RNA virus. Therefore, when a nucleotide is identified herein as thymine, a uracil is also encompassed by said term, as is known by a skilled person.

Therefore, the invention provides a method according to the invention, wherein the identity of the amino acid at position 1049 is determined by determining a nucleic acid sequence of a feline coronavirus nucleic acid encoding a spike protein, said nucleic acid comprising a nucleotide at, or corresponding to, position 3145, 3146 and/or 3147 of the gene encoding a feline coronavirus spike protein as depicted in FIG. 2A. In a preferred embodiment, a cytosine or thymine or guanine at a position corresponding to nucleotide position 3145 of the gene encoding a feline coronavirus spike protein as depicted in FIG. 2A is indicative of FIPV, and an adenine at a position corresponding to nucleotide position 3145 of the gene encoding a feline coronavirus spike protein as depicted in FIG. 2A is indicative of FECV. The invention also provides a method according to the invention, wherein the identity of the amino acid at position 1051 is determined by determining a nucleic acid sequence of a feline coronavirus nucleic acid encoding a spike protein, said nucleic acid comprising a nucleotide at, or corresponding to, position 3151, 3152 and/or 3153 of the gene encoding a feline coronavirus spike protein as depicted in FIG. 2A.

Coronaviruses are RNA viruses. Viral RNA can be isolated and processed with methods known in the art. For example, RNA samples can be freshly prepared from cells or tissues at the moment of harvesting, or they can be prepared from samples that are stored at −70° C. until processed for sample preparation. Alternatively, tissues or cell samples can be stored under conditions that preserve the quality of the RNA. Examples of these preservative conditions are fixation using e.g. formalin, RNase inhibitors such as RNAsin (Pharmingen) or RNasecure (Ambion), aqueous solutions such as RNAlater (Assuragen), Hepes-Glutamic acid buffer mediated Organic solvent Protection Effect (HOPE), and RCL2 (Alphelys), and non-aqueous solutions such as Universal Molecular Fixative (Sakura Finetek USA Inc.). RNA can for instance be isolated according to the method of Chomczynski and Sacchi (1987) or the method of Boom et al. (1990), or commercially available systems (such as RNeasy total RNA isolation kit from QIAGEN, Germany or High-Pure-RNA-Isolation-Kit® from Roche Diagnostics, Basel, Switzerland). Alternatively, or additionally, RNA is reverse transcribed into cDNA. Reverse transcriptase polymerase chain reaction (RT-PCR) is for instance performed using specific primers that hybridize to an RNA sequence of interest and a reverse transcriptase enzyme. Furthermore, RT-PCR can be performed with random primers, such as for instance random hexamers or decamers which hybridize randomly along the RNA, or oligo d(T) which hybridizes to the poly(A) tail of mRNA, and reverse transcriptase enzyme.

Amplification of nucleotides derived from feline coronavirus, either directly or after RT-PCR can be performed using any nucleic acid amplification method, such as the Polymerase Chain Reaction (PCR; Mullis and Faloona, 1987) or by using amplification reactions such as Ligase Chain Reaction (LCR; Barany, 1991), Self-Sustained Sequence Replication (3SR; Guatelli et al., 1990), Strand Displacement Amplification (SDA; Walker et al., 1992), Transcriptional Amplification System (TAS; Kwoh et al, 1989), Q-Beta Replicase (Lizardi et al., 1988), Rolling Circle Amplification (RCA; U.S. Pat. No. 5,871,921), Nucleic Acid Sequence Based Amplification (NASBA; Compton, 1991), Cleavase Fragment Length Polymorphism (U.S. Pat. No. 5,719,028), Isothermal and Chimeric Primer-initiated Amplification of Nucleic Acid (ICAN), Ramification-extension Amplification Method (RAM; U.S. Pat. Nos. 5,719,028 and 5,942,391) or other suitable methods for amplification of nucleic acids.

As used herein, the term "nucleic acid" or "nucleic acid molecule" comprises a chain of nucleotides, preferably DNA and/or RNA.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature. An amplification primer is preferably single stranded for maximum efficiency in amplification. Preferably, a primer is an oligodeoxyribonucleotide. A primer must be sufficiently long to prime the synthesis of extension products in the presence of the agent for polymerization. The exact lengths of the primers will depend on many factors, including temperature and composition (A/T en G/C content) of primer. A primer pair consists of one forward and one reverse primer as commonly used in the art of DNA amplification such as in PCR amplification.

The term "probe" refers to a single-stranded oligonucleotide sequence that will recognize and form a hydrogen-bonded duplex with a complementary sequence in a target nucleic acid sequence analyte or its cDNA derivative. To facilitate the detection of binding, a specific amplicon detection probe may comprise a label moiety such as a fluorophore, a chromophore, an enzyme or a radio-label, so as to facilitate monitoring of binding of the probes to the reaction product of the amplification reaction. Such labels are well known to those skilled in the art and include, for example, fluorescein isothiocyanate (FITC), [beta]-galactosidase, horseradish peroxidase, streptavidin, biotin, digoxigenin, <35>S, <14>C, <32>P and <125>I.

A primer or probe according to the invention comprises a nucleic acid sequence, preferably DNA and/or RNA. Said nucleic acid sequence also encompasses other kinds of nucleic acid structures such as for instance a DNA/RNA helix, peptide nucleic acid (PNA), and/or locked nucleic acid (LNA). Hence, the term "nucleic acid sequence" also encompasses a chain comprising non-natural nucleotides, modified nucleotides and/or non-nucleotide building blocks which exhibit the same function as natural nucleotides.

Hybridization is known in the art and refers to the combining of complementary, single-stranded nucleic acids, preferably under stringent conditions. The term "complementary", or "sequence complementarity" is also known in the art and refers to two nucleic acid strands that can be non-covalently connected by base-pairing. As used herein, "complementary" or "substantially complementary" means that two nucleic acid sequences have at least about 70%, preferably about 80%, more preferably 90%, and most preferably about 95%, sequence complementarity to each other. This means that primers and probes must exhibit sufficient complementarity to their template and target nucleic acid, respectively, to hybridise under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand.

The term "stringent conditions" refers to hybridization conditions that affect the stability of hybrids, e.g., temperature, salt concentration, pH, formamid concentration and the like. These conditions are empirically optimised to maximize specific binding and minimize non-specific binding of primer or probe to its target nucleic acid sequence. The term as used includes reference to conditions under which a probe or primer will hybridize to its target sequence, to a detectably greater degree than to other sequences (e.g. at least 2-fold over background). Stringent conditions are sequence dependent and will be different in different circumstances.

The term "% sequence identity" is defined herein as the percentage of residues in a candidate amino acid sequence or candidate nucleic acid sequence that is identical to the residues in a reference sequence after aligning the two sequences and introducing gaps, if necessary, to achieve the maximum percent identity. Methods and computer programs for the alignment are well known in the art. One computer program which may be used or adapted for purposes of determining whether a candidate sequence falls within this definition is "Align 2", authored by Genentech, Inc., which was filed with user documentation in the United States Copyright Office, Washington, D.C. 20559, on Dec. 10, 1991, or the UWGCG Package which provides the BEST-FIT program (Devereux et al., 1984).

A feline coronavirus nucleic acid comprising a nucleotide corresponding to nucleotide position 3145, 3146 or 3147 and/or the nucleotide positions 3151, 3152 or 3153 of the gene encoding a feline coronavirus spike protein as depicted in FIG. 2A may be amplified using primers that are capable of hybridizing to at least part of said feline coronavirus nucleic acid sequence. Said primers for instance hybridize to the feline coronavirus nucleic acid sequence encoding a spike protein between a position corresponding to nucleotide position 3055 and a position corresponding to nucleotide position 3669 of the gene encoding a feline coronavirus spike protein as depicted in FIG. 2A. Said primers preferably have a length of between 9 and 50 nucleotides, for instance 16, 17, 18, 19, 20, 21, 22, 23, 24, 25, 26, 27, 28, 29, 30 or 31 nucleotides. The nucleic acid product obtained with an amplification method using such primers preferably comprises at least 35 nucleotides, more preferably at least 40 nucleotides, even more preferably at least 50 nucleotides.

Therefore, the invention provides a method according to the invention, further comprising amplifying at least part of a feline coronavirus nucleic acid molecule comprising a region including, or corresponding to, nucleotide position 3145, 3146 and 3147 and/or the nucleotide position 3151, 3152 and 3153 of the gene encoding a feline coronavirus spike protein as depicted in FIG. 2A using at least one primer which is capable of hybridizing to at least part of said nucleic acid sequence between a position corresponding to nucleotide position 3055 and a position corresponding to nucleotide position 3669 of the gene encoding a feline coronavirus spike protein as depicted in FIG. 2A.

A preferred primer pair for use in a method according to the invention comprises a primer which has at least 70% sequence identity with the nucleic acid sequence 5'-CCCTC-GAGTCCCGCAGAAACCATACCTA-3' (SEQ ID NO:1), preferably at least 80% sequence identity with said nucleic acid sequence, more preferably at least 90% sequence identity with said nucleic acid sequence, most preferably at least 95% sequence identity with said nucleic acid sequence, and a primer which has at least 70% sequence identity with the nucleic acid sequence 5'-CAATATTACAATG-GCATAATGG-3' (SEQ ID NO:2), preferably at least 80% sequence identity with said nucleic acid sequence, more preferably at least 90% sequence identity with said nucleic acid sequence, most preferably at least 95% sequence identity with said nucleic acid sequence. Another preferred primer pair for use in a method according to the invention comprises a primer which has at least 70% sequence identity with the nucleic acid sequence 5'-GGCATAATGGTTTTAC-CTGGTG-3' (SEQ ID NO:3), preferably at least 80% sequence identity with said nucleic acid sequence, more preferably at least 90% sequence identity with said nucleic acid sequence, most preferably at least 95% sequence identity with said nucleic acid sequence, and a primer which has at least 70% sequence identity with the nucleic acid sequence 5'-TAATTAAGCCTCGCCTGCACTT-3' (SEQ ID NO:4), preferably at least 80% sequence identity with said nucleic acid sequence, more preferably at least 90% sequence identity with said nucleic acid sequence, most preferably at least 95% sequence identity with said nucleic acid sequence.

In one embodiment a primer pair according to the invention comprises a combination of a nucleic acid sequence 5'-CCCTCGAGTCCCGCAGAAACCATACCTA-3' (SEQ ID NO:1) and a nucleic acid sequence 5'-CAATATTA-CAATGGCATAATGG-3' (SEQ ID NO:2), or a combination of a nucleic acid sequence 5'-GGCATAATGGTTTTAC-CTGGTG-3' (SEQ ID NO:3) and a nucleic acid sequence 5'-TAATTAAGCCTCGCCTGCACTT-3' (SEQ ID NO:4).

In one embodiment of the invention the primer pairs indicated above are used in a nested PCR reaction. In a nested polymerase chain reaction two primer pairs are used in successive PCR reactions. The second primer pair is used to amplify a nucleic acid product or part thereof obtained in the amplification reaction using the first primer pair. Therefore, in one embodiment at least part of an amplified nucleic acid, amplified using a first primer pair, is further amplified using a second primer pair. A first primer pair according to the invention comprises, for example, a primer which has at least 70% sequence identity with the nucleic acid sequence 5'-CCCTCGAGTCCCGCAGAAACCATACCTA-3' (SEQ ID NO:1) and a primer which has at least 70% sequence identity with the nucleic acid sequence 5'-CAATATTA-CAATGGCATAATGG-3' (SEQ ID NO:2), and a second primer pair according to the invention comprises, for example, a primer which has at least 70% sequence identity with the nucleic acid sequence 5'-GGCATAATGGTTTTAC-CTGGTG-3' (SEQ ID NO:3) and a primer which has at least 70% sequence identity with the nucleic acid sequence 5'-TAATTAAGCCTCGCCTGCACTT-3' (SEQ ID NO:4).

Also provided by the invention is a use of a primer pair according to the invention, preferably for identifying feline enteric coronavirus (FECV) or feline infectious peritonitis virus (FIPV), and/or for determining the presence of FIPV or feline infectious peritonitis (FIP) in an animal suspected of suffering from a feline coronavirus infection.

The identity of a nucleotide at position 3145, 3146 and/or 3147 and/or the nucleotide at position 3151, 3152 and/or 3153 of the gene encoding a feline coronavirus spike protein can be determined by any method known in the art. These methods include, but are not limited to allele specific oligonucleotides (ASO), sequencing of a nucleic acid sequence (for example tag-array minisequencing [Fan et al., 2000] or pyrosequencing [Fakhrai-Rad et al., 2002]), allele-specific PCR with a blocking reagent (ASB-PCR, Morlan et al., 2009), oligonucleotide ligation assay (OLA, Baron et al., 1996), mass spectrometry (MS, for instance matrix-assisted laser desorption/ionization time-of-flight (MALDI-TOF) MS, Crain and McCloskey 1998), quantitative polymerase chain reaction (qPCR), electronic hybridization, fluorescent single-stranded conformation polymorphism (F-SSCP) analysis (Makino et al., 1992), denaturing high-performance liquid chromatography (DHPLC), gel electrophoresis (such as microplate array diagonal gel electrophoresis [MADGE, Day et al., 1998] and denaturing gradient gel electrophoresis [DGGE, Fischer and Lerman 1980]), and microarray analysis.

Allele Specific Oligonucleotides (ASO) are fluorophore-, chromophore-, enzyme- or radio-labelled nucleotide probes which are short and specific for particular RNA or DNA sequences. ASO for instance comprise a nucleotide mutation and only hybridize with nucleic acid sequences comprising this mutation. The nucleic acid sequence of a feline coronavirus nucleic acid sequence encoding a spike protein comprising a nucleotide at, or corresponding to, position 3145, 3146 and/or 3147 and/or nucleotide position 3151, 3152 and/or 3153 as depicted in FIG. 2A is for instance detected using a probe that is capable of specifically hybridizing to at least part of said feline coronavirus nucleic acid sequence comprising a nucleotide corresponding to nucleotide position 3145, 3146, and/or 3147 and/or nucleotide position 3151, 3152 and/or 3153 of the gene encoding a feline coronavirus spike protein as depicted in FIG. 2A. Said probe preferably has a length of between 14 and 100 nucleotides, preferably 14, 15, 16, 17, 18, 19, 20, 21, 22, or more nucleotides. Therefore, in one embodiment a feline coronavirus nucleic acid sequence comprising a nucleotide at, or corresponding to, position 3145, 3146 and 3147 and/or nucleotide position 3151, 3152 and 3153 of the gene encoding a feline coronavirus spike protein as depicted in FIG. 2A is detected using a probe with a length of at least 14 nucleotides that is capable of specifically hybridizing to at least part of said nucleic acid. In a preferred embodiment a probe is capable of specifically hybridizing to a feline coronavirus nucleic acid comprising cytosine or thymine at a position corresponding to nucleotide position 3145 of the gene encoding a feline coronavirus spike protein as depicted in FIG. 2A.

A probe used in a method according to the invention is complementary to a feline coronavirus nucleic acid sequence encoding a spike protein comprising a nucleotide corresponding to nucleotide position 3145, 3146, and 3147 and/or nucleotide position 3151, 3152 and 3153 as depicted in FIG. 2A. Because coronaviruses are RNA viruses they have relatively high rates of mutation as a skilled person will know. Therefore, the sequence of feline coronaviruses may differ in some nucleotides surrounding nucleotide position 3145, 3146, and 3147 and/or nucleotide position 3151, 3152 and 3153 of the gene encoding a feline coronavirus spike protein. A person skilled in the art knows how a probe according to the invention is modified, for instance by nucleic acid substitution, to enable said probe to hybridize to the nucleic acid sequence of a specific feline coronavirus and detect a nucleotide at, or corresponding to, position 3145, 3146, or 3147 and/or position 3151, 3152 or 3153 of the gene encoding a feline coronavirus spike protein as depicted in FIG. 2A.

A preferred probe comprising a nucleotide corresponding to nucleotide positions 3145, 3146, and 3147 as depicted in FIG. 2A for use in a method according to the invention comprises a sequence which has at least 70% sequence identity with the nucleic acid sequence 5'-CCCARRGC-CATAGG-3' (SEQ ID NO:5), wherein R is A or G, preferably at least 80% sequence identity with said nucleic acid sequence, more preferably at least 90% sequence identity with said nucleic acid sequence, most preferably at least 95% sequence identity with said nucleic acid sequence. In one embodiment the invention provides a method according to the invention, wherein said probe comprises the sequence CCCARRGCCATAGG (SEQ ID NO:5). Also provided by the invention is a use of a probe according to the invention, preferably for identifying feline enteric coronavirus (FECV) and/or feline infectious peritonitis virus (FIPV), and/or for determining the presence of feline infectious peritonitis (FIP) in an animal suspected of suffering from a feline coronavirus infection.

Feline coronavirus nucleic sequences may be determined by sequencing methods known to the skilled person, preferably directly after amplification of relevant nucleic acid. These methods comprise for instance direct double-stranded nucleotide sequencing using fluorescently labeled dideoxynucleotide terminators (Smith et al., 1986), tag-array minisequencing or pyrosequencing. In general such sequencing methods include the isolation of the viral genome nucleic acids by nucleic acid isolation procedures, and the determination of the nucleotide sequence of the isolated nucleic acid, for instance by dideoxy chain termination methods (Sanger et al., 1977) optionally preceded by reverse transcription of RNA into DNA, and/or amplification of the target nucleic acid.

In one embodiment at least part of a feline coronavirus nucleic acid sequence comprising a nucleotide corresponding to nucleotide position 3145, 3146 and/or 3147 and/or nucleotide position 3151, 3152 and 3153 of the gene encoding a feline coronavirus spike protein as depicted in FIG. 2A is sequenced.

Oligonucleotide ligation assay (OLA) is a method for the detection of known single nucleotide polymorphisms. The method is based on the ligation of two adjacent oligonucleotide probes using a DNA ligase while they are annealed to a complementary DNA target. One of the probes is for instance fluorescently labeled and allele-specific. Typically, there are two differently labeled probes, one for each allele. These two probes differ only in sequence at the last base at the 3' end, thus at the site of the polymorphism. The second probe is a common probe that is complementary to the target DNA sequence immediately downstream (3') of the site containing the polymorphism, and thus complementary to both alleles. This probe does not need to be fluorescently labeled. Allele discrimination occurs by the ability of DNA ligase to join perfectly matched probes; a 3' mismatch in the capture probe will prevent ligation. In a method of the invention, for instance an oligonucleotide ligation assay is used wherein one of the probes is specifically able to hybridize to a feline coronavirus nucleic acid sequence encoding a spike protein comprising an adenine at nucleotide position 3145 as depicted in FIG. 2A which is indicative of FECV. Thus the first nucleotide of a right probe or the last nucleotide of a left probe is a thymine. The second probe is a common probe, which is able to hybridize to both FECV and FIPV nucleic acid sequence starting next to position 3145 of the gene encoding a feline coronavirus spike protein as depicted in FIG. 2A, for example starting at position 3146 if said second probe is a right probe. In the presence of FECV, ligation of said two probes is possible, whereas in the presence of FIPV, ligation of said two probes is not possible. In one embodiment of the invention a feline coronavirus nucleic acid sequence encoding a spike protein, comprising nucleotide position 3145, 3146 and/or 3147 is determined using an oligonucleotide ligation assay (OLA).

Real time PCR technology can be used to detect one specific allele of a gene when a blocking reagent is used. This technology is called allele specific PCR with a blocking reagent (ASB-PCR, Morlan et al., 2009). During the PCR reaction a blocking agent is added to the reaction mixture to prevent amplification of one allele. One of the primers, for example the forward primer, is designed as mutant allele specific primer. The other primer is a common primer, which is able to hybridize to both alleles. A blocking agent, which is phosphorylated at the 3' end to prevent amplification, is then designed to bind specifically to the wildtype allele. During the PCR reaction the blocking agent prevents hybridization of the mutant specific primer to the wildtype allele. In the presence of only the wildtype allele no amplification product is obtained, whereas in the presence of only the mutant allele an amplification product is obtained. With ASB-PCR it is for instance possible to discriminate between a feline coronavirus nucleic acid sequence comprising an adenine at nucleotide position 3145 of the gene encoding a feline coronavirus spike protein as depicted in FIG. 2A and which is indicative of FECV, and a feline coronavirus nucleic acid sequence comprising a cytosine or thymine at said position, which is indicative of FIPV. For example, a primer set is used consisting of a common reverse primer and two FIPV nucleic acid specific primers from which the 3' end nucleotide is complementary to nucleotide position 3145 of the gene encoding a feline coronavirus spike protein as depicted in FIG. 2A. One of these FIPV specific primers has an adenine at its 3' end and the other primer has a guanine at its 3' end which enables said primers to hybridize to a feline coronavirus nucleic acid sequence encoding a spike protein containing a thymine or a cytosine at nucleotide position 3145 respectively. A blocking agent comprising a thymine at the 3' end can be used, which is able to hybridize to an adenine at nucleotide position 3145. Using said primer set, amplification will occur when FIPV nucleic acid is present whereas amplification will not occur when only FECV nucleic acid is present. In a preferred embodiment of the invention a feline coronavirus nucleic acid sequence encoding a spike protein, comprising nucleotide position 3145, 3146 and/or 3147 and/or nucleotide position 3151, 3152 and/or 3153 is determined using allele-specific PCR with a blocking reagent (ASB-PCR).

Using MALDI-TOF MS the detection of low (femtomole) quantities of DNA can be achieved. Nucleic acids ranging from 2 to 2000 nucleotides can be detected by using MALDI-TOF MS. MS can be used to analyze mixtures of different nucleic acid fragments without the use of any label because of the mass differences of the nucleobases. Thus, in most cases, separation of nucleic acid fragments is not necessary before MS measurements. Using MALDI-TOF MS it is for instance possible to determine whether a nucleotide of a feline coronavirus nucleic acid sequence encoding a spike protein at nucleotide position 3145 is an adenine, which is indicative of FECV, or a cytosine or thymine, which is indicative of FIPV. In one embodiment of the invention the mass of at least part of a feline coronavirus nucleic acid sequence, said part comprising a nucleotide corresponding to nucleotide position 3145, 3146, and/or 3147 and/or nucleotide position 3151, 3152 and/or 3153 of the gene encoding a feline coronavirus spike protein as depicted in FIG. 2A is determined. In a preferred embodiment the mass of said nucleic acid sequence is determined using matrix-assisted laser desorption/ionization time-of-flight mass spectrometry (MALDI-TOF MS).

The identity of an amino acid in a feline coronavirus amino acid sequence encoding a spike protein at amino acid position 1049 and/or amino acid position 1051 as depicted in FIG. 2B can be detected using any method known in the art. Such amino acid is for instance detected using antibodies or functional equivalents thereof, mass spectrometry or Edman degradation reactions. Optionally, a coronaviral protein can be purified with methods known in the art. For instance, coronaviral protein can be purified using gel electrophoresis or chromatography methods, such as affinity chromatography.

A functional equivalent of an antibody is defined as a compound which has at least one same property as said antibody in kind, not necessarily in amount. Said functional equivalent is capable of binding the same antigen as said antibody, albeit not necessarily to the same extent. A functional equivalent of an antibody preferably comprises a single domain antibody, a single chain antibody, a nanobody, a unibody or a single chain variable fragment (scFv). A functional equivalent of an antibody is for instance produced by altering an antibody such that at least one property—preferably an antigen-binding property—of the resulting compound is essentially the same in kind, not necessarily in amount. This is done in many ways, for instance through conservative amino acid substitution, whereby an amino acid residue is substituted by another residue with generally similar properties (size, hydrophobicity, etc), such that the overall functioning is likely not to be seriously affected.

An immunogenic part of a feline coronavirus comprising a feline coronavirus spike protein is defined as a part which has at least one property in common with a feline coronavirus comprising a feline coronavirus spike protein in kind, though not necessarily in amount. An immunogenic part of a feline coronavirus spike protein is defined as a part which has at least one same property as a feline coronavirus spike protein in kind, not necessarily in amount. Said immunogenic part, is preferably capable of eliciting an immune response against a feline coronavirus, preferably a feline infectious peritonitis virus (FIPV), in an animal.

An amino acid of a feline coronavirus spike protein amino acid sequence, corresponding to amino acid position 1049 and/or amino acid position 1051 as depicted in FIG. 2B is for instance detected using an antibody or functional equivalent that is specifically directed against an epitope of a feline coronavirus spike protein that comprises amino acid position 1049 and/or amino acid position 1051 as depicted in FIG. 2B. Said amino acid position 1049 and/or amino acid position 1051 as depicted in FIG. 2B enables discrimination between FECV and FIPV. A methionine at amino acid position 1049 is indicative of FECV, whereas any amino acid other than methionine at this position, preferably leucine, is indicative of FIPV and any amino acid other than serine at amino acid position 1051, preferably alanine, in indicative of FIPV. Therefore, the invention provides a method according to the invention, wherein an amino acid of a feline coronavirus spike protein at a position corresponding to amino acid position 1049 and/or amino acid position 1051 as depicted in FIG. 2B is detected by using an antibody or functional equivalent thereof specifically directed against an epitope of a FIPV spike protein encompassing amino acid 1049 and/or amino acid 1051. In one embodiment said epitope comprises an amino acid other than methionine at a position corresponding to amino acid position 1049 and/or said epitope comprises an amino acid other than serine at a position corresponding to amino acid position 1051 as depicted in FIG. 2B.

An antibody or functional equivalent thereof specifically directed against an epitope of a FIPV spike protein, which epitope comprises an amino acid corresponding to amino acid position 1049 and/or amino acid position 1051 as depicted in FIG. 2B can be detected with any method known in the art. For instance, said antibody or functional equivalent thereof is fluorophore-, chromophore- or enzyme-labelled, and can thus be detected with for instance fluorescence microscopy or spectrophotometry. An antibody or functional equivalent can also be detected using a second antibody which is for instance fluorophore-, chromophore- or enzyme-labelled. Such labels are well known to those skilled in the art and include, for example, fluorescein isothiocyanate (FITC), [beta]-galactosidase, horseradish peroxidase, streptavidin, biotin or digoxigenin.

Also provided by the invention is an antibody or functional equivalent specifically directed against an epitope of a FIPV spike protein, which epitope comprises an amino acid other than methionine at a position corresponding to amino acid position 1049 as depicted in FIG. 2B and a kit of parts comprising an antibody according to the invention and means for detecting said antibody.

Using MALDI-TOF MS the detection of low quantities of amino acid sequences can be achieved. MS can be used to analyze mixtures of different amino acid sequences without the use of any label because of the mass differences of the amino acid sequences. Thus, in most cases, separation of amino acid sequences is not necessary before MS measurements. Using MALDI-TOF MS it is for instance possible to discriminate between a feline coronavirus amino acid sequence comprising a methionine at amino acid position 1049 as depicted in FIG. 2B, and a feline coronavirus amino acid sequence comprising an amino acid other than methionine at amino acid position 1049 as depicted in FIG. 2B. In one embodiment of the invention the mass of at least part of a feline coronavirus amino acid sequence, said part comprising an amino acid corresponding to amino acid position 1049 as depicted in FIG. 2B is determined. In a preferred embodiment the mass of said amino acid sequence is determined using matrix-assisted laser desorption/ionization time-of-flight mass spectrometry (MALDI-TOF MS).

The development of vaccines against FIPV has been unsuccessful to date. Various approaches have failed to provide a vaccine that induces protection against FIPV. These approaches include vaccination with closely related heterologous live coronaviruses, sublethal amounts of virulent FIPV, low-virulence FIPV, and (recombinant) feline coronavirus subunits or proteins. Some of these approaches provided some protection but the results were inconsistent. Occasionally, vaccination even resulted in enhanced disease progression and death. The only currently available vaccine is based on a temperature-sensitive strain of FIPV of which the efficacy is questionable (McArdle et al., 1995; Fehr et al., 1997).

Now that a polymorphism in the spike protein of feline coronavirus has been identified that allows discrimination between FECV and FIPV it is possible to develop immunogenic compositions comprising feline coronaviruses comprising the identified nucleic acid or amino acid indicative for FECV. Using an immunogenic composition comprising a feline coronavirus with a nucleic acid or amino acid representative of a FECV there is no risk of disease and/or death because said immunogenic composition does not comprise the virulent FIPV or part thereof. It is now also possible to develop an immunogenic composition comprising feline coronavirus spike protein comprising the identified amino acid indicative for FIPV. Using an immunogenic composition comprising FIPV spike protein or immunogenic part thereof a better immune response against FIPV can be elicited, without the risk of enhanced disease progression and/or death because only isolated viral proteins are used.

Therefore in one embodiment the invention provides an immunogenic composition comprising a feline coronavirus spike protein or immunogenic part thereof comprising an amino acid other than methionine at a position corresponding to amino acid position 1049, and/or an amino acid other than serine at a position corresponding to amino acid position 1051 as depicted in FIG. 2B, or a spike protein encoding feline coronavirus nucleic acid, comprising a cytosine or thymine at a position corresponding to nucleotide position 3145, and/or a guanine at a position corresponding to nucleotide position 3151 as depicted in FIG. 2A, or a feline coronavirus comprising a nucleic acid comprising an adenine at a position corresponding to nucleotide position 3145, and/or a thymine at a position corresponding to position 3151 of the gene encoding a feline coronavirus spike protein as depicted in FIG. 2A, or a feline coronavirus comprising a feline coronavirus spike protein or immunogenic part thereof comprising a methionine at a position corresponding to amino acid position 1049, and/or a serine at a position corresponding to amino acid position 1051 as depicted in FIG. 2B, or any combination thereof. In a preferred embodiment an immunogenic composition according to the invention is used as a vaccine.

Further provided is a feline coronavirus spike protein or immunogenic part thereof comprising an amino acid other than methionine at a position corresponding to amino acid position 1049, and/or an amino acid other than serine at a position corresponding to amino acid position 1051 as depicted in FIG. 2B, or a spike protein encoding feline coronavirus nucleic acid comprising a cytosine or thymine at a position corresponding to nucleotide position 3145, and/or a guanine at a position corresponding to nucleotide position 3151 as depicted in FIG. 2A, or a feline coronavirus comprising a nucleic acid comprising an adenine at a position corresponding to nucleotide position 3145, and/or a thymine at a position corresponding to position 3151 of the gene encoding a feline coronavirus spike protein as depicted in FIG. 2A, or a feline coronavirus comprising a feline coronavirus spike protein or immunogenic part thereof comprising a methionine at a position corresponding to amino acid position 1049, and/or a serine at a position corresponding to amino acid position 1051 as depicted in FIG. 2B, or any combination thereof, for eliciting an immune response against a feline coronavirus, preferably a feline infectious peritonitis virus (FIPV), in a feline.

One embodiment provides a use of a feline coronavirus spike protein or immunogenic part thereof comprising an amino acid other than methionine at a position corresponding to amino acid position 1049, and/or an amino acid other than serine at a position corresponding to amino acid position 1051 as depicted in FIG. 2B, or a spike protein encoding feline coronavirus nucleic acid comprising a cytosine or thymine at a position corresponding to nucleotide position 3145, and/or a guanine at a position corresponding to nucleotide position 3151 as depicted in FIG. 2A, or a feline coronavirus comprising a nucleic acid comprising an adenine at a position corresponding to nucleotide position 3145, and/or a thymine at a position corresponding to position 3151 of the gene encoding a feline coronavirus spike protein as depicted in FIG. 2A, or a feline coronavirus comprising a feline coronavirus spike protein or immunogenic part thereof comprising a methionine at a position corresponding to amino acid position 1049, and/or a serine at a position corresponding to amino acid position 1051 as depicted in FIG. 2B, or any combination thereof, for the preparation of an immunogenic composition or prophylactic agent for eliciting an immune response against a feline coronavirus, preferably a feline infectious peritonitis virus (FIPV), in a feline.

The invention is further explained in the following examples. These examples do not limit the scope of the invention, but merely serve to clarify the invention.

FIGURE LEGENDS

FIG. 1. Schematic representation of the feline coronavirus RNA genome. The 5' part (left) specifies the precursors encoding the replication and transcription functions derived from open reading frames (ORFs) 1a and 1b. Downstream thereof, towards the 3' end, the genes for the structural proteins S (spike protein), E (envelope protein), M (membrane protein) and N (nucleocapsid protein), and for the accessory proteins 3a, 3b, 3c, 7a and 7b are located.

FIG. 2. A) Nucleotide sequences of the feline coronavirus spike gene (nucleotides 1-4407, SEQ ID NO:6), corresponding to nucleotides 20395-24801 of a feline coronavirus as defined in the nucleotide sequence of NC_012955 (Feline coronavirus UU10, complete genome) and nucleotides 20382-24788 (SEQ ID NO:7) of a feline coronavirus as defined in the nucleotide sequence of NC 012952 (Feline coronavirus UU8, complete genome). B) Amino acid sequences of feline coronavirus spike protein (SEQ ID NO:8 and 9), as defined in the amino acid sequence of YP_003038574 and YP_003038543.

Figure 3:
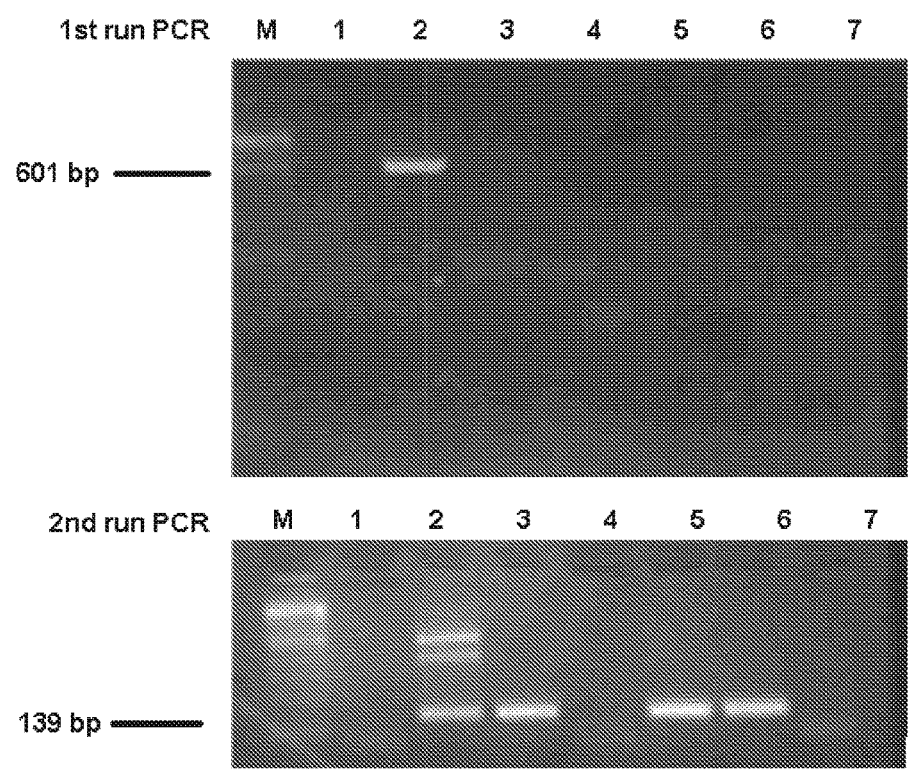

FIG. 3. Agarose gel electrophoresis of amplified RNA from 6 clinical samples obtained from faeces of infected cats. Lane M is a molecular size standard, lanes 1-6 are the clinical samples and lane 7 is a negative control.

FIG. 4. A) Alignment of partial sequences of faeces or plasma derived FCoV RNA isolated from 42 healthy cats and five partial sequences derived from samples of FIP-confirmed cats, i.e. Q093501030_326B_4546.scf (white blood cell derived), Q093501032_327B_4546.scf (white blood cell derived), Q093501036_321S_4546.scf (serum derived), Q093501038_321A_4546.scf (ascites derived) and Q093501046_K11_019.ab1 (white blood cell derived) (SEQ ID NO:10-104); B) Alignment of partial sequences of lesion-derived FCoV RNA isolated from 54 FIP-confirmed cats (SEQ ID NO:105-210); C) Alignment of partial sequences of faeces-derived FCoV RNA isolated from FIP-confirmed cats (SEQ ID NO:211-238). On the right of FIGS. 4A, B and C the identity code of the analysed feline coronavirus is indicated. The targeted nucleotides and predicted amino acid is indicated by an arrow.

EXAMPLES

Example 1

In this example 6 clinical samples (faeces) were analyzed. RNA was extracted from the clinical samples, RT-PCR was applied to the extracted RNAs and the products were analyzed by agarose gel electrophoresis (see FIG. 3) after the first PCR (1st run) and after the nested PCR (2nd run).

Materials and Methods

A nested RT-PCR was used to amplify the FCoV spike gene region containing the target point mutation. Genomic RNA was extracted from faeces of 6 healthy cats using the QIAamp Viral RNA Mini Kit and Qiagen RNeasy Mini Kit (Qiagen, Inc.) according to the manufacturer's instructions. cDNA synthesis was performed with M-MLV reverse transcriptase (RT) and followed by polymerase chain reaction (PCR) amplification with Taq DNA polymerase. All enzymes were used according to the manufacturer's instructions (Promega Corp., Madison, Wis.). Both reactions were primed with specific primers (see primers table 1). Primers were designed using the FCoV genome sequences with accession numbers of NC_012955 and NC_012952. Amplifications was performed using 30 cycles of 94° for 60 s, 50° for 30 s, and 72° for 1 min and additional extension at 72° for 7 min at the end of amplification. The PCR fragments were isolated and purified from agarose gel after electrophoresis using the Qiagen gel Extraction kit (Qiagen Benelux B.V., Venlo, The Netherlands). Sequencing was performed by BaseClear Holding B.V. (Leiden, The Netherlands).

Results

After the first PCR, a 601-bp fragment was obtained only in one clinical sample, as is seen in lane 2 of FIG. 3. After the second round of PCR, a 139-bp fragment was amplified when the nested primers were applied on the products of the 1st run RT-PCR. Now a product was seen not only in lane 2, but also with the amplified RNA's shown in lanes 3, 5 and 6.

Example 2

In this example faecal or plasma samples of 47 healthy cats, clinical samples of 54 FIP-confirmed cats and faecal samples of 14 FIP-confirmed cats were analyzed.
Material and Methods Genomic RNA extraction, cDNA synthesis, amplification and sequencing were performed according to the materials and methods of example 1.
Results The nucleic acid sequence encoding a methionine at amino acid position 1049 was detected in all (47/47) faeces or plasma derived FCoVs from healthy cats (FIG. 4A). It was later found that FIG. 4A contains five sequences derived from samples of cats with confirmed FIP (Q093501030_326B_4546.scf, Q093501032_327B_4546.scf, Q093501036_321S_4546.scf, Q093501038_321A_4546.scf and Q093501046_K11_019.ab1), meaning that in 42/42 faeces or plasma derived FCoVs from healthy cats a methionine was present at amino acid position 1049. This sequence was also observed in 2/54 lesion-derived (FIG. 4B) and 12/14 faeces-derived (FIG. 4C) RNAs amplified from FIP-confirmed cats. Importantly, 52/54 (96%) lesion-derived RNAs from FIP-confirmed cats had an alteration of A to C or T at position 3145, leading to an amino acid alteration at position 1049 that changes a methionine into a leucine (FIG. 4B).

Example 3

We continued collecting samples and cats through veterinarians and owners in the Netherlands. In this example the following samples were analyzed:
faecal samples of 352 healthy cats,
white blood cell samples of 89 healthy or non-FIP suspected cats,
plasma samples of 89 healthy or non-FIP suspected cats,
serum samples of 56 healthy or non-FIP suspected cats,
FIP lesion samples (mesenteric lymph node (LN) and/or kidney and/or spleen and/or omentum and/or lung and/or LN and/or liver and/or ascites) of 97 FIP-confirmed cats,
white blood cell samples of 34 FIP-confirmed cats,
plasma samples of 34 FIP-confirmed cats, and
serum samples of 15 FIP-confirmed cats.
Material and Methods Genomic RNA extraction, cDNA synthesis, amplification and sequencing were performed according to the materials and methods of example 1.
Results
Samples from Healthy Cats 137/352 (39%) of faeces samples were FCoV positive. A nucleic acid sequence encoding a methionine at amino acid position 1049 and a serine at amino acid position 1051 was detected in all (137) faeces-derived FCoVs from healthy cats.

Samples from Healthy or Non-FIP Suspected Cats

EDTA-blood samples from 89 healthy or non-FIP suspected cats were obtained and separated into white blood cells (WBC) and plasma. Serum samples from 56 healthy or non-FIP suspected cats were obtained.

20/89 white blood cells samples, 4/89 plasma samples and 8/56 serum samples were FCoV positive. All 4 plasma-positive samples were also positive in the WBC fraction and in each animal the sequence in plasma was 100% identical to that in WBC. A nucleic acid sequence encoding a methionine at amino acid position 1049 and a serine at amino acid position 1051 was detected in all samples tested positive for FCoV.
Samples from FIP-Confirmed Cats A total of 97 FIP-confirmed cats were studied. 97/97 organs with typical FIP lesions (including mesenteric LN and/or kidney and/or spleen and/or omentum and/or lung and/or LN and/or liver and/or ascites) tested positive for FCoV. 87/97 (90%) of lesion-derived RNAs from FIP-confirmed cats had an amino acid alteration at position 1049 that changes a methionine into a leucine. 5/97 (5%) of lesion-derived RNAs from FIP-confirmed cats had an amino acid alteration at position 1051 that changes a serine into an alanine. In all 5 samples in which an alanine was present at position 1051, a methionine was present at position 1049. Thus, 92 out of 97 (95%) lesion-derived RNA's from FIP confirmed cats had an amino acid alteration indicative for FIP, whereas 5 out of 97 (5%) did not have an amino acid alteration indicative for FIP.

From 34 of the 97 FIP-confirmed cats blood was obtained before euthanizing the animal. Blood samples were separated into white blood cells (buffy coat) and plasma. Serum samples from 15 FIP-confirmed cats were obtained of which EDTA-blood had also been obtained.
WBC:

34/34 (100%) of WBC samples were FCoV positive. In 29/34 (85%) of WBC-derived RNAs from FIP-confirmed cats a leucine was present at position 1049 and a serine was present at position 1051; for all 29 a leucine was present also at position 1049 in the organ samples. Of the 5 cats with a methionine at position 1049 in WBC samples, 2 had a leucine at this position in organ(s) containing FIP-lesions, the other 3 had none of the amino acid alterations indicative for FIPV. Thus, from the 31/34 (90%) FIP cats in which a leucine was detected at position 1049 in organ material, leucine was also detected at this position in WBC in 29/31 (94%) cases.
Plasma:

14/34 (41%) of plasma samples were FCoV positive. In 11/34 (32%) plasma-derived RNA from FIP-confirmed cats a leucine was present at position 1049 and a serine was present at position 1051. Of the 3 FCoV positive cats with a methionine at position 1049 in plasma, 1 had a leucine at this position in FCoV RNA of organ(s) containing FIP-lesions, the other 2 had none of the amino acid alterations indicative for FIPV. Thus, from the 31/34 (90%) FIP cats in which a leucine was detected at position 1049 in organ material, leucine was also detected in plasma in 11/31 (35%) cases.
Serum:

4/15 (27%) serum samples were FCoV positive. In 2/15 (13%) serum-derived RNA from FIP-confirmed cats a leucine was present at position 1049 and a serine was present at position 1051. 15/15 (100%) of these cats had a leucine at position 1049 in organ derived FCoV RNA.

TABLE 1

Primers used for amplification of the FCoV spike gene target region.

| Primers 5'-3' | Position in spike gene | |
|---|---|---|
| CCCTCGAGTCCCGCAGAAACCATACCTA (SEQ ID NO: 1) | 3642-3656 | Reverse primer for 1$^{st}$ run RT-PCR |
| CAATATTACAATGGCATAATGG (SEQ ID NO: 2) | 3055-3076 | Forward primer for 1$^{st}$ run RT-PCR |
| GGCATAATGGTTTTACCTGGTG (SEQ ID NO: 3) | 3067-3088 | Forward primer for 2$^{nd}$ run RT-PCR |
| TAATTAAGCCTCGCCTGCACTT (SEQ ID NO: 4) | 3188-3206 | Reverse primer for 2$^{nd}$ run RT-PCR |

REFERENCES

Barany, F. (1991) Genetic disease detection and DNA amplification using cloned thermostable ligase. Proc. Natl. Acad. Sci. USA 88: 189-193.

Baron H, Fung S, Aydin A, Bahring S, Luft F C, Schuster H. Oligonucleotide ligation assay (OLA) for the diagnosis of familial hypercholesterolemia. Nat Biotechnol. 1996 October; 14(10): 1279-82.

Boom R, Sol C J, Salimans M M, Jansen C L, Wertheim-van Dillen P M, van der Noordaa J. Rapid and simple method for purification of nucleic acids. J Clin Microbiol. 1990 March; 28(3):495-503.

Brown M A, Troyer J L, Pecon-Slattery J, Roelke M E, O'Brien S J. Genetics and pathogenesis of feline infectious peritonitis virus. Emerg Infect Dis. 2009; 15(9): 1445-52.

Chomczynski P, Sacchi N. Single-step method of RNA isolation by acid guanidinium thiocyanate-phenol-chloroform extraction. Anal Biochem. 1987 April; 162(1):156-9.

Compton, J. (1991) Nucleic acid sequence-based amplification. Nature 1991, 350:91-92.

Crain P F, McCloskey J A. Applications of mass spectrometry to the characterization of oligonucleotides and nucleic acids [Review]. Curr Opin Biotechnol 1998; 9:25-34.

Day I N, Spanakis E, Palamand D, Weavind G P, O'Dell S D. Microplate-array diagonal-gel electrophoresis (MADGE) and melt-MADGE: tools for molecular-genetic epidemiology. Trends Biotechnol. 1998 July; 16(7): 287-90.

Devereux J, Haeberli P, Smithies O. A comprehensive set of sequence analysis programs for the VAX. Nucleic Acids Res. 1984 Jan. 11; 12(1 Pt 1):387-95.

Dye C, Siddell S G. Genomic RNA sequence of feline coronavirus strain FCoV C1Je. J Feline Med Surg. 2007 June; 9(3):202-13.

Fakhrai-Rad H, Pourmand N, Ronaghi M. Pyrosequencing: an accurate detection platform for single nucleotide polymorphisms. Hum Mutat. 2002 May; 19(5):479-85.

Fan, J. B., Chen, X., Halushka, M. K., Berno, A., Huang, X., Ryder, T., Lipshutz, R. J., Lockhart, D. J. and Chakravarti, A. (2000) Parallel genotyping of human SNPs using generic high-density oligonucleotide tag arrays. Genome Res., 10, 853-860.

Fehr D, Holznagel E, Bolla S, Hauser B, Herrewegh A A, Horzinek M C, Lutz H. Placebo-controlled evaluation of a modified life virus vaccine against feline infectious peritonitis: safety and efficacy under field conditions. Vaccine. 1997 July; 15(10):1101-9.

Fischer S G, Lerman L S. Separation of random fragments of DNA according to properties of their sequences. Proc Natl Acad Sci USA. 1980 August; 77(8):4420-4.

Guatelli, J. C., Whitf[iota]eld, KM., Kwoh, D. Y., Barringer, K. J., Richman, D. D., Gingeras, T. R. (1990) Isothermal, in vitro amplification of nucleic acids by a multienzyme reaction modeled after retroviral replication. Proc. Natl. Acad. Sd. USA 87:1874-1878.

Haijema, B. J., P. J. Rottier, and R. J. de Groot. 2007. Feline coronaviruses: a tale of two-faced types, p. 183-203. In V. Thiel (ed.), Coronaviruses. Molecular and cellular biology. Caister Academic Press, Norfolk, United Kingdom.

Kennedy, M., Boedeker, N., Gibbs, P., Kania, S. (2001) Deletions in the 7a ORF of feline coronavirus associated with an epidemic of feline infectious peritonitis. Vet. Microbiol. 81, 227-234.

Kwoh, D. Y., Davis, G. R., Whitefield, K. M., Chappelle, H. L., DiMichele, L. J., Gingeras, T. R. (1989) Transcription-Based Amplification System and Detection of Amplified Human Immunodeficiency Virus Type 1 with a Bead-Based Sandwich Hybridization Format. Proc. Natl Acad. Sd. USA, 86, 1173-1177.

Lizardi, P. M., Guerra, C. E., Lomeli, H., Tussie-Luna, I., Kramer, F. R. (1988) Exponential amplification of recombinant RNA hybridization probes. Biotechnology 6, 1197-1202.

Makino R, Yazyu H, Kishimoto Y, Sekiya T, Hayashi K. F-SSCP: fluorescence-based polymerase chain reaction-single-strand conformation polymorphism (PCR-SSCP) analysis. PCR Methods Appl. 1992 August; 2(1):10-3.

McArdle F, Tennant B, Bennett M, Kelly D F, Gaskell C J, Gaskell R M. Independent evaluation of a modified FIPV vaccine under experimental conditions (University of Liverpool experience). Feline Pract. 2005; 23:67-71.

Morlan J, Baker J, Sinicropi D. Mutation detection by real-time PCR: a simple, robust and highly selective method. PLoS One. 2009; 4(2):e4584.

Motokawa K, Hohdatsu T, Hashimoto H, Koyama H. Comparison of the amino acid sequence and phylogenetic analysis of the peplomer, integral membrane and nucleocapsid proteins of feline, canine and porcine coronaviruses. Microbiol Immunol. 1996; 40(6):425-33.

Mullis, K. B., Faloona, F. A. (1987) Specific synthesis of DNA in vitro via a polymerasecatalyzed chain reaction. Meth. Enzymol. 155:335-350.

Pedersen N C. A review of feline infectious peritonitis virus infection: 1963-2008. Feline Med Surg. 2009 April; 11(4):225-58.

Poland A M, Vennema H, Foley J E, Pedersen N C. Two related strains of feline infectious peritonitis virus isolated from immunocompromised cats infected with a feline enteric coronavirus. J Clin Microbiol. 1996 December; 34(12):3180-4.

Rottier P J, Nakamura K, Schellen P, Volders H, Haijema B J. Acquisition of macrophage tropism during the pathogenesis of feline infectious peritonitis is determined by mutations in the feline coronavirus spike protein. J Virol. 2005 November; 79(22):14122-30.

Sanger, F., Nicklen, S., Coulson, A. R. (1977) DNA sequencing with chain-terminating inhibitors. Proc. Natl. Acad. Sci. U.S.A. 74; 5463-5467.

Sanger, F., Nicklen, S., Coulson, A. R. (1977) DNA sequencing with chain-terminating inhibitors. Proc. Natl. Acad. Sci. U.S.A. 74; 5463-5467.

Vennema H, Poland A, Foley J, Pedersen N C. Feline infectious peritonitis viruses arise by mutation from endemic feline enteric coronaviruses. Virology. 1998 Mar. 30; 243(1):150-7.

Walker, G. T., Fraiser, M. S., Schram, J. L., Little, M. C., Nadeau, J. G., Malinowski, D. P. (1992) Strand displacement amplification—an isothermal, in vitro DNA amplification technique Nucleic Acids Res 20:1691-1696.

SEQUENCE LISTING

<160> NUMBER OF SEQ ID NOS: 238

<210> SEQ ID NO 1
<211> LENGTH: 28
<212> TYPE: DNA
<213> ORGANISM: Artificial
<220> FEATURE:
<223> OTHER INFORMATION: primer

<400> SEQUENCE: 1
ccctcgagtc ccgcagaaac cataccta                                      28

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
caatattaca atggcataat gg                                            22

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
ggcataatgg ttttacctgg tg                                            22

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
taattaagcc tcgcctgcac tt                                            22

<210> SEQ ID NO 5
<211> LENGTH: 14
<212> TYPE: DNA
<213> ORGANISM: Artificial
<220> FEATURE:
<223> OTHER INFORMATION: primer

<400> SEQUENCE: 5
cccarrgcca tagg                                                     14

<210> SEQ ID NO 6
<211> LENGTH: 4407
<212> TYPE: DNA
<213> ORGANISM: Feline coronavirus

```
<400> SEQUENCE: 6
atgatgttgt taatacttgc gcttcttagt accgctcact ctgaagatgc gcctcatggt      60
gttacattac cacaatttaa cacttcccat gacaatgcca agtttgaact taatttttac     120
aatttcttac aaacttggga tataccacca aacactgaaa ctattcttgg tggctatcta     180
ccatattgtg ctgaaggtgt caattgtggg tggcataatt ttgcttttcca gcaacatgat    240 gccctaaatg gtaagtatgc ctacataaat tcgcaaaact tgggtatacc gaatgtccac    300
ggcgtctact ttgacgtacg agaacgctat tatgatgacg gcgtatggga ggcagtcgat    360
agagttggcc tattgatakc tatacatggc aaatctcact acagtttact aatggtttta    420
caagacaack ttgaggagaa tcagcctcat gttgccgtta aaatctgcca ttggaaacca    480
ggtaacataa gttcttacca tcaatttagt gttaatctag agatagtgg tcagtgcgtg    540 tttaaccgga ggttctcatt ggacaccaag ttgacagctg atgatttcta tggcttccag    600
tggactgata catctgtaga catatattta ggtggcacta ttactaaagt gtgggtagac    660
aacgattgga gtgttgttga agctagtatt tcccattatt ggagtggtgc tagctatggc    720
tattacatgc aatttgtcaa ccgcaccact tattatgcct acaataatac tggtggttca    780
aattatactc atttacagtt aagtgagtgc agcagtgact actgtgctgg ttatgctaag    840
aatgtctttg tgccaattga tggcaaaata ccagaaagct tctcttttag taactggttt    900
ctgttatcag ataaatccac tttagtgcaa ggacgtgttc ttagtaaaca acctgttctt    960
gtacagtgcc ttaggcccgt gccaacgtgg tctaacaata ctgctgtggt gcattttaaa   1020
aatgatgtct tctgccccaa cgttacggcg aagttttga ggttcaactt gaactttagt    1080
gacagtgatg tttacacaga gtcaagcata gatgatcagt tgtattttac atttgaagat   1140
aacacaaatg catccatagc ctgttatagc agtgctaatg tcactgattt tcaacccgca   1200
aatcaaagcg tctctcacat cccatttgga aaaactgatc acgcttattt tgttttgcc    1260 actttttcta gttctgttgt gggtagacag ttcttgggta tactgccacc aactgtccga    1320
gagtttgcat tcggcagaga tggatccatt tttgttaatg gttataaata tttcagttta   1380
tcacctatca agagtgttaa cttctccatc agttcagtag agaattatgg cttttggacc   1440
atagcttaca ccaactatac agatgtaatg gtggatgtta atggcactgg tatcactagg   1500
ttattctatt gcgactcacc cctcaataga atcaagtgtc aacaattgaa gcatgagcta   1560
ccagatggat tttattctgc tagcatgctt gttaaaaagg atctacctaa acatttgta    1620 actatgccac agttttatga ttggatgaat gtcacgttac atgtcgtgtt gaatgatact   1680 gaaaaggga aggatatcat tttggctaag gctgccgaac tagcatcact tgctaatgta   1740
cattttgaaa tagcccaggc taatggcagt gtaactaatg ttactagcct gtgtgtgcaa    1800
acaagacaat tggctctatt ctataagtat actagcgtac aaggtttgta tacttattcc   1860
aatttagtag agttacaaaa ttatgactgc ccttttttcac cacaacagtt taataattat   1920
ctgcagttcg aaactttgtg ttttgatgtg aacccatctg tcgcaggctg taagtggtcg   1980
ttagttcatg atgttaagtg gcgcacacag ttcgctacta ttactgtttc ttacaaggag   2040
ggtgctatga taacgaccat gccgaaggcg cagctgggtt ttcaagatat ttccaattta   2100
gtaaaagatg aatgcactga ttacaatata tatggatttc agggcacagg cattattaga   2160
aataccacat caagattggt cgctggcctt tactacacgt cagttagtgg tgayctttctt   2220 gcgtttaaga atagcactac aggtgaaatt ttcaccgtag tgccatgtga cttaacagct   2280
caagcagcag tgattaatga cgagatagtg ggagctataa cagccatcaa tcaaactgat   2340
```

```
ctgtttgagt tgtaaatca cacaagttca aaaagatcac gcagatcagc accaataaca    2400
ccaaccacct atactatgcc acaattctat tacataacaa agtggaataa tgacacttcg    2460
tctaattgta cgtctaccat cacttattct tcctttgcta tttgtaatac tggtgaaatt    2520
agatatgtta atgtcactaa ggttgaaatt gtggatgata gtataggagt tatcaaacct    2580
gtttcaacag gcaacatatc aatacctaaa aatttcactg ttgcagtgca ggccgaatac    2640
attcagattc aagtcaaacc tgtcgttgtg gattgtgcca agtatgtctg caatggtaac    2700
agacattgcc ttaacttgtt aacacaatac acttcagctt gtcagacaat tgaaaatgcc    2760
cttaaccttg gtgcacgcct tgaatcttta atgcttaagg atatgattac agtatcagat    2820
cacagtttag agcttgcaac tgttgaaaag tttaacagta ctgttgtagg tggtgaaagg    2880
cttggtggtt tctattttga cggtttgaga aatttgttac caactagcat ggtaagagg    2940 tcagctattg aagatctatt gttcaacaaa gttgtgacca gcggtcttgg cactgttgac    3000
gatgactata aaaagtgctc ttctggcact gatgttgcag atctagtttg tgcccaatat    3060
tacaatggca taatggtttt acctggtgtt gtggatgaca ataagatggc catgtacact    3120
gcctctttaa taggaggtat ggctatgggc tctattacat ccgctgtagc tgttccttt    3180 gccatgcaag tgcaggctag acttaactat gtcgcattac aaactgatgt actacaggaa    3240
aaccagaaaa tacttgctaa tgcttttaat aatgccattg gtaacatcac actagcgctt    3300
ggaaaagttt ccaatgctat tacaaccatc tcagatggtt ttaatagtat ggcctcagca    3360
ttgactaaga ttcagagtgt agttaatcaa caggtgaag cgttgagtca acttaccagt    3420
cagttgcaga aaaatttcca ggccattagt agttctattg ctgaaattta taatagactg    3480
gaaaaagtag aagctgatgc tcaagttgac cgtctcatta ctggtagatt ggcagcactt    3540
aatgcttatg tgtctcaaac tttaactcag tatgctgaag ttaaggctag taggcaactg    3600
gcaatggaga agttaatga gtgtgttaaa tctcagtcgg ataggtatgg gttctgtgga    3660
aatggaacac accctattctc acttgtcaat tctgcacctg atggttact tttctttcac    3720 acagtgttac ttcctacgga atgggaagag gtgacggcat ggtcaggaat atgtgttaat    3780
gacacatatg catatgtgtt gaaagacttt gaatattcta tttttagcta taatggcacg    3840
tatatggtaa ctcctcgtaa tatgtttcaa cctagaaaac ctcagatgag tgatttcgtg    3900
caaattacga gttgtgaggt gacttttctg aacactacat atacgaaatt tcaagagatt    3960
gtgattgatt atattgacat caacaagact atcgttgata tgcttgaaca atataatcct    4020
aattacacaa cacctgaatt acatctacag ctggaaatct ttaatcagac aaaagctaaac    4080 ctcactgcag aaatagacca attagaacaa agagcagaca accttactaa tatagcgcat    4140
gagctacagc agtacattga caaccttaat aagacgcttg ttgaccttga atggctcaac    4200
agggttgaaa cttatgtaaa atggccttgg tatgtgtggc tactaatcgg attagtagta    4260
gtattctgca taccattgtt actgtttttg cgtctagtga ctggctgttg tgggtgtttt    4320
ggttgtcttg gaagttgttg caattctctt tgtagtagaa gacaatttga aagttacgaa    4380
cccatcgaaa aggttcacat tcattaa                                       4407
```

<210> SEQ ID NO 7
<211> LENGTH: 4407
<212> TYPE: DNA
<213> ORGANISM: Feline coronavirus

<400> SEQUENCE: 7

```
atgatgttgt taatacttgc gcttcttagt accgctcact ctgaagatgc gcctcatggt      60
gttacattac cacaatttaa cacttcccat ggcaatgaca gtttgaact  taattttac      120
aatttcttac aaacttggga tataccacca aacactgaaa ctattttggg tggctatcta     180
ccatattgtg ctgaaggtgt caattgtggg tggcataatt ttgcttccca gcaacatgat     240
gccctaaatg gtaagtatgc ctacataaat tcgcaaaact tgggtatacc gaatgtccac     300
ggcgtctact ttgacgtacg agaacgctat tatgatgacg gcgtatggga tgcagtcgat     360
agagttggcc tattgatagc tatacatggc aaatctcact acagtttact aatggtttta     420
caagacaacg ttgaggagaa tcagcctcat gttgccgtta aaatctgcca ttggaaacca     480
ggtaacataa gttcttacca tcaatttagt gttaatctag agatagtgg  tcagtgcgtg     540
tttaaccgga ggttctcatt ggacaccaag ttgacagctg atggtttcta tggcttccag     600
tggactgata catctgtaga catatattta ggtggcacta ttactaaagt gtgggttgac     660
aacgattgga gtgttgttga agctagtatt tcccattttt ggagtggtac tagctatggc     720
tattacatgc aatttgtcaa ccgcacaacc tattatay tt acaataatac acttggctca    780
aattatacac atttgcagtt aagcgagtgc agtagtgatt attgtgctgg ttatgctaaa     840
aatgtctttg tgccagttgg tggcaagata ccagagagtt attcttttag taactggttt     900
ctgttatcag acaaatccac tttggtgcaa ggacgtgttc ttagtaaaca acctgttctt     960
gtacagtgcc ttaggcccgt gccaacgtgg tctaacaata ctgctgtggt gcattttaaa    1020
aatgacgtct tctgccccaa cgttacggcg gaagttttga ggttcaactt gaactttagt    1080
gacagtgatg tttacacaga gtcaagcata gatgatcagt tgtattttac atttgaagat    1140
aacacaaatg catccatagc ctgttatagc agtgctaatg tcactgatct tcaacccgca    1200
aatcaaagcg tctctcacat cccatttgga aaaactgatt acgcttattt ttgttttgcc    1260
acttttttcta gttctgttgt gggtagacag ttcttgggta tactkccacc aactgtccga    1320
gagtttgcat tcggcagaga tggatccatt tttgttaatg gttataaata tttcagttta    1380
ccacctatca agagtgttaa cttctccatc agttcagtag agaattatgg cttttggacc    1440
atagcttaca ccaactatac agatgtaatg gtggatgtta atggcactgg tatcactagt    1500
ttattctatt gcgactcacc cctcaataga atcaagtgtc aacaattgaa gcatgagcta    1560
ccagatggat tttattctgc tagcatgctt gttaaaaagg atctacctaa gacatttgta    1620
actatgccac agttttatga ttggatgaat gtcacgttac atgtcgtgtt gaatgatact    1680
gaaaaggga  aggatatcat tttggctaag gctgccgaac tagcatcact tgctaatgta    1740
cattttgaaa tagcccaggc taatggcagt gtaactaatg ttactagcct gtgtgtgcaa    1800
acaagacaat tggctctatt ctataagtat actagcttac aaggtttgta tacttattcc    1860
aatttagtag agttacaaaa ttatgactgc cctttttcac cacaacagtt taataattat    1920
ctgcagttcg aaactttgtg ttttgatgtg aacccatctg tcgcaggctg taagtggtcg    1980
ttagttcatg atgttaagtg gcgcacacag ttcgctacta ttactgtttc ttacaaggag    2040
ggtgctatga taacgaccat gccgaaggcg cagctgggtt ttcaagatat ttccaattta    2100
gtaaagatg  aatgcactga ttacaatata tatggatttc agggcacagg cattattaga    2160
aataccacct caagattagt agctggcctt tactacacat ccattagtgg tgaccttctt    2220
gcctttaaaa acagtactac aggtgaaatt tcactgtggt gccatgtga tctaacagca    2280
caagcagctg tgattaacga tgaaatagtg ggagctataa cagccgttaa tcaaacagat    2340
ctgtttgagt ttgtgaatca cacacaatca agaagatcac gtaggtcaac ctccgacaca    2400
```

```
gtaaaaacct atactatgcc gcaattttat tacataacaa agtggaataa tgacaccttg    2460
actaattgta cgtctgtcat tacatattct tcctttgcta tttgtaatac tggtgaaatt    2520
aaatatgtta atgtcactaa ggttgaaatt gtggatgata gtataggagt tatcaaacct    2580
gtttcaacag gcaacatatc aatacctaaa aatttcactg ttgcagtgca ggccgaatac    2640
attcagattc aagtcaaacc tgtcgttgtg gattgtgcta agtatgtttg caatggtaac    2700
agacattgcc ttactttgct aacacaatat acttcagctt gtcaaacaat tgaaaatgcc    2760
cttagtcttg gtgcacgtct tgaatctttg atgcttaagg atatgattac agtatcagat    2820
cacagtttaa agcttgcaac tgttgaaaag tttaacagta ctgttgtagg tggtgaaagg    2880
cttggtggtt tctattttga cggtttgaga gatttgttac cacctagcat tggtaagagg    2940
tcagttattg aagatctatt gtttaataaa gtggtaacca gcggtcttgg cactgttgat    3000
gatgattata aaaagtgctc agctggtaca gatgttgcag atctagtttg tgcccagtat    3060
tacaatggta taatggtttt acctggcgtc gtagatgata taagatggc catgtatact    3120 gcatccttaa taggaggcat ggctctgggt tctattacat cagctgtcgc cgtgccttt     3180 gctatgcaag ttcaggctag acttaactat gtcgcattac aaactgatgt actacaggaa    3240
aaccagaaaa tacttgctaa cgcttttaat aatgccattg gtaacattac actagcgctt    3300
ggaaaagttt ccaatgctat tacaaccata tcagatggtt ttaatattat ggcctcagca    3360
ttgactaaga ttcagagtgt agttaatcaa cagggtgaag cgttgagtca acttaccagt    3420
cagttgcaga aaaatttcca ggccattagt agttctattg ctgaaattta taatagactg    3480
gaaaaagtag aagctgatgc tcaagttgac cgtctcatta ctggtagatt ggcagcactt    3540
aatgcttatg tgtctcaaac tttaactcag tatgctgaag ttaaggctag taggcaactg    3600
gcaatggaga agttaatga gtgtgttaaa tctcagtcgg ataggtatgg gttctgtgga    3660
aatggaacac acctattctc acttgtcaat tctgcacctg atggtttact tttcttcac    3720 acagtgttac ttcctacgga atgggaagag gtgacggcat ggtcaggaat atgtgttaat    3780
gacacatatg catatgtgtt gaaagacttt gaatattcta tttttagcta taatggtacg    3840
tatatggtaa ctcctcgtaa tatgtttcaa cctagaarac ctcagatgag tgatttcgtg    3900
caaattacga gatgtgaagt gacttttctg aacactacat atacgacatt tcaggagatt    3960
gtgattgatt atattgatat taacaagact atcgctgata tgcttgagca atataatcct    4020
aattacacaa cacctgaatt agatttacag atagaaattt tcaaccagac aaagttaaac    4080
ctcactgcag aaatagacca attagaacag cgagctgaca acctcaccac tatagcacgt    4140
gagctacagc agtacattga caatcttaat aagacgctag ttgacctcga atggctcaac    4200
aggattgaaa cttatgtaaa atggccttgg tatgtgtggc tactgatcgg attagtagta    4260
gtattctgca taccattgtt actgttttgc tgtctgagta ctggctgttg tgggtgtttt    4320
ggttgtcttg gaagttgttg caattctctt tgtagtagaa gacaatttga aagttacgaa    4380
cccatcgaaa aggttcacat tcattaa                                         4407
```

<210> SEQ ID NO 8
<211> LENGTH: 1468
<212> TYPE: PRT
<213> ORGANISM: Feline coronavirus
<220> FEATURE:
<221> NAME/KEY: misc_feature
<222> LOCATION: (127)..(127)
<223> OTHER INFORMATION: Xaa can be any naturally occurring amino acid
<220> FEATURE:

<221> NAME/KEY: misc_feature
<222> LOCATION: (144)..(144)
<223> OTHER INFORMATION: Xaa can be any naturally occurring amino acid

<400> SEQUENCE: 8

```
Met Met Leu Leu Ile Leu Ala Leu Leu Ser Thr Ala His Ser Glu Asp
1               5                   10                  15

Ala Pro His Gly Val Thr Leu Pro Gln Phe Asn Thr Ser His Asp Asn
            20                  25                  30

Ala Lys Phe Glu Leu Asn Phe Tyr Asn Phe Leu Gln Thr Trp Asp Ile
        35                  40                  45

Pro Pro Asn Thr Glu Thr Ile Leu Gly Gly Tyr Leu Pro Tyr Cys Ala
50                  55                  60

Glu Gly Val Asn Cys Gly Trp His Asn Phe Ala Phe Gln Gln His Asp
65                  70                  75                  80

Ala Leu Asn Gly Lys Tyr Ala Tyr Ile Asn Ser Gln Asn Leu Gly Ile
                85                  90                  95

Pro Asn Val His Gly Val Tyr Phe Asp Val Arg Glu Arg Tyr Tyr Asp
            100                 105                 110

Asp Gly Val Trp Glu Ala Val Asp Arg Val Gly Leu Leu Ile Xaa Ile
        115                 120                 125

His Gly Lys Ser His Tyr Ser Leu Leu Met Val Leu Gln Asp Asn Xaa
    130                 135                 140

Glu Glu Asn Gln Pro His Val Ala Val Lys Ile Cys His Trp Lys Pro
145                 150                 155                 160

Gly Asn Ile Ser Ser Tyr His Gln Phe Ser Val Asn Leu Gly Asp Ser
                165                 170                 175

Gly Gln Cys Val Phe Asn Arg Arg Phe Ser Leu Asp Thr Lys Leu Thr
            180                 185                 190

Ala Asp Asp Phe Tyr Gly Phe Gln Trp Thr Asp Thr Ser Val Asp Ile
        195                 200                 205

Tyr Leu Gly Gly Thr Ile Thr Lys Val Trp Val Asp Asn Asp Trp Ser
210                 215                 220

Val Val Glu Ala Ser Ile Ser His Tyr Trp Ser Gly Ala Ser Tyr Gly
225                 230                 235                 240

Tyr Tyr Met Gln Phe Val Asn Arg Thr Thr Tyr Tyr Ala Tyr Asn Asn
                245                 250                 255

Thr Gly Gly Ser Asn Tyr Thr His Leu Gln Leu Ser Glu Cys Ser Ser
            260                 265                 270

Asp Tyr Cys Ala Gly Tyr Ala Lys Asn Val Phe Val Pro Ile Asp Gly
        275                 280                 285

Lys Ile Pro Glu Ser Phe Ser Phe Ser Asn Trp Phe Leu Leu Ser Asp
290                 295                 300

Lys Ser Thr Leu Val Gln Gly Arg Val Leu Ser Lys Gln Pro Val Leu
305                 310                 315                 320

Val Gln Cys Leu Arg Pro Val Pro Thr Trp Ser Asn Asn Thr Ala Val
                325                 330                 335

Val His Phe Lys Asn Asp Val Phe Cys Pro Asn Val Thr Ala Glu Val
            340                 345                 350

Leu Arg Phe Asn Leu Asn Phe Ser Asp Ser Val Tyr Thr Glu Ser
        355                 360                 365

Ser Ile Asp Asp Gln Leu Tyr Phe Thr Phe Glu Asp Asn Thr Asn Ala
370                 375                 380

Ser Ile Ala Cys Tyr Ser Ser Ala Asn Val Thr Asp Phe Gln Pro Ala
```

```
385                 390                 395                 400
Asn Gln Ser Val Ser His Ile Pro Phe Gly Lys Thr Asp His Ala Tyr
                405                 410                 415

Phe Cys Phe Ala Thr Phe Ser Ser Val Val Gly Arg Gln Phe Leu
            420                 425                 430

Gly Ile Leu Pro Pro Thr Val Arg Glu Phe Ala Phe Gly Arg Asp Gly
            435                 440                 445

Ser Ile Phe Val Asn Gly Tyr Lys Tyr Phe Ser Leu Ser Pro Ile Lys
            450                 455                 460

Ser Val Asn Phe Ser Ile Ser Ser Val Glu Asn Tyr Gly Phe Trp Thr
465                 470                 475                 480

Ile Ala Tyr Thr Asn Tyr Thr Asp Val Met Val Asp Val Asn Gly Thr
                485                 490                 495

Gly Ile Thr Arg Leu Phe Tyr Cys Asp Ser Pro Leu Asn Arg Ile Lys
            500                 505                 510

Cys Gln Gln Leu Lys His Glu Leu Pro Asp Gly Phe Tyr Ser Ala Ser
            515                 520                 525

Met Leu Val Lys Lys Asp Leu Pro Lys Thr Phe Val Thr Met Pro Gln
    530                 535                 540

Phe Tyr Asp Trp Met Asn Val Thr Leu His Val Val Leu Asn Asp Thr
545                 550                 555                 560

Glu Lys Gly Lys Asp Ile Ile Leu Ala Lys Ala Ala Glu Leu Ala Ser
                565                 570                 575

Leu Ala Asn Val His Phe Glu Ile Ala Gln Ala Asn Gly Ser Val Thr
            580                 585                 590

Asn Val Thr Ser Leu Cys Val Gln Thr Arg Gln Leu Ala Leu Phe Tyr
            595                 600                 605

Lys Tyr Thr Ser Val Gln Gly Leu Tyr Thr Tyr Ser Asn Leu Val Glu
        610                 615                 620

Leu Gln Asn Tyr Asp Cys Pro Phe Ser Pro Gln Gln Phe Asn Asn Tyr
625                 630                 635                 640

Leu Gln Phe Glu Thr Leu Cys Phe Asp Val Asn Pro Ser Val Ala Gly
            645                 650                 655

Cys Lys Trp Ser Leu Val His Asp Val Lys Trp Arg Thr Gln Phe Ala
            660                 665                 670

Thr Ile Thr Val Ser Tyr Lys Glu Gly Ala Met Ile Thr Thr Met Pro
            675                 680                 685

Lys Ala Gln Leu Gly Phe Gln Asp Ile Ser Asn Leu Val Lys Asp Glu
    690                 695                 700

Cys Thr Asp Tyr Asn Ile Tyr Gly Phe Gln Gly Thr Gly Ile Ile Arg
705                 710                 715                 720

Asn Thr Thr Ser Arg Leu Val Ala Gly Leu Tyr Tyr Thr Ser Val Ser
                725                 730                 735

Gly Asp Leu Leu Ala Phe Lys Asn Ser Thr Thr Gly Glu Ile Phe Thr
            740                 745                 750

Val Val Pro Cys Asp Leu Thr Ala Gln Ala Ala Val Ile Asn Asp Glu
            755                 760                 765

Ile Val Gly Ala Ile Thr Ala Ile Asn Gln Thr Asp Leu Phe Glu Phe
            770                 775                 780

Val Asn His Thr Ser Ser Lys Arg Ser Arg Arg Ser Ala Pro Ile Thr
785                 790                 795                 800

Pro Thr Thr Tyr Thr Met Pro Gln Phe Tyr Tyr Ile Thr Lys Trp Asn
                805                 810                 815
```

-continued

```
Asn Asp Thr Ser Ser Asn Cys Thr Ser Thr Ile Thr Tyr Ser Ser Phe
            820                 825                 830

Ala Ile Cys Asn Thr Gly Glu Ile Arg Tyr Val Asn Val Thr Lys Val
            835                 840                 845

Glu Ile Val Asp Asp Ser Ile Gly Val Ile Lys Pro Val Ser Thr Gly
            850                 855                 860

Asn Ile Ser Ile Pro Lys Asn Phe Thr Val Ala Val Gln Ala Glu Tyr
865                 870                 875                 880

Ile Gln Ile Gln Val Lys Pro Val Val Asp Cys Ala Lys Tyr Val
                    885                 890                 895

Cys Asn Gly Asn Arg His Cys Leu Asn Leu Leu Thr Gln Tyr Thr Ser
            900                 905                 910

Ala Cys Gln Thr Ile Glu Asn Ala Leu Asn Leu Gly Ala Arg Leu Glu
            915                 920                 925

Ser Leu Met Leu Lys Asp Met Ile Thr Val Ser Asp His Ser Leu Glu
            930                 935                 940

Leu Ala Thr Val Glu Lys Phe Asn Ser Thr Val Val Gly Gly Glu Arg
945                 950                 955                 960

Leu Gly Gly Phe Tyr Phe Asp Gly Leu Arg Asn Leu Leu Pro Thr Ser
                    965                 970                 975

Ile Gly Lys Arg Ser Ala Ile Glu Asp Leu Leu Phe Asn Lys Val Val
            980                 985                 990

Thr Ser Gly Leu Gly Thr Val Asp Asp Asp Tyr Lys Lys Cys Ser Ser
            995                 1000                1005

Gly Thr Asp Val Ala Asp Leu Val Cys Ala Gln Tyr Tyr Asn Gly
            1010                1015                1020

Ile Met Val Leu Pro Gly Val Val Asp Asp Asn Lys Met Ala Met
            1025                1030                1035

Tyr Thr Ala Ser Leu Ile Gly Gly Met Ala Met Gly Ser Ile Thr
            1040                1045                1050

Ser Ala Val Ala Val Pro Phe Ala Met Gln Val Gln Ala Arg Leu
            1055                1060                1065

Asn Tyr Val Ala Leu Gln Thr Asp Val Leu Gln Glu Asn Gln Lys
            1070                1075                1080

Ile Leu Ala Asn Ala Phe Asn Asn Ala Ile Gly Asn Ile Thr Leu
            1085                1090                1095

Ala Leu Gly Lys Val Ser Asn Ala Ile Thr Thr Ile Ser Asp Gly
            1100                1105                1110

Phe Asn Ser Met Ala Ser Ala Leu Thr Lys Ile Gln Ser Val Val
            1115                1120                1125

Asn Gln Gln Gly Glu Ala Leu Ser Gln Leu Thr Ser Gln Leu Gln
            1130                1135                1140

Lys Asn Phe Gln Ala Ile Ser Ser Ser Ile Ala Glu Ile Tyr Asn
            1145                1150                1155

Arg Leu Glu Lys Val Glu Ala Asp Ala Gln Val Asp Arg Leu Ile
            1160                1165                1170

Thr Gly Arg Leu Ala Ala Leu Asn Ala Tyr Val Ser Gln Thr Leu
            1175                1180                1185

Thr Gln Tyr Ala Glu Val Lys Ala Ser Arg Gln Leu Ala Met Glu
            1190                1195                1200

Lys Val Asn Glu Cys Val Lys Ser Gln Ser Asp Arg Tyr Gly Phe
            1205                1210                1215
```

```
Cys Gly Asn Gly Thr His Leu Phe Ser Leu Val Asn Ser Ala Pro
    1220                1225                1230

Asp Gly Leu Leu Phe Phe His Thr Val Leu Leu Pro Thr Glu Trp
    1235                1240                1245

Glu Glu Val Thr Ala Trp Ser Gly Ile Cys Val Asn Asp Thr Tyr
    1250                1255                1260

Ala Tyr Val Leu Lys Asp Phe Glu Tyr Ser Ile Phe Ser Tyr Asn
    1265                1270                1275

Gly Thr Tyr Met Val Thr Pro Arg Asn Met Phe Gln Pro Arg Lys
    1280                1285                1290

Pro Gln Met Ser Asp Phe Val Gln Ile Thr Ser Cys Glu Val Thr
    1295                1300                1305

Phe Leu Asn Thr Thr Tyr Thr Lys Phe Gln Glu Ile Val Ile Asp
    1310                1315                1320

Tyr Ile Asp Ile Asn Lys Thr Ile Val Asp Met Leu Glu Gln Tyr
    1325                1330                1335

Asn Pro Asn Tyr Thr Thr Pro Glu Leu His Leu Gln Leu Glu Ile
    1340                1345                1350

Phe Asn Gln Thr Lys Leu Asn Leu Thr Ala Glu Ile Asp Gln Leu
    1355                1360                1365

Glu Gln Arg Ala Asp Asn Leu Thr Asn Ile Ala His Glu Leu Gln
    1370                1375                1380

Gln Tyr Ile Asp Asn Leu Asn Lys Thr Leu Val Asp Leu Glu Trp
    1385                1390                1395

Leu Asn Arg Val Glu Thr Tyr Val Lys Trp Pro Trp Tyr Val Trp
    1400                1405                1410

Leu Leu Ile Gly Leu Val Val Phe Cys Ile Pro Leu Leu Leu
    1415                1420                1425

Phe Cys Cys Leu Ser Thr Gly Cys Cys Gly Cys Phe Gly Cys Leu
    1430                1435                1440

Gly Ser Cys Cys Asn Ser Leu Cys Ser Arg Arg Gln Phe Glu Ser
    1445                1450                1455

Tyr Glu Pro Ile Glu Lys Val His Ile His
    1460                1465

<210> SEQ ID NO 9
<211> LENGTH: 1468
<212> TYPE: PRT
<213> ORGANISM: Feline coronavirus
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (1293)..(1293)
<223> OTHER INFORMATION: Xaa can be any naturally occurring amino acid

<400> SEQUENCE: 9

Met Met Leu Leu Ile Leu Ala Leu Leu Ser Thr Ala His Ser Glu Asp
1               5                   10                  15

Ala Pro His Gly Val Thr Leu Pro Gln Phe Asn Thr Ser His Gly Asn
                20                  25                  30

Asp Lys Phe Glu Leu Asn Phe Tyr Asn Phe Leu Gln Thr Trp Asp Ile
            35                  40                  45

Pro Pro Asn Thr Glu Thr Ile Phe Gly Gly Tyr Leu Pro Tyr Cys Ala
        50                  55                  60
```

-continued

```
Glu Gly Val Asn Cys Gly Trp His Asn Phe Ala Ser Gln Gln His Asp
 65                  70                  75                  80

Ala Leu Asn Gly Lys Tyr Ala Tyr Ile Asn Ser Gln Asn Leu Gly Ile
                 85                  90                  95

Pro Asn Val His Gly Val Tyr Phe Asp Val Arg Glu Arg Tyr Tyr Asp
            100                 105                 110

Asp Gly Val Trp Asp Ala Val Asp Arg Val Gly Leu Leu Ile Ala Ile
            115                 120                 125

His Gly Lys Ser His Tyr Ser Leu Leu Met Val Leu Gln Asp Asn Val
        130                 135                 140

Glu Glu Asn Gln Pro His Val Ala Val Lys Ile Cys His Trp Lys Pro
145                 150                 155                 160

Gly Asn Ile Ser Ser Tyr His Gln Phe Ser Val Asn Leu Gly Asp Ser
                165                 170                 175

Gly Gln Cys Val Phe Asn Arg Arg Phe Ser Leu Asp Thr Lys Leu Thr
            180                 185                 190

Ala Asp Gly Phe Tyr Gly Phe Gln Trp Thr Asp Thr Ser Val Asp Ile
            195                 200                 205

Tyr Leu Gly Gly Thr Ile Thr Lys Val Trp Val Asp Asn Asp Trp Ser
210                 215                 220

Val Val Glu Ala Ser Ile Ser His Phe Trp Ser Gly Thr Ser Tyr Gly
225                 230                 235                 240

Tyr Tyr Met Gln Phe Val Asn Arg Thr Thr Tyr Tyr Xaa Tyr Asn Asn
                245                 250                 255

Thr Leu Gly Ser Asn Tyr Thr His Leu Gln Leu Ser Glu Cys Ser Ser
            260                 265                 270

Asp Tyr Cys Ala Gly Tyr Ala Lys Asn Val Phe Val Pro Val Gly Gly
            275                 280                 285

Lys Ile Pro Glu Ser Tyr Ser Phe Ser Asn Trp Phe Leu Leu Ser Asp
            290                 295                 300

Lys Ser Thr Leu Val Gln Gly Arg Val Leu Ser Lys Gln Pro Val Leu
305                 310                 315                 320

Val Gln Cys Leu Arg Pro Val Pro Thr Trp Ser Asn Asn Thr Ala Val
                325                 330                 335

Val His Phe Lys Asn Asp Val Phe Cys Pro Asn Val Thr Ala Glu Val
            340                 345                 350

Leu Arg Phe Asn Leu Asn Phe Ser Asp Ser Asp Val Tyr Thr Glu Ser
            355                 360                 365

Ser Ile Asp Asp Gln Leu Tyr Phe Thr Phe Glu Asp Asn Thr Asn Ala
            370                 375                 380

Ser Ile Ala Cys Tyr Ser Ser Ala Asn Val Thr Asp Leu Gln Pro Ala
385                 390                 395                 400

Asn Gln Ser Val Ser His Ile Pro Phe Gly Lys Thr Asp Tyr Ala Tyr
                405                 410                 415

Phe Cys Phe Ala Thr Phe Ser Ser Val Val Gly Arg Gln Phe Leu
            420                 425                 430

Gly Ile Leu Pro Pro Thr Val Arg Glu Phe Ala Phe Gly Arg Asp Gly
            435                 440                 445

Ser Ile Phe Val Asn Gly Tyr Lys Tyr Phe Ser Leu Pro Pro Ile Lys
            450                 455                 460

Ser Val Asn Phe Ser Ile Ser Ser Val Glu Asn Tyr Gly Phe Trp Thr
465                 470                 475                 480

Ile Ala Tyr Thr Asn Tyr Thr Asp Val Met Val Asp Val Asn Gly Thr
```

-continued

```
                485                 490                 495
Gly Ile Thr Ser Leu Phe Tyr Cys Asp Ser Pro Leu Asn Arg Ile Lys
            500                 505                 510
Cys Gln Gln Leu Lys His Glu Leu Pro Asp Gly Phe Tyr Ser Ala Ser
            515                 520                 525
Met Leu Val Lys Lys Asp Leu Pro Lys Thr Phe Val Thr Met Pro Gln
        530                 535                 540
Phe Tyr Asp Trp Met Asn Val Thr Leu His Val Val Leu Asn Asp Thr
545                 550                 555                 560
Glu Lys Gly Lys Asp Ile Ile Leu Ala Lys Ala Glu Leu Ala Ser
                565                 570                 575
Leu Ala Asn Val His Phe Glu Ile Ala Gln Ala Asn Gly Ser Val Thr
            580                 585                 590
Asn Val Thr Ser Leu Cys Val Gln Thr Arg Gln Leu Ala Leu Phe Tyr
            595                 600                 605
Lys Tyr Thr Ser Leu Gln Gly Leu Tyr Thr Tyr Ser Asn Leu Val Glu
        610                 615                 620
Leu Gln Asn Tyr Asp Cys Pro Phe Ser Pro Gln Gln Phe Asn Asn Tyr
625                 630                 635                 640
Leu Gln Phe Glu Thr Leu Cys Phe Asp Val Asn Pro Ser Val Ala Gly
                645                 650                 655
Cys Lys Trp Ser Leu Val His Asp Val Lys Trp Arg Thr Gln Phe Ala
            660                 665                 670
Thr Ile Thr Val Ser Tyr Lys Glu Gly Ala Met Ile Thr Thr Met Pro
            675                 680                 685
Lys Ala Gln Leu Gly Phe Gln Asp Ile Ser Asn Leu Val Lys Asp Glu
        690                 695                 700
Cys Thr Asp Tyr Asn Ile Tyr Gly Phe Gln Gly Thr Gly Ile Ile Arg
705                 710                 715                 720
Asn Thr Thr Ser Arg Leu Val Ala Gly Leu Tyr Tyr Thr Ser Ile Ser
                725                 730                 735
Gly Asp Leu Leu Ala Phe Lys Asn Ser Thr Thr Gly Glu Ile Phe Thr
            740                 745                 750
Val Val Pro Cys Asp Leu Thr Ala Gln Ala Ala Val Ile Asn Asp Glu
            755                 760                 765
Ile Val Gly Ala Ile Thr Ala Val Asn Gln Thr Asp Leu Phe Glu Phe
        770                 775                 780
Val Asn His Thr Gln Ser Arg Arg Ser Arg Arg Ser Thr Ser Asp Thr
785                 790                 795                 800
Val Lys Thr Tyr Thr Met Pro Gln Phe Tyr Tyr Ile Thr Lys Trp Asn
                805                 810                 815
Asn Asp Thr Leu Thr Asn Cys Thr Ser Val Ile Thr Tyr Ser Ser Phe
            820                 825                 830
Ala Ile Cys Asn Thr Gly Glu Ile Lys Tyr Val Asn Val Thr Lys Val
            835                 840                 845
Glu Ile Val Asp Asp Ser Ile Gly Val Ile Lys Pro Val Ser Thr Gly
        850                 855                 860
Asn Ile Ser Ile Pro Lys Asn Phe Thr Val Ala Val Gln Ala Glu Tyr
865                 870                 875                 880
Ile Gln Ile Gln Val Lys Pro Val Val Asp Cys Ala Lys Tyr Val
                885                 890                 895
Cys Asn Gly Asn Arg His Cys Leu Thr Leu Leu Thr Gln Tyr Thr Ser
            900                 905                 910
```

-continued

```
Ala Cys Gln Thr Ile Glu Asn Ala Leu Ser Leu Gly Ala Arg Leu Glu
            915                 920                 925

Ser Leu Met Leu Lys Asp Met Ile Thr Val Ser Asp His Ser Leu Lys
930                 935                 940

Leu Ala Thr Val Glu Lys Phe Asn Ser Thr Val Val Gly Gly Glu Arg
945                 950                 955                 960

Leu Gly Gly Phe Tyr Phe Asp Gly Leu Arg Asp Leu Leu Pro Pro Ser
            965                 970                 975

Ile Gly Lys Arg Ser Val Ile Glu Asp Leu Leu Phe Asn Lys Val Val
            980                 985                 990

Thr Ser Gly Leu Gly Thr Val Asp Asp Asp Tyr Lys Lys Cys Ser Ala
            995                 1000                1005

Gly Thr Asp Val Ala Asp Leu Val Cys Ala Gln Tyr Tyr Asn Gly
    1010                1015                1020

Ile Met Val Leu Pro Gly Val Asp Asp Asn Lys Met Ala Met
    1025                1030                1035

Tyr Thr Ala Ser Leu Ile Gly Gly Met Ala Leu Gly Ser Ile Thr
    1040                1045                1050

Ser Ala Val Ala Val Pro Phe Ala Met Gln Val Gln Ala Arg Leu
    1055                1060                1065

Asn Tyr Val Ala Leu Gln Thr Asp Val Leu Gln Glu Asn Gln Lys
    1070                1075                1080

Ile Leu Ala Asn Ala Phe Asn Asn Ala Ile Gly Asn Ile Thr Leu
    1085                1090                1095

Ala Leu Gly Lys Val Ser Asn Ala Ile Thr Thr Ile Ser Asp Gly
    1100                1105                1110

Phe Asn Ile Met Ala Ser Ala Leu Thr Lys Ile Gln Ser Val Val
    1115                1120                1125

Asn Gln Gln Gly Glu Ala Leu Ser Gln Leu Thr Ser Gln Leu Gln
    1130                1135                1140

Lys Asn Phe Gln Ala Ile Ser Ser Ser Ile Ala Glu Ile Tyr Asn
    1145                1150                1155

Arg Leu Glu Lys Val Glu Ala Asp Ala Gln Val Asp Arg Leu Ile
    1160                1165                1170

Thr Gly Arg Leu Ala Ala Leu Asn Ala Tyr Val Ser Gln Thr Leu
    1175                1180                1185

Thr Gln Tyr Ala Glu Val Lys Ala Ser Arg Gln Leu Ala Met Glu
    1190                1195                1200

Lys Val Asn Glu Cys Val Lys Ser Gln Ser Asp Arg Tyr Gly Phe
    1205                1210                1215

Cys Gly Asn Gly Thr His Leu Phe Ser Leu Val Asn Ser Ala Pro
    1220                1225                1230

Asp Gly Leu Leu Phe Phe His Thr Val Leu Leu Pro Thr Glu Trp
    1235                1240                1245

Glu Glu Val Thr Ala Trp Ser Gly Ile Cys Val Asn Asp Thr Tyr
    1250                1255                1260

Ala Tyr Val Leu Lys Asp Phe Glu Tyr Ser Ile Phe Ser Tyr Asn
    1265                1270                1275

Gly Thr Tyr Met Val Thr Pro Arg Asn Met Phe Gln Pro Arg Xaa
    1280                1285                1290

Pro Gln Met Ser Asp Phe Val Gln Ile Thr Arg Cys Glu Val Thr
    1295                1300                1305
```

```
Phe Leu Asn Thr Thr Tyr Thr Thr Phe Gln Glu Ile Val Ile Asp
    1310                1315                1320

Tyr Ile Asp Ile Asn Lys Thr Ile Ala Asp Met Leu Glu Gln Tyr
    1325                1330                1335

Asn Pro Asn Tyr Thr Thr Pro Glu Leu Asp Leu Gln Ile Glu Ile
    1340                1345                1350

Phe Asn Gln Thr Lys Leu Asn Leu Thr Ala Glu Ile Asp Gln Leu
    1355                1360                1365

Glu Gln Arg Ala Asp Asn Leu Thr Thr Ile Ala Arg Glu Leu Gln
    1370                1375                1380

Gln Tyr Ile Asp Asn Leu Asn Lys Thr Leu Val Asp Leu Glu Trp
    1385                1390                1395

Leu Asn Arg Ile Glu Thr Tyr Val Lys Trp Pro Trp Tyr Val Trp
    1400                1405                1410

Leu Leu Ile Gly Leu Val Val Val Phe Cys Ile Pro Leu Leu Leu
    1415                1420                1425

Phe Cys Cys Leu Ser Thr Gly Cys Cys Gly Cys Phe Gly Cys Leu
    1430                1435                1440

Gly Ser Cys Cys Asn Ser Leu Cys Ser Arg Arg Gln Phe Glu Ser
    1445                1450                1455

Tyr Glu Pro Ile Glu Lys Val His Ile His
    1460                1465

<210> SEQ ID NO 10
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 10 atg gct atg ggt tct atc act tct gct gtg gct gtt cct ttc gcc atg    48
Met Ala Met Gly Ser Ile Thr Ser Ala Val Ala Val Pro Phe Ala Met
1               5                   10                  15 caa gtg caa gct agg ctt                                            66
Gln Val Gln Ala Arg Leu
            20

<210> SEQ ID NO 11
<211> LENGTH: 22
<212> TYPE: PRT
<213> ORGANISM: Feline coronavirus

<400> SEQUENCE: 11

Met Ala Met Gly Ser Ile Thr Ser Ala Val Ala Val Pro Phe Ala Met
1               5                   10                  15

Gln Val Gln Ala Arg Leu
            20

<210> SEQ ID NO 12
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 12 atg gct atg ggt tct att aca tcc gct gta gct gtg cct ttc gcc atg    48
Met Ala Met Gly Ser Ile Thr Ser Ala Val Ala Val Pro Phe Ala Met
```

```
                 1               5                  10                 15
caa gtg cag gcg agg ctt                                                              66
Gln Val Gln Ala Arg Leu
            20

<210> SEQ ID NO 13
<211> LENGTH: 22
<212> TYPE: PRT
<213> ORGANISM: Feline coronavirus

<400> SEQUENCE: 13

Met Ala Met Gly Ser Ile Thr Ser Ala Val Ala Val Pro Phe Ala Met
1               5                  10                 15

Gln Val Gln Ala Arg Leu
            20

<210> SEQ ID NO 14
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 14 atg gct atg ggt tct att aca tcc gct gta gct gtg cct ttc gcc atg            48
Met Ala Met Gly Ser Ile Thr Ser Ala Val Ala Val Pro Phe Ala Met
1               5                  10                 15 caa gtg cag gcg agg ctt                                                    66
Gln Val Gln Ala Arg Leu
            20

<210> SEQ ID NO 15
<211> LENGTH: 22
<212> TYPE: PRT
<213> ORGANISM: Feline coronavirus

<400> SEQUENCE: 15

Met Ala Met Gly Ser Ile Thr Ser Ala Val Ala Val Pro Phe Ala Met
1               5                  10                 15

Gln Val Gln Ala Arg Leu
            20

<210> SEQ ID NO 16
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 16 atg gcc atg gga tct att aca tct gct gta gct gtt cct ttc gcg atg            48
Met Ala Met Gly Ser Ile Thr Ser Ala Val Ala Val Pro Phe Ala Met
1               5                  10                 15 caa gtg cag gcc agg ctt                                                    66
Gln Val Gln Ala Arg Leu
            20

<210> SEQ ID NO 17
<211> LENGTH: 22
<212> TYPE: PRT
<213> ORGANISM: Feline coronavirus

<400> SEQUENCE: 17
```

```
Met Ala Met Gly Ser Ile Thr Ser Ala Val Ala Val Pro Phe Ala Met
1               5                   10                  15

Gln Val Gln Ala Arg Leu
            20

<210> SEQ ID NO 18
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 18 atg gct atg ggt tct att aca tct gct gta gct gtt cct ttt gct atg      48
Met Ala Met Gly Ser Ile Thr Ser Ala Val Ala Val Pro Phe Ala Met
1               5                   10                  15 caa gtg cag gct agg ctt                                              66
Gln Val Gln Ala Arg Leu
            20

<210> SEQ ID NO 19
<211> LENGTH: 22
<212> TYPE: PRT
<213> ORGANISM: Feline coronavirus

<400> SEQUENCE: 19

Met Ala Met Gly Ser Ile Thr Ser Ala Val Ala Val Pro Phe Ala Met
1               5                   10                  15

Gln Val Gln Ala Arg Leu
            20

<210> SEQ ID NO 20
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 20 atg gct atg ggt tct att aca tct gct gta gct gtt cct ttt gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 21
<211> LENGTH: 22
<212> TYPE: PRT
<213> ORGANISM: Feline coronavirus

<400> SEQUENCE: 21

Met Ala Met Gly Ser Ile Thr Ser Ala Val Ala Val Pro Phe Ala Met
1               5                   10                  15

Gln Val Gln Ala Arg Leu
            20

<210> SEQ ID NO 22
<211> LENGTH: 66
<212> TYPE: DNA
<213> ORGANISM: Feline coronavirus
<220> FEATURE:
```

-continued

```
<221> NAME/KEY: CDS
<222> LOCATION: (1)..(66)

<400> SEQUENCE: 22 atg gct atg ggt tct att aca tct gct gta gct gtt cct ttt gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 23
<211> LENGTH: 22
<212> TYPE: PRT
<213> ORGANISM: Feline coronavirus

<400> SEQUENCE: 23

Met Ala Met Gly Ser Ile Thr Ser Ala Val Ala Val Pro Phe Ala Met
1               5                   10                  15

Gln Val Gln Ala Arg Leu
            20

<210> SEQ ID NO 24
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 24 atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 25
<211> LENGTH: 22
<212> TYPE: PRT
<213> ORGANISM: Feline coronavirus

<400> SEQUENCE: 25

Met Ala Met Gly Ser Ile Thr Ser Ala Val Ala Val Pro Phe Ala Met
1               5                   10                  15

Gln Val Gln Ala Arg Leu
            20

<210> SEQ ID NO 26
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 26 atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20
```

-continued

```
<210> SEQ ID NO 27
<211> LENGTH: 22
<212> TYPE: PRT
<213> ORGANISM: Feline coronavirus

<400> SEQUENCE: 27

Met Ala Met Gly Ser Ile Thr Ser Ala Val Ala Val Pro Phe Ala Met
1               5                   10                  15

Gln Val Gln Ala Arg Leu
            20

<210> SEQ ID NO 28
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 28 atg gct atg ggt tct att act tct gct gta gct gtc ccc ttt gct atg      48
Met Ala Met Gly Ser Ile Thr Ser Ala Val Ala Val Pro Phe Ala Met
1               5                   10                  15 caa gtt cag gct agg ctt                                              66
Gln Val Gln Ala Arg Leu
            20

<210> SEQ ID NO 29
<211> LENGTH: 22
<212> TYPE: PRT
<213> ORGANISM: Feline coronavirus

<400> SEQUENCE: 29

Met Ala Met Gly Ser Ile Thr Ser Ala Val Ala Val Pro Phe Ala Met
1               5                   10                  15

Gln Val Gln Ala Arg Leu
            20

<210> SEQ ID NO 30
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 30 atg gct atg ggt tct att act tct gct gta gct gtc ccc ttt gcc atg      48
Met Ala Met Gly Ser Ile Thr Ser Ala Val Ala Val Pro Phe Ala Met
1               5                   10                  15 caa gtt cag gct agg ctt                                              66
Gln Val Gln Ala Arg Leu
            20

<210> SEQ ID NO 31
<211> LENGTH: 22
<212> TYPE: PRT
<213> ORGANISM: Feline coronavirus

<400> SEQUENCE: 31

Met Ala Met Gly Ser Ile Thr Ser Ala Val Ala Val Pro Phe Ala Met
1               5                   10                  15

Gln Val Gln Ala Arg Leu
            20
```

<210> SEQ ID NO 32
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 32

```
atg gct atg gga tcc att aca tct gct gtg gct gtt ccc ttc gcc atg    48
Met Ala Met Gly Ser Ile Thr Ser Ala Val Ala Val Pro Phe Ala Met
1               5                   10                  15 caa gtg cag gcc agg ctt                                            66
Gln Val Gln Ala Arg Leu
            20
```

<210> SEQ ID NO 33
<211> LENGTH: 22
<212> TYPE: PRT
<213> ORGANISM: Feline coronavirus

<400> SEQUENCE: 33

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 34
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 34

```
atg gcc atg ggc tct att aca tct act gta gcg gtc cca ttc gcc atg    48
Met Ala Met Gly Ser Ile Thr Ser Thr Val Ala Val Pro Phe Ala Met
1               5                   10                  15 caa gtg cag gct agg ctt                                            66
Gln Val Gln Ala Arg Leu
            20
```

<210> SEQ ID NO 35
<211> LENGTH: 22
<212> TYPE: PRT
<213> ORGANISM: Feline coronavirus

<400> SEQUENCE: 35

```
Met Ala Met Gly Ser Ile Thr Ser Thr Val Ala Val Pro Phe Ala Met
1               5                   10                  15

Gln Val Gln Ala Arg Leu
            20
```

<210> SEQ ID NO 36
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 36

```
atg gct atg ggc tct att aca tct gct gtg gct gtc cca ttc gcc atg    48
```

```
Met Ala Met Gly Ser Ile Thr Ser Ala Val Ala Val Pro Phe Ala Met
1               5                   10                  15 caa gtg caa gct agg ctt                                              66
Gln Val Gln Ala Arg Leu
            20
```

<210> SEQ ID NO 37
<211> LENGTH: 22
<212> TYPE: PRT
<213> ORGANISM: Feline coronavirus

<400> SEQUENCE: 37

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 38
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 38

```
atg gct atg ggc tct att aca tgt act gta gcc gtc cca ttt tct atg    48
Met Ala Met Gly Ser Ile Thr Cys Thr Val Ala Val Pro Phe Ser Met
1               5                   10                  15 caa gtg cag gcc ggg ctt                                              66
Gln Val Gln Ala Gly Leu
            20
```

<210> SEQ ID NO 39
<211> LENGTH: 22
<212> TYPE: PRT
<213> ORGANISM: Feline coronavirus

<400> SEQUENCE: 39

```
Met Ala Met Gly Ser Ile Thr Cys Thr Val Ala Val Pro Phe Ser Met
1               5                   10                  15

Gln Val Gln Ala Gly Leu
            20
```

<210> SEQ ID NO 40
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 40

```
atg gct atg ggc tct att aca tct gct gta gcc gtc cct ttt gct atg    48
Met Ala Met Gly Ser Ile Thr Ser Ala Val Ala Val Pro Phe Ala Met
1               5                   10                  15 caa gtg cag gct agg ctt                                              66
Gln Val Gln Ala Arg Leu
            20
```

<210> SEQ ID NO 41
<211> LENGTH: 22
<212> TYPE: PRT
<213> ORGANISM: Feline coronavirus

```
<400> SEQUENCE: 41

Met Ala Met Gly Ser Ile Thr Ser Ala Val Ala Val Pro Phe Ala Met
1               5                   10                  15

Gln Val Gln Ala Arg Leu
            20

<210> SEQ ID NO 42
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 42 atg gct atg ggt tct att aca tct gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 43
<211> LENGTH: 22
<212> TYPE: PRT
<213> ORGANISM: Feline coronavirus

<400> SEQUENCE: 43

Met Ala Met Gly Ser Ile Thr Ser Ala Val Ala Val Pro Phe Ala Met
1               5                   10                  15

Gln Val Gln Ala Arg Leu
            20

<210> SEQ ID NO 44
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 44 atg gcc atg ggt tct att aca tct gct gtg gct gta cct ttc gct atg      48
Met Ala Met Gly Ser Ile Thr Ser Ala Val Ala Val Pro Phe Ala Met
1               5                   10                  15 caa gtg cag gcc agg ctt                                              66
Gln Val Gln Ala Arg Leu
            20

<210> SEQ ID NO 45
<211> LENGTH: 22
<212> TYPE: PRT
<213> ORGANISM: Feline coronavirus

<400> SEQUENCE: 45

Met Ala Met Gly Ser Ile Thr Ser Ala Val Ala Val Pro Phe Ala Met
1               5                   10                  15

Gln Val Gln Ala Arg Leu
            20

<210> SEQ ID NO 46
<211> LENGTH: 66
<212> TYPE: DNA
<213> ORGANISM: Feline coronavirus
```

```
<220> FEATURE:
<221> NAME/KEY: CDS
<222> LOCATION: (1)..(66)

<400> SEQUENCE: 46 atg gct atg ggc tct att aca tct gct gtg gct gtg cct ttt gct atg      48
Met Ala Met Gly Ser Ile Thr Ser Ala Val Ala Val Pro Phe Ala Met
1               5                   10                  15 caa gta cag gct agg ctc                                              66
Gln Val Gln Ala Arg Leu
            20

<210> SEQ ID NO 47
<211> LENGTH: 22
<212> TYPE: PRT
<213> ORGANISM: Feline coronavirus

<400> SEQUENCE: 47

Met Ala Met Gly Ser Ile Thr Ser Ala Val Ala Val Pro Phe Ala Met
1               5                   10                  15

Gln Val Gln Ala Arg Leu
            20

<210> SEQ ID NO 48
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 48 atg gct atg ggc tct att aca tct gct gtg gct gtg cct ttt gct atg      48
Met Ala Met Gly Ser Ile Thr Ser Ala Val Ala Val Pro Phe Ala Met
1               5                   10                  15 caa gtg cag gct agg ctc                                              66
Gln Val Gln Ala Arg Leu
            20

<210> SEQ ID NO 49
<211> LENGTH: 22
<212> TYPE: PRT
<213> ORGANISM: Feline coronavirus

<400> SEQUENCE: 49

Met Ala Met Gly Ser Ile Thr Ser Ala Val Ala Val Pro Phe Ala Met
1               5                   10                  15

Gln Val Gln Ala Arg Leu
            20

<210> SEQ ID NO 50
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 50 atg gct atg ggc tct att aca tct gct gtg gct gtg cct ttt gct atg      48
Met Ala Met Gly Ser Ile Thr Ser Ala Val Ala Val Pro Phe Ala Met
1               5                   10                  15 caa gta cag gct agg ctc                                              66
Gln Val Gln Ala Arg Leu
            20
```

<210> SEQ ID NO 51
<211> LENGTH: 22
<212> TYPE: PRT
<213> ORGANISM: Feline coronavirus

<400> SEQUENCE: 51

Met Ala Met Gly Ser Ile Thr Ser Ala Val Ala Val Pro Phe Ala Met
1               5                   10                  15

Gln Val Gln Ala Arg Leu
            20

<210> SEQ ID NO 52
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 52 atg gct atg ggc tct att aca tct gct gtg gct gtg cct ttt gct atg      48
Met Ala Met Gly Ser Ile Thr Ser Ala Val Ala Val Pro Phe Ala Met
1               5                   10                  15 caa gta cag gct agg ctc                                              66
Gln Val Gln Ala Arg Leu
            20

<210> SEQ ID NO 53
<211> LENGTH: 22
<212> TYPE: PRT
<213> ORGANISM: Feline coronavirus

<400> SEQUENCE: 53

Met Ala Met Gly Ser Ile Thr Ser Ala Val Ala Val Pro Phe Ala Met
1               5                   10                  15

Gln Val Gln Ala Arg Leu
            20

<210> SEQ ID NO 54
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 54 atg gct atg ggc tct att act tca act gta gct gtc ccc ttt gct atg      48
Met Ala Met Gly Ser Ile Thr Ser Thr Val Ala Val Pro Phe Ala Met
1               5                   10                  15 caa gta cag gct aga ctt                                              66
Gln Val Gln Ala Arg Leu
            20

<210> SEQ ID NO 55
<211> LENGTH: 22
<212> TYPE: PRT
<213> ORGANISM: Feline coronavirus

<400> SEQUENCE: 55

Met Ala Met Gly Ser Ile Thr Ser Thr Val Ala Val Pro Phe Ala Met
1               5                   10                  15

Gln Val Gln Ala Arg Leu

<210> SEQ ID NO 56
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 56

```
atg gct atg ggc tct att act tca gct gta gct gtc ccc ttt gct atg      48
Met Ala Met Gly Ser Ile Thr Ser Ala Val Ala Val Pro Phe Ala Met
1               5                   10                  15 caa gta cag gct aga ctt                                              66
Gln Val Gln Ala Arg Leu
            20
```

<210> SEQ ID NO 57
<211> LENGTH: 22
<212> TYPE: PRT
<213> ORGANISM: Feline coronavirus

<400> SEQUENCE: 57

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 58
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 58

```
atg gct atg ggc tct att acg tca gct gta gct gtc ccc ttt gct atg      48
Met Ala Met Gly Ser Ile Thr Ser Ala Val Ala Val Pro Phe Ala Met
1               5                   10                  15 caa gta cag gct aga ctt                                              66
Gln Val Gln Ala Arg Leu
            20
```

<210> SEQ ID NO 59
<211> LENGTH: 22
<212> TYPE: PRT
<213> ORGANISM: Feline coronavirus

<400> SEQUENCE: 59

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 60
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 60

```
atg gct atg ggc tct att act tca act gta gct gtc ccc ttt gct atg    48
Met Ala Met Gly Ser Ile Thr Ser Thr Val Ala Val Pro Phe Ala Met
1               5                   10                  15 caa gta cag gct aga ctt                                             66
Gln Val Gln Ala Arg Leu
            20
```

<210> SEQ ID NO 61
<211> LENGTH: 22
<212> TYPE: PRT
<213> ORGANISM: Feline coronavirus

<400> SEQUENCE: 61

```
Met Ala Met Gly Ser Ile Thr Ser Thr Val Ala Val Pro Phe Ala Met
1               5                   10                  15

Gln Val Gln Ala Arg Leu
            20
```

<210> SEQ ID NO 62
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 62

```
atg gct atg ggc tct att act tca gct gta gct gtc ccc ttt gct atg    48
Met Ala Met Gly Ser Ile Thr Ser Ala Val Ala Val Pro Phe Ala Met
1               5                   10                  15 caa gta cag gct aga ctt                                             66
Gln Val Gln Ala Arg Leu
            20
```

<210> SEQ ID NO 63
<211> LENGTH: 22
<212> TYPE: PRT
<213> ORGANISM: Feline coronavirus

<400> SEQUENCE: 63

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 64
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 64

```
atg gcc atg ggt tcc att act tcg tct gta gcc gtt cct ttt gcc atg    48
Met Ala Met Gly Ser Ile Thr Ser Ser Val Ala Val Pro Phe Ala Met
1               5                   10                  15 caa gtg cag gcc agg ctt                                             66
Gln Val Gln Ala Arg Leu
            20
```

<210> SEQ ID NO 65
<211> LENGTH: 22
<212> TYPE: PRT
<213> ORGANISM: Feline coronavirus

```
<400> SEQUENCE: 65

Met Ala Met Gly Ser Ile Thr Ser Ser Val Ala Val Pro Phe Ala Met
1               5                   10                  15

Gln Val Gln Ala Arg Leu
            20

<210> SEQ ID NO 66
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 66 atg gcc atg ggt tcc att act tcg tct gta gcc gtt cct ttt gcc atg      48
Met Ala Met Gly Ser Ile Thr Ser Ser Val Ala Val Pro Phe Ala Met
1               5                   10                  15 caa gtg cag gcc agg ctt                                               66
Gln Val Gln Ala Arg Leu
            20

<210> SEQ ID NO 67
<211> LENGTH: 22
<212> TYPE: PRT
<213> ORGANISM: Feline coronavirus

<400> SEQUENCE: 67

Met Ala Met Gly Ser Ile Thr Ser Ser Val Ala Val Pro Phe Ala Met
1               5                   10                  15

Gln Val Gln Ala Arg Leu
            20

<210> SEQ ID NO 68
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 68 atg gct atg ggt tct att acg tct gct gta gct gtt cct ttt gct atg      48
Met Ala Met Gly Ser Ile Thr Ser Ala Val Ala Val Pro Phe Ala Met
1               5                   10                  15 caa gtg cag gcg agg ctt                                               66
Gln Val Gln Ala Arg Leu
            20

<210> SEQ ID NO 69
<211> LENGTH: 22
<212> TYPE: PRT
<213> ORGANISM: Feline coronavirus

<400> SEQUENCE: 69

Met Ala Met Gly Ser Ile Thr Ser Ala Val Ala Val Pro Phe Ala Met
1               5                   10                  15

Gln Val Gln Ala Arg Leu
            20

<210> SEQ ID NO 70
<211> LENGTH: 66
<212> TYPE: DNA
```

<210> SEQ ID NO 70
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 70

```
atg gct atg ggt tct att aca tct gct gtg gct gtt cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20
```

<210> SEQ ID NO 71
<211> LENGTH: 22
<212> TYPE: PRT
<213> ORGANISM: Feline coronavirus

<400> SEQUENCE: 71

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 72
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 72

```
atg gct atg ggt tct att aca tct gct gtg gct gtt cct ttc gcc atg      48
Met Ala Met Gly Ser Ile Thr Ser Ala Val Ala Val Pro Phe Ala Met
1               5                   10                  15 caa gtg caa gct aga ctt                                              66
Gln Val Gln Ala Arg Leu
            20
```

<210> SEQ ID NO 73
<211> LENGTH: 22
<212> TYPE: PRT
<213> ORGANISM: Feline coronavirus

<400> SEQUENCE: 73

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 74
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 74

```
atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
```

<210> SEQ ID NO 75
<211> LENGTH: 22
<212> TYPE: PRT
<213> ORGANISM: Feline coronavirus

<400> SEQUENCE: 75

Met Ala Met Gly Ser Ile Thr Ser Ala Val Ala Val Pro Phe Ala Met
1               5                   10                  15

Gln Val Gln Ala Arg Leu
            20

<210> SEQ ID NO 76
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 76 atg gct atg ggt tct att aca tcc gct gta gct gtg cct ttc gcc atg    48
Met Ala Met Gly Ser Ile Thr Ser Ala Val Ala Val Pro Phe Ala Met
1               5                   10                  15 caa gtg cag gcg agg ctt                                             66
Gln Val Gln Ala Arg Leu
            20

<210> SEQ ID NO 77
<211> LENGTH: 22
<212> TYPE: PRT
<213> ORGANISM: Feline coronavirus

<400> SEQUENCE: 77

Met Ala Met Gly Ser Ile Thr Ser Ala Val Ala Val Pro Phe Ala Met
1               5                   10                  15

Gln Val Gln Ala Arg Leu
            20

<210> SEQ ID NO 78
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 78 atg gct atg ggt tct att aca tcc gct gta gct gtg cct ttc gcc atg    48
Met Ala Met Gly Ser Ile Thr Ser Ala Val Ala Val Pro Phe Ala Met
1               5                   10                  15 caa gtg cag gcg agg ctt                                             66
Gln Val Gln Ala Arg Leu
            20

<210> SEQ ID NO 79
<211> LENGTH: 22
<212> TYPE: PRT
<213> ORGANISM: Feline coronavirus

<400> SEQUENCE: 79

Met Ala Met Gly Ser Ile Thr Ser Ala Val Ala Val Pro Phe Ala Met
1               5                   10                  15

Gln Val Gln Ala Arg Leu
            20

<210> SEQ ID NO 80
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 80 atg gct atg ggc gct att aca tct gct gtg gct gtt cct ttc gct atg      48
Met Ala Met Gly Ala Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 81
<211> LENGTH: 22
<212> TYPE: PRT
<213> ORGANISM: Feline coronavirus

<400> SEQUENCE: 81

Met Ala Met Gly Ala Ile Thr Ser Ala Val Ala Val Pro Phe Ala Met
1               5                   10                  15

Gln Val Gln Ala Arg Leu
            20

<210> SEQ ID NO 82
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 82 atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 83
<211> LENGTH: 22
<212> TYPE: PRT
<213> ORGANISM: Feline coronavirus

<400> SEQUENCE: 83

Met Ala Met Gly Ser Ile Thr Ser Ala Val Ala Val Pro Phe Ala Met
1               5                   10                  15

Gln Val Gln Ala Arg Leu
            20

<210> SEQ ID NO 84
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 84

```
atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20
```

<210> SEQ ID NO 85
<211> LENGTH: 22
<212> TYPE: PRT
<213> ORGANISM: Feline coronavirus

<400> SEQUENCE: 85

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 86
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 86

```
atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20
```

<210> SEQ ID NO 87
<211> LENGTH: 22
<212> TYPE: PRT
<213> ORGANISM: Feline coronavirus

<400> SEQUENCE: 87

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 88
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 88

```
atg gct atg ggt tct att aca tcc gct gta gct gtg cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20
```

<210> SEQ ID NO 89
<211> LENGTH: 22
<212> TYPE: PRT

-continued

<213> ORGANISM: Feline coronavirus

<400> SEQUENCE: 89

Met Ala Met Gly Ser Ile Thr Ser Ala Val Ala Val Pro Phe Ala Met
1               5                   10                  15

Gln Val Gln Ala Arg Leu
            20

<210> SEQ ID NO 90
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 90 atg gct atg ggt tct att aca tcc gct gta gct gtg cct ttc gcc atg    48
Met Ala Met Gly Ser Ile Thr Ser Ala Val Ala Val Pro Phe Ala Met
1               5                   10                  15 caa gtg cag gcg agg ctt                                             66
Gln Val Gln Ala Arg Leu
            20

<210> SEQ ID NO 91
<211> LENGTH: 22
<212> TYPE: PRT
<213> ORGANISM: Feline coronavirus

<400> SEQUENCE: 91

Met Ala Met Gly Ser Ile Thr Ser Ala Val Ala Val Pro Phe Ala Met
1               5                   10                  15

Gln Val Gln Ala Arg Leu
            20

<210> SEQ ID NO 92
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 92 atg gct atg ggt tct ata cat ctg ctg tgg ctg ttc ctt tcg cca tgc    48
Met Ala Met Gly Ser Ile His Leu Leu Trp Leu Phe Leu Ser Pro Cys
1               5                   10                  15 aag tgc agg cga ggc tta                                             66
Lys Cys Arg Arg Gly Leu
            20

<210> SEQ ID NO 93
<211> LENGTH: 22
<212> TYPE: PRT
<213> ORGANISM: Feline coronavirus

<400> SEQUENCE: 93

Met Ala Met Gly Ser Ile His Leu Leu Trp Leu Phe Leu Ser Pro Cys
1               5                   10                  15

Lys Cys Arg Arg Gly Leu
            20

<210> SEQ ID NO 94
<211> LENGTH: 66

```
<212> TYPE: DNA
<213> ORGANISM: Feline coronavirus
<220> FEATURE:
<221> NAME/KEY: CDS
<222> LOCATION: (1)..(66)

<400> SEQUENCE: 94 atg gct atg ggc gct att aca tct gct gtg gct gtg cct ttc gct atg     48
Met Ala Met Gly Ala Ile Thr Ser Ala Val Ala Val Pro Phe Ala Met
 1               5                  10                  15 caa gtg cag gcg agg ctt                                              66
Gln Val Gln Ala Arg Leu
             20

<210> SEQ ID NO 95
<211> LENGTH: 22
<212> TYPE: PRT
<213> ORGANISM: Feline coronavirus

<400> SEQUENCE: 95

Met Ala Met Gly Ala Ile Thr Ser Ala Val Ala Val Pro Phe Ala Met
 1               5                  10                  15

Gln Val Gln Ala Arg Leu
             20

<210> SEQ ID NO 96
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 96 atg gct atg ggt tct att aca tct gct gta gct gtt cct ttt gct atg     48
Met Ala Met Gly Ser Ile Thr Ser Ala Val Ala Val Pro Phe Ala Met
 1               5                  10                  15 caa gtg cag gcg agg ctt                                              66
Gln Val Gln Ala Arg Leu
             20

<210> SEQ ID NO 97
<211> LENGTH: 22
<212> TYPE: PRT
<213> ORGANISM: Feline coronavirus

<400> SEQUENCE: 97

Met Ala Met Gly Ser Ile Thr Ser Ala Val Ala Val Pro Phe Ala Met
 1               5                  10                  15

Gln Val Gln Ala Arg Leu
             20

<210> SEQ ID NO 98
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 98 atg gcc atg ggt tcc att act tcg tct gta gcc gtt cct ttt gcc atg     48
Met Ala Met Gly Ser Ile Thr Ser Ser Val Ala Val Pro Phe Ala Met
 1               5                  10                  15 caa gtg cag gcc agg ctt                                              66
```

Gln Val Gln Ala Arg Leu
        20

<210> SEQ ID NO 99
<211> LENGTH: 22
<212> TYPE: PRT
<213> ORGANISM: Feline coronavirus

<400> SEQUENCE: 99

Met Ala Met Gly Ser Ile Thr Ser Ser Val Ala Val Pro Phe Ala Met
1               5                   10                  15

Gln Val Gln Ala Arg Leu
        20

<210> SEQ ID NO 100
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 100 atg gct atg ggt tct att aca tca gct gtg gca gtc cct ttt gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
        20

<210> SEQ ID NO 101
<211> LENGTH: 22
<212> TYPE: PRT
<213> ORGANISM: Feline coronavirus

<400> SEQUENCE: 101

Met Ala Met Gly Ser Ile Thr Ser Ala Val Ala Val Pro Phe Ala Met
1               5                   10                  15

Gln Val Gln Ala Arg Leu
        20

<210> SEQ ID NO 102
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 102 atg gcc atg gga tct att aca tct gct gta gct gtt cct ttc gct atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
        20

<210> SEQ ID NO 103
<211> LENGTH: 22
<212> TYPE: PRT
<213> ORGANISM: Feline coronavirus

<400> SEQUENCE: 103

Met Ala Met Gly Ser Ile Thr Ser Ala Val Ala Val Pro Phe Ala Met
1               5                   10                  15

Gln Val Gln Ala Arg Leu
            20

<210> SEQ ID NO 104
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 104 atg gcc ttg ggc tct att aca tct gct gta gct gtc cca ttc gcc atg    48
Met Ala Leu Gly Ser Ile Thr Ser Ala Val Ala Val Pro Phe Ala Met
1               5                   10                  15 caa gtg cag gct agg ctt                                             66
Gln Val Gln Ala Arg Leu
            20

<210> SEQ ID NO 105
<211> LENGTH: 22
<212> TYPE: PRT
<213> ORGANISM: Feline coronavirus

<400> SEQUENCE: 105

Met Ala Leu Gly Ser Ile Thr Ser Ala Val Ala Val Pro Phe Ala Met
1               5                   10                  15

Gln Val Gln Ala Arg Leu
            20

<210> SEQ ID NO 106
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 106 atg gct ttk ggt tct att act tcc gca gta gcc gta cct ttt gcc atg    48
Met Ala Xaa Gly Ser Ile Thr Ser Ala Val Ala Val Pro Phe Ala Met
1               5                   10                  15 caa gta cag gct aga ctt                                             66
Gln Val Gln Ala Arg Leu
            20

<210> SEQ ID NO 107
<211> LENGTH: 22
<212> TYPE: PRT
<213> ORGANISM: Feline coronavirus
<220> FEATURE:
<221> NAME/KEY: misc_feature
<222> LOCATION: (3)..(3)
<223> OTHER INFORMATION: The 'Xaa' at location 3 stands for Leu, or Phe.

<400> SEQUENCE: 107

Met Ala Xaa Gly Ser Ile Thr Ser Ala Val Ala Val Pro Phe Ala Met
1               5                   10                  15

Gln Val Gln Ala Arg Leu
            20

<210> SEQ ID NO 108
<211> LENGTH: 66
<212> TYPE: DNA
<213> ORGANISM: Feline coronavirus

```
<220> FEATURE:
<221> NAME/KEY: CDS
<222> LOCATION: (1)..(66)

<400> SEQUENCE: 108 atg gcc ttg ggc tct att aca tct gct gtg gcc gta cct ttc gcc atg      48
Met Ala Leu Gly Ser Ile Thr Ser Ala Val Ala Val Pro Phe Ala Met
1               5                   10                  15 caa gtg cag gct agg cty                                              66
Gln Val Gln Ala Arg Xaa
            20

<210> SEQ ID NO 109
<211> LENGTH: 22
<212> TYPE: PRT
<213> ORGANISM: Feline coronavirus
<220> FEATURE:
<221> NAME/KEY: misc_feature
<222> LOCATION: (22)..(22)
<223> OTHER INFORMATION: The 'Xaa' at location 22 stands for Leu.

<400> SEQUENCE: 109

Met Ala Leu Gly Ser Ile Thr Ser Ala Val Ala Val Pro Phe Ala Met
1               5                   10                  15

Gln Val Gln Ala Arg Xaa
            20

<210> SEQ ID NO 110
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 110 atg gct ttg ggc tct att act tct gct gtt gca gtt ccc ttc gcc atg      48
Met Ala Leu Gly Ser Ile Thr Ser Ala Val Ala Val Pro Phe Ala Met
1               5                   10                  15 caa gtg caa gct agg ctt                                              66
Gln Val Gln Ala Arg Leu
            20

<210> SEQ ID NO 111
<211> LENGTH: 22
<212> TYPE: PRT
<213> ORGANISM: Feline coronavirus

<400> SEQUENCE: 111

Met Ala Leu Gly Ser Ile Thr Ser Ala Val Ala Val Pro Phe Ala Met
1               5                   10                  15

Gln Val Gln Ala Arg Leu
            20

<210> SEQ ID NO 112
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 112 atg gct ttg ggt tct att aca tcc gct gta gct gtg cct ttc gcc atg      48
Met Ala Leu Gly Ser Ile Thr Ser Ala Val Ala Val Pro Phe Ala Met
1               5                   10                  15
```

```
caa gtg cag gcg agg ctt                                                66
Gln Val Gln Ala Arg Leu
         20

<210> SEQ ID NO 113
<211> LENGTH: 22
<212> TYPE: PRT
<213> ORGANISM: Feline coronavirus

<400> SEQUENCE: 113

Met Ala Leu Gly Ser Ile Thr Ser Ala Val Ala Val Pro Phe Ala Met
1               5                   10                  15

Gln Val Gln Ala Arg Leu
         20

<210> SEQ ID NO 114
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 114 atg gct ttg ggc tct att aca tct gct gta gcc gtc cct ttt gct atg    48
Met Ala Leu Gly Ser Ile Thr Ser Ala Val Ala Val Pro Phe Ala Met
1               5                   10                  15 caa gtg cag gcg agg ctt                                            66
Gln Val Gln Ala Arg Leu
         20

<210> SEQ ID NO 115
<211> LENGTH: 22
<212> TYPE: PRT
<213> ORGANISM: Feline coronavirus

<400> SEQUENCE: 115

Met Ala Leu Gly Ser Ile Thr Ser Ala Val Ala Val Pro Phe Ala Met
1               5                   10                  15

Gln Val Gln Ala Arg Leu
         20

<210> SEQ ID NO 116
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 116 atg gct ttg ggt tct att aca tct gct gtg gct gtc cct ttt tcc atg    48
Met Ala Leu Gly Ser Ile Thr Ser Ala Val Ala Val Pro Phe Ser Met
1               5                   10                  15 caa gtg caa gcc aga ctt                                            66
Gln Val Gln Ala Arg Leu
         20

<210> SEQ ID NO 117
<211> LENGTH: 22
<212> TYPE: PRT
<213> ORGANISM: Feline coronavirus

<400> SEQUENCE: 117
```

```
Met Ala Leu Gly Ser Ile Thr Ser Ala Val Ala Val Pro Phe Ser Met
1               5                   10                  15

Gln Val Gln Ala Arg Leu
            20

<210> SEQ ID NO 118
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 118 atg gct ttg ggc tct atc aca tct gct gta gct gtt cct ttt gct atg      48
Met Ala Leu Gly Ser Ile Thr Ser Ala Val Ala Val Pro Phe Ala Met
1               5                   10                  15 caa gta cag gca aga ctt                                              66
Gln Val Gln Ala Arg Leu
            20

<210> SEQ ID NO 119
<211> LENGTH: 22
<212> TYPE: PRT
<213> ORGANISM: Feline coronavirus

<400> SEQUENCE: 119

Met Ala Leu Gly Ser Ile Thr Ser Ala Val Ala Val Pro Phe Ala Met
1               5                   10                  15

Gln Val Gln Ala Arg Leu
            20

<210> SEQ ID NO 120
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 120 atg gcc ttg ggt tct att aca tct gct gtg gcc gta cct ttc gcc atg      48
Met Ala Leu Gly Ser Ile Thr Ser Ala Val Ala Val Pro Phe Ala Met
1               5                   10                  15 caa gtg cag gct agg ctc                                              66
Gln Val Gln Ala Arg Leu
            20

<210> SEQ ID NO 121
<211> LENGTH: 22
<212> TYPE: PRT
<213> ORGANISM: Feline coronavirus

<400> SEQUENCE: 121

Met Ala Leu Gly Ser Ile Thr Ser Ala Val Ala Val Pro Phe Ala Met
1               5                   10                  15

Gln Val Gln Ala Arg Leu
            20

<210> SEQ ID NO 122
<211> LENGTH: 66
<212> TYPE: DNA
<213> ORGANISM: Feline coronavirus
<220> FEATURE:
<221> NAME/KEY: CDS
```

```
<222> LOCATION: (1)..(66)

<400> SEQUENCE: 122 atg gct ttg ggt tct att aca tca gct gta gct gtt ccc ttt gct atg      48
Met Ala Leu Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 123
<211> LENGTH: 22
<212> TYPE: PRT
<213> ORGANISM: Feline coronavirus

<400> SEQUENCE: 123

Met Ala Leu Gly Ser Ile Thr Ser Ala Val Ala Val Pro Phe Ala Met
1               5                   10                  15

Gln Val Gln Ala Arg Leu
            20

<210> SEQ ID NO 124
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 124 atg gct ttg ggt tcc att acc tca gct gta gct gtt ccc ttt gct atg      48
Met Ala Leu Gly Ser Ile Thr Ser Ala Val Ala Val Pro Phe Ala Met
1               5                   10                  15 caa gta cag gct aga ctt                                              66
Gln Val Gln Ala Arg Leu
            20

<210> SEQ ID NO 125
<211> LENGTH: 22
<212> TYPE: PRT
<213> ORGANISM: Feline coronavirus

<400> SEQUENCE: 125

Met Ala Leu Gly Ser Ile Thr Ser Ala Val Ala Val Pro Phe Ala Met
1               5                   10                  15

Gln Val Gln Ala Arg Leu
            20

<210> SEQ ID NO 126
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 126 atg gct ttg ggt tct att act tct gct gtt gct gtc ccc ttt gcc atg      48
Met Ala Leu Gly Ser Ile Thr Ser Ala Val Ala Val Pro Phe Ala Met
1               5                   10                  15 caa gtt cag gct agg ctt                                              66
Gln Val Gln Ala Arg Leu
            20
```

<210> SEQ ID NO 127
<211> LENGTH: 22
<212> TYPE: PRT
<213> ORGANISM: Feline coronavirus

<400> SEQUENCE: 127

Met Ala Leu Gly Ser Ile Thr Ser Ala Val Ala Val Pro Phe Ala Met
1               5                   10                  15

Gln Val Gln Ala Arg Leu
            20

<210> SEQ ID NO 128
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 128 atg gct ttg ggt tct att act tca gct gtc gcc gtg cct ttt tct atg      48
Met Ala Leu Gly Ser Ile Thr Ser Ala Val Ala Val Pro Phe Ser Met
1               5                   10                  15 caa gta cag gcc aga ctt                                              66
Gln Val Gln Ala Arg Leu
            20

<210> SEQ ID NO 129
<211> LENGTH: 22
<212> TYPE: PRT
<213> ORGANISM: Feline coronavirus

<400> SEQUENCE: 129

Met Ala Leu Gly Ser Ile Thr Ser Ala Val Ala Val Pro Phe Ser Met
1               5                   10                  15

Gln Val Gln Ala Arg Leu
            20

<210> SEQ ID NO 130
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 130 atg gct ttg ggt tct atc act tct gct gtg gct gtt cct ttc gcc atg      48
Met Ala Leu Gly Ser Ile Thr Ser Ala Val Ala Val Pro Phe Ala Met
1               5                   10                  15 caa gtg caa gct agg ctt                                              66
Gln Val Gln Ala Arg Leu
            20

<210> SEQ ID NO 131
<211> LENGTH: 22
<212> TYPE: PRT
<213> ORGANISM: Feline coronavirus

<400> SEQUENCE: 131

Met Ala Leu Gly Ser Ile Thr Ser Ala Val Ala Val Pro Phe Ala Met
1               5                   10                  15

Gln Val Gln Ala Arg Leu
            20

<210> SEQ ID NO 132
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 132

```
atg gct ttg ggc tct att aca tct gct gta gca gtc ccc ttt tcc atg       48
Met Ala Leu Gly Ser Ile Thr Ser Ala Val Ala Val Pro Phe Ser Met
1               5                   10                  15 caa gtg caa gca agg ctt                                               66
Gln Val Gln Ala Arg Leu
            20
```

<210> SEQ ID NO 133
<211> LENGTH: 22
<212> TYPE: PRT
<213> ORGANISM: Feline coronavirus

<400> SEQUENCE: 133

Met Ala Leu Gly Ser Ile Thr Ser Ala Val Ala Val Pro Phe Ser Met
1               5                   10                  15

Gln Val Gln Ala Arg Leu
            20

<210> SEQ ID NO 134
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 134

```
atg gct ttg ggt tct att aca tct gct gtg gct gtc ccg ttc gcc atg       48
Met Ala Leu Gly Ser Ile Thr Ser Ala Val Ala Val Pro Phe Ala Met
1               5                   10                  15 caa gtg caa gct agg ctt                                               66
Gln Val Gln Ala Arg Leu
            20
```

<210> SEQ ID NO 135
<211> LENGTH: 22
<212> TYPE: PRT
<213> ORGANISM: Feline coronavirus

<400> SEQUENCE: 135

Met Ala Leu Gly Ser Ile Thr Ser Ala Val Ala Val Pro Phe Ala Met
1               5                   10                  15

Gln Val Gln Ala Arg Leu
            20

<210> SEQ ID NO 136
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 136

```
atg gcc ttg ggg tct atc aca tcg gcc gta gct gtc cct ttc tcc atg       48
Met Ala Leu Gly Ser Ile Thr Ser Ala Val Ala Val Pro Phe Ser Met
```

-continued

```
                1               5                  10                 15
caa gtg caa gct agg cta                                                              66
Gln Val Gln Ala Arg Leu
            20

<210> SEQ ID NO 137
<211> LENGTH: 22
<212> TYPE: PRT
<213> ORGANISM: Feline coronavirus

<400> SEQUENCE: 137

Met Ala Leu Gly Ser Ile Thr Ser Ala Val Ala Val Pro Phe Ser Met
1               5                   10                  15

Gln Val Gln Ala Arg Leu
            20

<210> SEQ ID NO 138
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 138 atg gct ttg ggc tct att aca tct gct gtg gca gtt ccc ttc gcc atg     48
Met Ala Leu Gly Ser Ile Thr Ser Ala Val Ala Val Pro Phe Ala Met
1               5                   10                  15 caa gtg cag gct agg ctt                                              66
Gln Val Gln Ala Arg Leu
            20

<210> SEQ ID NO 139
<211> LENGTH: 22
<212> TYPE: PRT
<213> ORGANISM: Feline coronavirus

<400> SEQUENCE: 139

Met Ala Leu Gly Ser Ile Thr Ser Ala Val Ala Val Pro Phe Ala Met
1               5                   10                  15

Gln Val Gln Ala Arg Leu
            20

<210> SEQ ID NO 140
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 140 atg gct ttg ggt tct att act tct gct gta gct gtc ccc ttt gcc atg     48
Met Ala Leu Gly Ser Ile Thr Ser Ala Val Ala Val Pro Phe Ala Met
1               5                   10                  15 caa gtt cag gct agg ctt                                              66
Gln Val Gln Ala Arg Leu
            20

<210> SEQ ID NO 141
<211> LENGTH: 22
<212> TYPE: PRT
<213> ORGANISM: Feline coronavirus

<400> SEQUENCE: 141
```

```
Met Ala Leu Gly Ser Ile Thr Ser Ala Val Ala Val Pro Phe Ala Met
1               5                   10                  15

Gln Val Gln Ala Arg Leu
            20

<210> SEQ ID NO 142
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 142 atg gct ctg ggt tct att act tca gct gtc gcc gtg cct ttt gct atg      48
Met Ala Leu Gly Ser Ile Thr Ser Ala Val Ala Val Pro Phe Ala Met
1               5                   10                  15 caa gta cag gct aga ctt                                              66
Gln Val Gln Ala Arg Leu
            20

<210> SEQ ID NO 143
<211> LENGTH: 22
<212> TYPE: PRT
<213> ORGANISM: Feline coronavirus

<400> SEQUENCE: 143

Met Ala Leu Gly Ser Ile Thr Ser Ala Val Ala Val Pro Phe Ala Met
1               5                   10                  15

Gln Val Gln Ala Arg Leu
            20

<210> SEQ ID NO 144
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 144 atg gct ttg ggt tct att aca tcc gct gta gct gtg cct ttc gcc atg      48
Met Ala Leu Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 145
<211> LENGTH: 22
<212> TYPE: PRT
<213> ORGANISM: Feline coronavirus

<400> SEQUENCE: 145

Met Ala Leu Gly Ser Ile Thr Ser Ala Val Ala Val Pro Phe Ala Met
1               5                   10                  15

Gln Val Gln Ala Arg Leu
            20

<210> SEQ ID NO 146
<211> LENGTH: 66
<212> TYPE: DNA
<213> ORGANISM: Feline coronavirus
<220> FEATURE:
```

```
<221> NAME/KEY: CDS
<222> LOCATION: (1)..(66)

<400> SEQUENCE: 146 atg gcc ctg ggt tct att aca tct gct gtg gct gta cct ttt gct atg      48
Met Ala Leu Gly Ser Ile Thr Ser Ala Val Ala Val Pro Phe Ala Met
1               5                   10                  15 caa gtg cag gcc agg ctt                                              66
Gln Val Gln Ala Arg Leu
            20

<210> SEQ ID NO 147
<211> LENGTH: 22
<212> TYPE: PRT
<213> ORGANISM: Feline coronavirus

<400> SEQUENCE: 147

Met Ala Leu Gly Ser Ile Thr Ser Ala Val Ala Val Pro Phe Ala Met
1               5                   10                  15

Gln Val Gln Ala Arg Leu
            20

<210> SEQ ID NO 148
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 148 atg gct ttg gga tct atc aca tca gct gta gcc gtg cct ttt gct atg      48
Met Ala Leu Gly Ser Ile Thr Ser Ala Val Ala Val Pro Phe Ala Met
1               5                   10                  15 caa gtg cag gct agg ctt                                              66
Gln Val Gln Ala Arg Leu
            20

<210> SEQ ID NO 149
<211> LENGTH: 22
<212> TYPE: PRT
<213> ORGANISM: Feline coronavirus

<400> SEQUENCE: 149

Met Ala Leu Gly Ser Ile Thr Ser Ala Val Ala Val Pro Phe Ala Met
1               5                   10                  15

Gln Val Gln Ala Arg Leu
            20

<210> SEQ ID NO 150
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 150 atg gcc ttg gga tct atc aca tca gcg gta gct gtc cct ttt gcc atg      48
Met Ala Leu Gly Ser Ile Thr Ser Ala Val Ala Val Pro Phe Ala Met
1               5                   10                  15 caa gtg cag gcg agg ctt                                              66
Gln Val Gln Ala Arg Leu
            20
```

<210> SEQ ID NO 151
<211> LENGTH: 22
<212> TYPE: PRT
<213> ORGANISM: Feline coronavirus

<400> SEQUENCE: 151

Met Ala Leu Gly Ser Ile Thr Ser Ala Val Ala Val Pro Phe Ala Met
1               5                   10                  15

Gln Val Gln Ala Arg Leu
            20

<210> SEQ ID NO 152
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 152 atg gct ttg ggc tct att aca tct gct gta gca gtt ccc ttc gcc atg    48
Met Ala Leu Gly Ser Ile Thr Ser Ala Val Ala Val Pro Phe Ala Met
1               5                   10                  15 caa gtg cag gcg agg ctt                                            66
Gln Val Gln Ala Arg Leu
            20

<210> SEQ ID NO 153
<211> LENGTH: 22
<212> TYPE: PRT
<213> ORGANISM: Feline coronavirus

<400> SEQUENCE: 153

Met Ala Leu Gly Ser Ile Thr Ser Ala Val Ala Val Pro Phe Ala Met
1               5                   10                  15

Gln Val Gln Ala Arg Leu
            20

<210> SEQ ID NO 154
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 154 atg gct ttg ggt tct att aca tct gct gtg gct gtc cct ttc gca atg    48
Met Ala Leu Gly Ser Ile Thr Ser Ala Val Ala Val Pro Phe Ala Met
1               5                   10                  15 caa gtg cag gcg agg ctt                                            66
Gln Val Gln Ala Arg Leu
            20

<210> SEQ ID NO 155
<211> LENGTH: 22
<212> TYPE: PRT
<213> ORGANISM: Feline coronavirus

<400> SEQUENCE: 155

Met Ala Leu Gly Ser Ile Thr Ser Ala Val Ala Val Pro Phe Ala Met
1               5                   10                  15

Gln Val Gln Ala Arg Leu
            20

<210> SEQ ID NO 156
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 156

```
atg gcc ttg ggt tcc atc aca tct gct gtt gca gtt cct ttc gcc atg      48
Met Ala Leu Gly Ser Ile Thr Ser Ala Val Ala Val Pro Phe Ala Met
1               5                   10                  15 caa gtg cag gcg agg ctt                                               66
Gln Val Gln Ala Arg Leu
            20
```

<210> SEQ ID NO 157
<211> LENGTH: 22
<212> TYPE: PRT
<213> ORGANISM: Feline coronavirus

<400> SEQUENCE: 157

```
Met Ala Leu Gly Ser Ile Thr Ser Ala Val Ala Val Pro Phe Ala Met
1               5                   10                  15

Gln Val Gln Ala Arg Leu
            20
```

<210> SEQ ID NO 158
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 158

```
atg gcc ttg ggc tct att aca tcc gct gtg gct gtc cct ttt gct atg      48
Met Ala Leu Gly Ser Ile Thr Ser Ala Val Ala Val Pro Phe Ala Met
1               5                   10                  15 caa gtg cag gcg agg ctt                                               66
Gln Val Gln Ala Arg Leu
            20
```

<210> SEQ ID NO 159
<211> LENGTH: 22
<212> TYPE: PRT
<213> ORGANISM: Feline coronavirus

<400> SEQUENCE: 159

```
Met Ala Leu Gly Ser Ile Thr Ser Ala Val Ala Val Pro Phe Ala Met
1               5                   10                  15

Gln Val Gln Ala Arg Leu
            20
```

<210> SEQ ID NO 160
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 160

```
atg gct ttg ggt tct att act tct gct gtc gcc gtg cct ttc gca atg      48
```

```
Met Ala Leu Gly Ser Ile Thr Ser Ala Val Ala Val Pro Phe Ala Met
1               5                   10                  15 caa gtg cag gcg agg ctc                                           66
Gln Val Gln Ala Arg Leu
            20
```

<210> SEQ ID NO 161
<211> LENGTH: 22
<212> TYPE: PRT
<213> ORGANISM: Feline coronavirus

<400> SEQUENCE: 161

```
Met Ala Leu Gly Ser Ile Thr Ser Ala Val Ala Val Pro Phe Ala Met
1               5                   10                  15

Gln Val Gln Ala Arg Leu
            20
```

<210> SEQ ID NO 162
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 162

```
atg gcc ttg ggt tct att aca tct gct gtg gct gta cct ttc gcc atg   48
Met Ala Leu Gly Ser Ile Thr Ser Ala Val Ala Val Pro Phe Ala Met
1               5                   10                  15 caa gtg cag gcg agg ctt                                           66
Gln Val Gln Ala Arg Leu
            20
```

<210> SEQ ID NO 163
<211> LENGTH: 22
<212> TYPE: PRT
<213> ORGANISM: Feline coronavirus

<400> SEQUENCE: 163

```
Met Ala Leu Gly Ser Ile Thr Ser Ala Val Ala Val Pro Phe Ala Met
1               5                   10                  15

Gln Val Gln Ala Arg Leu
            20
```

<210> SEQ ID NO 164
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 164

```
atg gct ttg ggt tct att aca tct gct gta gct gtt cct ttt gcc atg   48
Met Ala Leu Gly Ser Ile Thr Ser Ala Val Ala Val Pro Phe Ala Met
1               5                   10                  15 caa gtg cag gcg agg ctt                                           66
Gln Val Gln Ala Arg Leu
            20
```

<210> SEQ ID NO 165
<211> LENGTH: 22
<212> TYPE: PRT
<213> ORGANISM: Feline coronavirus -continued

<400> SEQUENCE: 165

Met Ala Leu Gly Ser Ile Thr Ser Ala Val Ala Val Pro Phe Ala Met
1               5                   10                  15

Gln Val Gln Ala Arg Leu
            20

<210> SEQ ID NO 166
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 166 atg gct ttg ggc tct att aca tct gct gta gcc gtc cct ttt gct atg      48
Met Ala Leu Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 167
<211> LENGTH: 22
<212> TYPE: PRT
<213> ORGANISM: Feline coronavirus

<400> SEQUENCE: 167

Met Ala Leu Gly Ser Ile Thr Ser Ala Val Ala Val Pro Phe Ala Met
1               5                   10                  15

Gln Val Gln Ala Arg Leu
            20

<210> SEQ ID NO 168
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 168 atg gct ttg ggt tct att aca tca gct gta gct gtt ccc ttt gct atg      48
Met Ala Leu Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 169
<211> LENGTH: 22
<212> TYPE: PRT
<213> ORGANISM: Feline coronavirus

<400> SEQUENCE: 169

Met Ala Leu Gly Ser Ile Thr Ser Ala Val Ala Val Pro Phe Ala Met
1               5                   10                  15

Gln Val Gln Ala Arg Leu
            20

<210> SEQ ID NO 170
<211> LENGTH: 66
<212> TYPE: DNA
<213> ORGANISM: Feline coronavirus

```
<220> FEATURE:
<221> NAME/KEY: CDS
<222> LOCATION: (1)..(66)

<400> SEQUENCE: 170 atg gct ttg ggt tcc att acc tca gct gta gct gtt ccc ttt gct atg    48
Met Ala Leu Gly Ser Ile Thr Ser Ala Val Ala Val Pro Phe Ala Met
1               5                   10                  15 caa gta cag gct aga ctt                                            66
Gln Val Gln Ala Arg Leu
            20

<210> SEQ ID NO 171
<211> LENGTH: 22
<212> TYPE: PRT
<213> ORGANISM: Feline coronavirus

<400> SEQUENCE: 171

Met Ala Leu Gly Ser Ile Thr Ser Ala Val Ala Val Pro Phe Ala Met
1               5                   10                  15

Gln Val Gln Ala Arg Leu
            20

<210> SEQ ID NO 172
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 172 atg gcc ttg gga tct att aca tct gct gta gct gtt cct ttc gcg atg    48
Met Ala Leu Gly Ser Ile Thr Ser Ala Val Ala Val Pro Phe Ala Met
1               5                   10                  15 caa gtg cag gcc agg ctt                                            66
Gln Val Gln Ala Arg Leu
            20

<210> SEQ ID NO 173
<211> LENGTH: 22
<212> TYPE: PRT
<213> ORGANISM: Feline coronavirus

<400> SEQUENCE: 173

Met Ala Leu Gly Ser Ile Thr Ser Ala Val Ala Val Pro Phe Ala Met
1               5                   10                  15

Gln Val Gln Ala Arg Leu
            20

<210> SEQ ID NO 174
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 174 atg gct ttg ggc tct atc aca tct gct gtg gct gtc ccg ttt tct atg    48
Met Ala Leu Gly Ser Ile Thr Ser Ala Val Ala Val Pro Phe Ser Met
1               5                   10                  15 caa gtg cag gct agg ctt                                            66
Gln Val Gln Ala Arg Leu
            20
```

<210> SEQ ID NO 175
<211> LENGTH: 22
<212> TYPE: PRT
<213> ORGANISM: Feline coronavirus

<400> SEQUENCE: 175

Met Ala Leu Gly Ser Ile Thr Ser Ala Val Ala Val Pro Phe Ser Met
1               5                   10                  15

Gln Val Gln Ala Arg Leu
            20

<210> SEQ ID NO 176
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 176 atg gca ttg ggt tcc att acc tct gct gta gca gtt cct ttc gcc atg      48
Met Ala Leu Gly Ser Ile Thr Ser Ala Val Ala Val Pro Phe Ala Met
1               5                   10                  15 caa gtg cag gca agg ctt                                              66
Gln Val Gln Ala Arg Leu
            20

<210> SEQ ID NO 177
<211> LENGTH: 22
<212> TYPE: PRT
<213> ORGANISM: Feline coronavirus

<400> SEQUENCE: 177

Met Ala Leu Gly Ser Ile Thr Ser Ala Val Ala Val Pro Phe Ala Met
1               5                   10                  15

Gln Val Gln Ala Arg Leu
            20

<210> SEQ ID NO 178
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 178 atg gct ttg ggc tct att acg tct gca gtg gct gtc cct ttt gcc atg      48
Met Ala Leu Gly Ser Ile Thr Ser Ala Val Ala Val Pro Phe Ala Met
1               5                   10                  15 caa gta caa gct agg ctt                                              66
Gln Val Gln Ala Arg Leu
            20

<210> SEQ ID NO 179
<211> LENGTH: 22
<212> TYPE: PRT
<213> ORGANISM: Feline coronavirus

<400> SEQUENCE: 179

Met Ala Leu Gly Ser Ile Thr Ser Ala Val Ala Val Pro Phe Ala Met
1               5                   10                  15

Gln Val Gln Ala Arg Leu

<210> SEQ ID NO 180
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 180

```
atg gct ttg ggc tct att aca tct gct gta gca gtt cct ttc gcc atg    48
Met Ala Leu Gly Ser Ile Thr Ser Ala Val Ala Val Pro Phe Ala Met
1               5                   10                  15 caa gtg cag gcg agg ctt                                            66
Gln Val Gln Ala Arg Leu
            20
```

<210> SEQ ID NO 181
<211> LENGTH: 22
<212> TYPE: PRT
<213> ORGANISM: Feline coronavirus

<400> SEQUENCE: 181

```
Met Ala Leu Gly Ser Ile Thr Ser Ala Val Ala Val Pro Phe Ala Met
1               5                   10                  15

Gln Val Gln Ala Arg Leu
            20
```

<210> SEQ ID NO 182
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 182

```
atg gct ttg ggt tct att aca tct gct gta gct gtt cct ttt gcc atg    48
Met Ala Leu Gly Ser Ile Thr Ser Ala Val Ala Val Pro Phe Ala Met
1               5                   10                  15 caa gtg cag gcg agg ctt                                            66
Gln Val Gln Ala Arg Leu
            20
```

<210> SEQ ID NO 183
<211> LENGTH: 22
<212> TYPE: PRT
<213> ORGANISM: Feline coronavirus

<400> SEQUENCE: 183

```
Met Ala Leu Gly Ser Ile Thr Ser Ala Val Ala Val Pro Phe Ala Met
1               5                   10                  15

Gln Val Gln Ala Arg Leu
            20
```

<210> SEQ ID NO 184
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 184

```
atg gct ttg ggt tct att act tct gct gtg gca gtt ccc ttc gcc atg    48
Met Ala Leu Gly Ser Ile Thr Ser Ala Val Ala Val Pro Phe Ala Met
1               5                   10                  15 caa gtg caa gct agg ctt                                             66
Gln Val Gln Ala Arg Leu
            20

<210> SEQ ID NO 185
<211> LENGTH: 22
<212> TYPE: PRT
<213> ORGANISM: Feline coronavirus

<400> SEQUENCE: 185

Met Ala Leu Gly Ser Ile Thr Ser Ala Val Ala Val Pro Phe Ala Met
1               5                   10                  15

Gln Val Gln Ala Arg Leu
            20

<210> SEQ ID NO 186
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 186 atg gcc ttg gga tct att aca tct gct gta gct gtt cct ttc gcg atg    48
Met Ala Leu Gly Ser Ile Thr Ser Ala Val Ala Val Pro Phe Ala Met
1               5                   10                  15 caa gtg cag gcc agg ctt                                             66
Gln Val Gln Ala Arg Leu
            20

<210> SEQ ID NO 187
<211> LENGTH: 22
<212> TYPE: PRT
<213> ORGANISM: Feline coronavirus

<400> SEQUENCE: 187

Met Ala Leu Gly Ser Ile Thr Ser Ala Val Ala Val Pro Phe Ala Met
1               5                   10                  15

Gln Val Gln Ala Arg Leu
            20

<210> SEQ ID NO 188
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 188 atg gct ttg ggt tct att act tct gct gtc gcc gtg cct ttc gca atg    48
Met Ala Leu Gly Ser Ile Thr Ser Ala Val Ala Val Pro Phe Ala Met
1               5                   10                  15 caa gtg cag gcg agg ctt                                             66
Gln Val Gln Ala Arg Leu
            20

<210> SEQ ID NO 189
<211> LENGTH: 22
<212> TYPE: PRT
<213> ORGANISM: Feline coronavirus
```

<400> SEQUENCE: 189

Met Ala Leu Gly Ser Ile Thr Ser Ala Val Ala Val Pro Phe Ala Met
1               5                   10                  15

Gln Val Gln Ala Arg Leu
            20

<210> SEQ ID NO 190
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 190 atg gct ttg ggc tct atc aca tct gct gtg gct gtc ccg ttt tct atg      48
Met Ala Leu Gly Ser Ile Thr Ser Ala Val Ala Val Pro Phe Ser Met
1               5                   10                  15 caa gtg cag gct agg ctt                                              66
Gln Val Gln Ala Arg Leu
            20

<210> SEQ ID NO 191
<211> LENGTH: 22
<212> TYPE: PRT
<213> ORGANISM: Feline coronavirus

<400> SEQUENCE: 191

Met Ala Leu Gly Ser Ile Thr Ser Ala Val Ala Val Pro Phe Ser Met
1               5                   10                  15

Gln Val Gln Ala Arg Leu
            20

<210> SEQ ID NO 192
<211> LENGTH: 66
<212> TYPE: DNA
<213> ORGANISM: Feline coronavirus
<220> FEATURE:
<221> NAME/KEY: misc_feature
<222> LOCATION: (1)..(66)

<400> SEQUENCE: 192
atggccttgg gttctatcac atcagcggta gcagtaccct tctctatgca agtgcaggcg     60
aggctt                                                               66

<210> SEQ ID NO 193
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 193 atg gcc ttg ggt tct att aca tct gct gtg gct gta cct ttc gcc atg      48
Met Ala Leu Gly Ser Ile Thr Ser Ala Val Ala Val Pro Phe Ala Met
1               5                   10                  15 caa gtg cag gct agg ctt                                              66
Gln Val Gln Ala Arg Leu
            20

<210> SEQ ID NO 194
<211> LENGTH: 22

```
<212> TYPE: PRT
<213> ORGANISM: Feline coronavirus

<400> SEQUENCE: 194

Met Ala Leu Gly Ser Ile Thr Ser Ala Val Ala Val Pro Phe Ala Met
1               5                   10                  15

Gln Val Gln Ala Arg Leu
            20

<210> SEQ ID NO 195
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 195 acg gcc ttg ggt tct att aca tct gct gtg gct gta cct ttc gcc atg      48
Thr Ala Leu Gly Ser Ile Thr Ser Ala Val Ala Val Pro Phe Ala Met
1               5                   10                  15 caa gtg cag gct agg ctt                                              66
Gln Val Gln Ala Arg Leu
            20

<210> SEQ ID NO 196
<211> LENGTH: 22
<212> TYPE: PRT
<213> ORGANISM: Feline coronavirus

<400> SEQUENCE: 196

Thr Ala Leu Gly Ser Ile Thr Ser Ala Val Ala Val Pro Phe Ala Met
1               5                   10                  15

Gln Val Gln Ala Arg Leu
            20

<210> SEQ ID NO 197
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 197 atg gcc ttg ggt tct att aca tct gct gtg gcc gta cct ttc gcc atg      48
Met Ala Leu Gly Ser Ile Thr Ser Ala Val Ala Val Pro Phe Ala Met
1               5                   10                  15 caa gtg cag gct agg ctc                                              66
Gln Val Gln Ala Arg Leu
            20

<210> SEQ ID NO 198
<211> LENGTH: 22
<212> TYPE: PRT
<213> ORGANISM: Feline coronavirus

<400> SEQUENCE: 198

Met Ala Leu Gly Ser Ile Thr Ser Ala Val Ala Val Pro Phe Ala Met
1               5                   10                  15

Gln Val Gln Ala Arg Leu
            20

<210> SEQ ID NO 199
```

-continued

```
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 199 atg gcc ctg ggt tct att aca tct gct gtg gct gta cct ttt gct atg       48
Met Ala Leu Gly Ser Ile Thr Ser Ala Val Ala Val Pro Phe Ala Met
1               5                   10                  15 caa gtg cag gcc agg ctt                                                66
Gln Val Gln Ala Arg Leu
            20

<210> SEQ ID NO 200
<211> LENGTH: 22
<212> TYPE: PRT
<213> ORGANISM: Feline coronavirus

<400> SEQUENCE: 200

Met Ala Leu Gly Ser Ile Thr Ser Ala Val Ala Val Pro Phe Ala Met
1               5                   10                  15

Gln Val Gln Ala Arg Leu
            20

<210> SEQ ID NO 201
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 201 atg gct ttg ggc tct att aca tct gct gtg gca gtt ccc ttc gcc atg       48
Met Ala Leu Gly Ser Ile Thr Ser Ala Val Ala Val Pro Phe Ala Met
1               5                   10                  15 caa gtg cag gct agg ctt                                                66
Gln Val Gln Ala Arg Leu
            20

<210> SEQ ID NO 202
<211> LENGTH: 22
<212> TYPE: PRT
<213> ORGANISM: Feline coronavirus

<400> SEQUENCE: 202

Met Ala Leu Gly Ser Ile Thr Ser Ala Val Ala Val Pro Phe Ala Met
1               5                   10                  15

Gln Val Gln Ala Arg Leu
            20

<210> SEQ ID NO 203
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 203 atg gct ttg ggt tct att aca tcc gct gta gct gtg cct ttc gcc atg       48
Met Ala Leu Gly Ser Ile Thr Ser Ala Val Ala Val Pro Phe Ala Met
1               5                   10                  15
```

```
caa gtg cag gcg agg ctt                                                    66
Gln Val Gln Ala Arg Leu
        20

<210> SEQ ID NO 204
<211> LENGTH: 22
<212> TYPE: PRT
<213> ORGANISM: Feline coronavirus

<400> SEQUENCE: 204

Met Ala Leu Gly Ser Ile Thr Ser Ala Val Ala Val Pro Phe Ala Met
1               5                   10                  15

Gln Val Gln Ala Arg Leu
        20

<210> SEQ ID NO 205
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 205 atg gct ttg ggc tct att acg tct gca gtg gct gtc cct ttt gcc atg    48
Met Ala Leu Gly Ser Ile Thr Ser Ala Val Ala Val Pro Phe Ala Met
1               5                   10                  15 caa gta caa gct agg ctt                                                    66
Gln Val Gln Ala Arg Leu
        20

<210> SEQ ID NO 206
<211> LENGTH: 22
<212> TYPE: PRT
<213> ORGANISM: Feline coronavirus

<400> SEQUENCE: 206

Met Ala Leu Gly Ser Ile Thr Ser Ala Val Ala Val Pro Phe Ala Met
1               5                   10                  15

Gln Val Gln Ala Arg Leu
        20

<210> SEQ ID NO 207
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 207 atg gct atg ggt tct att aca tcc gct gta gca gtt cct ttt tcc atg    48
Met Ala Met Gly Ser Ile Thr Ser Ala Val Ala Val Pro Phe Ser Met
1               5                   10                  15 caa gtg cag gca cgt ctt                                                    66
Gln Val Gln Ala Arg Leu
        20

<210> SEQ ID NO 208
<211> LENGTH: 22
<212> TYPE: PRT
<213> ORGANISM: Feline coronavirus

<400> SEQUENCE: 208

Met Ala Met Gly Ser Ile Thr Ser Ala Val Ala Val Pro Phe Ser Met
```

```
1               5                   10                  15

Gln Val Gln Ala Arg Leu
            20

<210> SEQ ID NO 209
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 209 atg gct atg ggt tct att acc tca gct gta gct gtt ccc ttc gct atg      48
Met Ala Met Gly Ser Ile Thr Ser Ala Val Ala Val Pro Phe Ala Met
1               5                   10                  15 caa gta cag gct aga ctt                                              66
Gln Val Gln Ala Arg Leu
            20

<210> SEQ ID NO 210
<211> LENGTH: 22
<212> TYPE: PRT
<213> ORGANISM: Feline coronavirus

<400> SEQUENCE: 210

Met Ala Met Gly Ser Ile Thr Ser Ala Val Ala Val Pro Phe Ala Met
1               5                   10                  15

Gln Val Gln Ala Arg Leu
            20

<210> SEQ ID NO 211
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 211 atg gct atg ggt tct atc act tct gct gtg gct gtt cct ttc gcc atg      48
Met Ala Met Gly Ser Ile Thr Ser Ala Val Ala Val Pro Phe Ala Met
1               5                   10                  15 caa gtg caa gct agg ctt                                              66
Gln Val Gln Ala Arg Leu
            20

<210> SEQ ID NO 212
<211> LENGTH: 22
<212> TYPE: PRT
<213> ORGANISM: Feline coronavirus

<400> SEQUENCE: 212

Met Ala Met Gly Ser Ile Thr Ser Ala Val Ala Val Pro Phe Ala Met
1               5                   10                  15

Gln Val Gln Ala Arg Leu
            20

<210> SEQ ID NO 213
<211> LENGTH: 66
<212> TYPE: DNA
<213> ORGANISM: Feline coronavirus
<220> FEATURE:
<221> NAME/KEY: CDS
<222> LOCATION: (1)..(66)
```

<400> SEQUENCE: 213

```
atg gcc atg ggc tct att aca tct gct gta gcc gtc cct ttt gct atg    48
Met Ala Met Gly Ser Ile Thr Ser Ala Val Ala Val Pro Phe Ala Met
1               5                   10                  15 caa gtg caa gct agg ctt                                             66
Gln Val Gln Ala Arg Leu
            20
```

<210> SEQ ID NO 214
<211> LENGTH: 22
<212> TYPE: PRT
<213> ORGANISM: Feline coronavirus

<400> SEQUENCE: 214

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 215
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 215

```
atg gct atg ggt tct att aca tct gcc gta gct gtc cct ttt gct atg    48
Met Ala Met Gly Ser Ile Thr Ser Ala Val Ala Val Pro Phe Ala Met
1               5                   10                  15 caa gtg cag gct agg ctt                                             66
Gln Val Gln Ala Arg Leu
            20
```

<210> SEQ ID NO 216
<211> LENGTH: 22
<212> TYPE: PRT
<213> ORGANISM: Feline coronavirus

<400> SEQUENCE: 216

```
Met Ala Met Gly Ser Ile Thr Ser Ala Val Ala Val Pro Phe Ala Met
1               5                   10                  15

Gln Val Gln Ala Arg Leu
            20
```

<210> SEQ ID NO 217
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 217

```
atg gcc atg ggc tct att aca tct gct gtg gcc gtt cct ttc gcc atg    48
Met Ala Met Gly Ser Ile Thr Ser Ala Val Ala Val Pro Phe Ala Met
1               5                   10                  15 caa gtg cag gct agg ctt                                             66
Gln Val Gln Ala Arg Leu
            20
```

<210> SEQ ID NO 218

```
<211> LENGTH: 22
<212> TYPE: PRT
<213> ORGANISM: Feline coronavirus

<400> SEQUENCE: 218

Met Ala Met Gly Ser Ile Thr Ser Ala Val Ala Val Pro Phe Ala Met
1               5                   10                  15

Gln Val Gln Ala Arg Leu
            20

<210> SEQ ID NO 219
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 219 atg gct atg ggt tct att aca tcc gct gta gct gtg cct ttc gcc atg     48
Met Ala Met Gly Ser Ile Thr Ser Ala Val Ala Val Pro Phe Ala Met
1               5                   10                  15 caa gtg cag gcg agg ctt                                             66
Gln Val Gln Ala Arg Leu
            20

<210> SEQ ID NO 220
<211> LENGTH: 22
<212> TYPE: PRT
<213> ORGANISM: Feline coronavirus

<400> SEQUENCE: 220

Met Ala Met Gly Ser Ile Thr Ser Ala Val Ala Val Pro Phe Ala Met
1               5                   10                  15

Gln Val Gln Ala Arg Leu
            20

<210> SEQ ID NO 221
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 221 atg gct ttg ggt tct att acc tcc gct gta gca gtc ccc ttt tcc atg     48
Met Ala Leu Gly Ser Ile Thr Ser Ala Val Ala Val Pro Phe Ser Met
1               5                   10                  15 caa gtg cag gcg agg ctt                                             66
Gln Val Gln Ala Arg Leu
            20

<210> SEQ ID NO 222
<211> LENGTH: 22
<212> TYPE: PRT
<213> ORGANISM: Feline coronavirus

<400> SEQUENCE: 222

Met Ala Leu Gly Ser Ile Thr Ser Ala Val Ala Val Pro Phe Ser Met
1               5                   10                  15

Gln Val Gln Ala Arg Leu
            20
```

```
<210> SEQ ID NO 223
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 223 atg gct atg ggc tct att aca tct gct gtg gct gtc ccg ttc gcc atg      48
Met Ala Met Gly Ser Ile Thr Ser Ala Val Ala Val Pro Phe Ala Met
1               5                   10                  15 caa gtg caa gct agg ctt                                              66
Gln Val Gln Ala Arg Leu
            20

<210> SEQ ID NO 224
<211> LENGTH: 22
<212> TYPE: PRT
<213> ORGANISM: Feline coronavirus

<400> SEQUENCE: 224

Met Ala Met Gly Ser Ile Thr Ser Ala Val Ala Val Pro Phe Ala Met
1               5                   10                  15

Gln Val Gln Ala Arg Leu
            20

<210> SEQ ID NO 225
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 225 atg gct atg ggt tct atc act tct gct gtg gct gtt cct ttc gcc atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 226
<211> LENGTH: 22
<212> TYPE: PRT
<213> ORGANISM: Feline coronavirus

<400> SEQUENCE: 226

Met Ala Met Gly Ser Ile Thr Ser Ala Val Ala Val Pro Phe Ala Met
1               5                   10                  15

Gln Val Gln Ala Arg Leu
            20

<210> SEQ ID NO 227
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 227 atg gct ttg ggt tct att act tct gct gtc gcc gtg cct ttc gca atg      48
Met Ala Leu Gly Ser Ile Thr Ser Ala Val Ala Val Pro Phe Ala Met
1               5                   10                  15
```

```
caa gtg cag gcg agg ctt                                              66
Gln Val Gln Ala Arg Leu
        20

<210> SEQ ID NO 228
<211> LENGTH: 22
<212> TYPE: PRT
<213> ORGANISM: Feline coronavirus

<400> SEQUENCE: 228

Met Ala Leu Gly Ser Ile Thr Ser Ala Val Ala Val Pro Phe Ala Met
1               5                   10                  15

Gln Val Gln Ala Arg Leu
        20

<210> SEQ ID NO 229
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 229 atg gct atg ggt tct att aca tct gcc gta gct gtc cct ttt gct atg   48
Met Ala Met Gly Ser Ile Thr Ser Ala Val Ala Val Pro Phe Ala Met
1               5                   10                  15 caa gtg cag gct agg ctt                                              66
Gln Val Gln Ala Arg Leu
        20

<210> SEQ ID NO 230
<211> LENGTH: 22
<212> TYPE: PRT
<213> ORGANISM: Feline coronavirus

<400> SEQUENCE: 230

Met Ala Met Gly Ser Ile Thr Ser Ala Val Ala Val Pro Phe Ala Met
1               5                   10                  15

Gln Val Gln Ala Arg Leu
        20

<210> SEQ ID NO 231
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 231 atg gcc atg ggt tgt att aca tgt aga gtg act gta cct ttc gcc aag   48
Met Ala Met Gly Cys Ile Thr Cys Arg Val Thr Val Pro Phe Ala Lys
1               5                   10                  15 caa gtg cag gct agg gtt                                              66
Gln Val Gln Ala Arg Val
        20

<210> SEQ ID NO 232
<211> LENGTH: 22
<212> TYPE: PRT
<213> ORGANISM: Feline coronavirus

<400> SEQUENCE: 232
```

```
Met Ala Met Gly Cys Ile Thr Cys Arg Val Thr Val Pro Phe Ala Lys
1               5                   10                  15

Gln Val Gln Ala Arg Val
            20

<210> SEQ ID NO 233
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 233 atg gct atg ggt tct att acc tca gct gtt gcc gtg cct ttt gct atg    48
Met Ala Met Gly Ser Ile Thr Ser Ala Val Ala Val Pro Phe Ala Met
1               5                   10                  15 caa gtt cag gct aga ctt                                            66
Gln Val Gln Ala Arg Leu
            20

<210> SEQ ID NO 234
<211> LENGTH: 22
<212> TYPE: PRT
<213> ORGANISM: Feline coronavirus

<400> SEQUENCE: 234

Met Ala Met Gly Ser Ile Thr Ser Ala Val Ala Val Pro Phe Ala Met
1               5                   10                  15

Gln Val Gln Ala Arg Leu
            20

<210> SEQ ID NO 235
<211> LENGTH: 66
<212> TYPE: DNA
<213> ORGANISM: Feline coronavirus
<220> FEATURE:
<221> NAME/KEY: CDS
<222> LOCATION: (1)..(66)

<400> SEQUENCE: 235 atg gct atg ggc tct att acg tct gca gtg gct gtc cct ttt gcc atg    48
Met Ala Met Gly Ser Ile Thr Ser Ala Val Ala Val Pro Phe Ala Met
1               5                   10                  15 caa gta caa gct agg ctt                                            66
Gln Val Gln Ala Arg Leu
            20

<210> SEQ ID NO 236
<211> LENGTH: 22
<212> TYPE: PRT
<213> ORGANISM: Feline coronavirus

<400> SEQUENCE: 236

Met Ala Met Gly Ser Ile Thr Ser Ala Val Ala Val Pro Phe Ala Met
1               5                   10                  15

Gln Val Gln Ala Arg Leu
            20

<210> SEQ ID NO 237
<211> LENGTH: 66
<212> TYPE: DNA
<213> ORGANISM: Feline coronavirus
<220> FEATURE:
<221> NAME/KEY: CDS
```

-continued

```
<222> LOCATION: (1)..(66)

<400> SEQUENCE: 237 atg gct atg ggt tct att aca tct gct gta gct gtt cct ttt gct atg      48
Met Ala Met Gly Ser Ile Thr Ser Ala Val Ala Val Pro Phe Ala Met
1               5                   10                  15 caa gtg cag gcg agg ctt                                              66
Gln Val Gln Ala Arg Leu
            20

<210> SEQ ID NO 238
<211> LENGTH: 22
<212> TYPE: PRT
<213> ORGANISM: Feline coronavirus

<400> SEQUENCE: 238

Met Ala Met Gly Ser Ile Thr Ser Ala Val Ala Val Pro Phe Ala Met
1               5                   10                  15

Gln Val Gln Ala Arg Leu
            20
```

The invention claimed is:

1. A method comprising testing whether a sample from a feline comprises a serotype I feline coronavirus and, if a serotype I feline coronavirus is present, testing which amino acid is present in a spike protein of said serotype I feline coronavirus at a position corresponding to amino acid position 1049 as depicted in FIG. 2B (SEQ ID NO:8), and euthanizing the feline or immunizing the feline against serotype I feline infectious peritonitis virus (FIPV) if said amino acid is not methionine.

2. The method according to claim 1, wherein testing which amino acid is present at position 1049 comprises testing which nucleotide is present at, or corresponding to, position 3145, 3146 and/or 3147 as depicted in FIG. 2A (SEQ ID NO:6) of a feline coronavirus nucleic acid encoding said spike protein.

3. The method according to claim 1 or 2, wherein said amino acid other than methionine is leucine.

4. The method according to claim 2, further comprising amplifying at least part of a feline coronavirus nucleic acid molecule comprising a region including, or corresponding to, nucleotide position 3145, 3146 and 3147 as depicted in FIG. 2A (SEQ ID NO:6) using at least one primer which is capable of hybridizing to at least part of said nucleic acid sequence between a position corresponding to nucleotide position 3055 and a position corresponding to nucleotide position 3669 as depicted in FIG. 2A (SEQ ID NO:6).

5. A method comprising testing whether a sample from a feline comprises a serotype I feline coronavirus and, if a serotype I feline coronavirus is present, testing which amino acid is present in a spike protein of said serotype I feline coronavirus at a position corresponding to amino acid position 1051 as depicted in FIG. 2B (SEQ ID NO:8), and euthanizing the feline or immunizing the feline against serotype I feline infectious peritonitis virus (FIPV) if said amino acid is not serine.

6. The method according to claim 1, further comprising testing which amino acid is present in a spike protein of said feline coronavirus at a position corresponding to amino acid position 1051 as depicted in FIG. 2B (SEQ ID NO:8), and determining that FIPV is present if said amino acid is not serine.

7. The method according to claim 5, wherein testing which amino acid is present at position 1051 comprises testing which nucleotide is present at, or corresponding to, position 3151, 3152 and/or 3153 as depicted in FIG. 2A (SEQ ID NO:6) of a feline coronavirus nucleic acid encoding said spike protein.

8. The method according to claim 5, wherein said amino acid other than serine is alanine.

9. The method according to claim 7, further comprising amplifying at least part of a feline coronavirus nucleic acid molecule comprising a region including, or corresponding to, nucleotide position 3151, 3152 and 3153 as depicted in FIG. 2A (SEQ ID NO:6) using at least one primer which is capable of hybridizing to at least part of said nucleic acid sequence between a position corresponding to nucleotide position 3055 and a position corresponding to nucleotide position 3669 as depicted in FIG. 2A (SEQ ID NO:6).

10. A method for determining whether feline infectious peritonitis virus (FIPV) is present in a sample, comprising testing whether said sample comprises a feline coronavirus, and if a feline coronavirus is present testing which amino acid is present in a spike protein of said feline coronavirus at a position corresponding to amino acid position 1051 as depicted in FIG. 2B (SEQ ID NO:8), and determining that FIPV is present if said amino acid is not serine, wherein testing which amino acid is present at position 1051 comprises testing which nucleotide is present at, or corresponding to position 3151, 3152 and/or 3153 as depicted in FIG. 2A (SEQ ID NO:6) of a feline coronavirus nucleic acid encoding said spike protein, wherein testing which nucleotide is present at, or corresponding to, position 3151, 3152 and/or 3153 as depicted in FIG. 2A (SEQ ID NO:6) further comprises amplifying at least part of a feline coronavirus nucleic acid molecule comprising a region including, or corresponding to, nucleotide position 3151, 3152 and 3153 as depicted in FIG. 2A (SEQ ID NO:6) using at least one primer which is capable of hybridizing to at least part of said nucleic acid sequence between a position corresponding to nucleotide position 3055 and a position corresponding to nucleotide position 3669 as depicted in FIG. 2A (SEQ ID NO:6), wherein said at least one primer is selected from the group consisting of SEQ ID NO: 1, SEQ ID NO: 2, SEQ ID NO: 3, and SEQ ID NO: 4.

11. The method according to claim 2, wherein said nucleotide is detected using a probe with a length of at least 14 nucleotides that is capable of specifically hybridizing to at least part of a feline coronavirus nucleic acid comprising a nucleotide at, or corresponding to, position 3145, 3146 and 3147 as depicted in FIG. 2A (SEQ ID NO:6), said part having a length of at least 14 nucleotides.

12. A probe with a length of between 14 and 100 nucleotides, comprising a nucleic acid sequence which has at least 90% sequence identity with the sequence 5'-CCCARRGC-CATAGG-3'(SEQ ID NO:5), attached to a label.

13. The method according to claim 11, further comprising sequencing at least part of a feline coronavirus nucleic acid sequence, said part comprising a nucleotide corresponding to nucleotide position 3145, 3146 and/or 3147 as depicted in FIG. 2A (SEQ ID NO:6).

14. The method according to claim 6, wherein said amino acid other than serine is alanine.

15. A method for determining whether feline infectious peritonitis virus (FIPV) is present in a sample, comprising testing whether said sample comprises a feline coronavirus, and if a feline coronavirus is present testing which amino acid is present in a spike protein of said feline coronavirus at a position corresponding to amino acid position 1049 as depicted in FIG. 2B (SEQ ID NO:8), and determining that FIPV is present if said amino acid is not methionine, wherein testing which amino acid is present at position 1049 comprises testing which nucleotide is present at, or corresponding to, position 3145, 3146 and/or 3147 as depicted in FIG. 2A (SEQ ID NO:6) of a feline coronavirus nucleic acid encoding said spike protein, wherein testing which nucleotide is present at, or corresponding to, position 3145, 3146 and/or 3147 as depicted in FIG. 2A (SEQ ID NO:6) further comprises amplifying at least part of a feline coronavirus nucleic acid molecule comprising a region including, or corresponding to, nucleotide position 3145, 3146 and 3147 as depicted in FIG. 2A (SEQ ID NO:6) using at least one primer which is capable of hybridizing to at least part of said nucleic acid sequence between a position corresponding to nucleotide position 3055 and a position corresponding to nucleotide position 3669 as depicted in FIG. 2A (SEQ ID NO:6), wherein said at least one primer is selected from the group consisting of SEQ ID NO: 1, SEQ ID NO: 2, SEQ ID NO: 3, and SEQ ID NO: 4.

16. The method according to claim 7, wherein said nucleotide is detected using a probe with a length of at least 14 nucleotides that is capable of specifically hybridizing to at least part of a feline coronavirus nucleic acid comprising a nucleotide at, or corresponding to, position 3151, 3152 and 3153 as depicted in FIG. 2A (SEQ ID NO:6), said part having a length of at least 14 nucleotides.

17. The method according to claim 2, further comprising sequencing at least part of a feline coronavirus nucleic acid sequence, said part comprising a nucleotide corresponding to nucleotide position 3145, 3146 and/or 3147 as depicted in FIG. 2A (SEQ ID NO:6).

18. The method according to claim 4, further comprising sequencing at least part of a feline coronavirus nucleic acid sequence, said part comprising a nucleotide corresponding to nucleotide position 3145, 3146 and/or 3147 as depicted in FIG. 2A (SEQ ID NO:6).

19. The method according to claim 7, further comprising sequencing at least part of a feline coronavirus nucleic acid sequence, said part comprising a nucleotide corresponding to nucleotide position 3151, 3152 and/or 3153 as depicted in FIG. 2A (SEQ ID NO:6).

20. The method according to claim 9, further comprising sequencing at least part of a feline coronavirus nucleic acid sequence, said part comprising a nucleotide corresponding to nucleotide position 3151, 3152 and/or 3153 as depicted in FIG. 2A (SEQ ID NO:6).

21. The method according to claim 16, further comprising sequencing at least part of a feline coronavirus nucleic acid sequence, said part comprising a nucleotide corresponding to nucleotide position 3151, 3152 and/or 3153 as depicted in FIG. 2A (SEQ ID NO:6).

22. A method for determining the identity of an amino acid in a spike protein of a serotype I feline coronavirus at a position corresponding to amino acid position 1049 as depicted in FIG. 2B (SEQ ID NO:8), the method comprising testing in a sample from a feline having a symptom selected from the group consisting of accumulation of ascetic fluid within the abdomen, retarded growth, lack of appetite, fever, weight loss, diarrhea and combinations thereof whether said sample comprises a serotype I feline coronavirus and, if a serotype I feline coronavirus is present, testing which amino acid is present at said position corresponding to amino acid position 1049 as depicted in FIG. 2B (SEQ ID NO:8).

23. The method according to claim 22, comprising testing whether leucine is present at said position corresponding to amino acid position 1049.

24. A method for treating a feline suffering from feline enteric coronavirus (FECV), the method comprising testing whether a sample from said feline comprises a serotype I feline coronavirus and, if a serotype I feline coronavirus is present, testing which amino acid is present in a spike protein of said feline coronavirus at a position corresponding to amino acid position 1049 as depicted in FIG. 2B (SEQ ID NO:8), and providing the feline with treatment against FECV if said amino acid is methionine.

25. The method according to claim 5, for preventing spread of serotype I feline infectious peritonitis virus (FIPV), the method comprising testing whether a sample from a feline comprises a serotype I feline coronavirus and, if a serotype I feline coronavirus is present, testing which amino acid is present in a spike protein of said feline coronavirus at a position corresponding to amino acid position 1051 as depicted in FIG. 2B (SEQ ID NO:8), and euthanizing the feline if said amino acid is not serine in order to prevent spread of FIPV.

26. A method for treating a feline suffering from feline enteric coronavirus (FECV), the method comprising testing whether a sample from said feline comprises a serotype I feline coronavirus and, if a serotype I feline coronavirus is present, testing which amino acid is present in a spike protein of said feline coronavirus at a position corresponding to amino acid position 1051 as depicted in FIG. 2B (SEQ ID NO:8), and providing the feline with treatment against FECV if said amino acid is serine.

27. The probe according to claim 12, wherein the label is a fluorophore, a chromophore, an enzyme, a radio-label, streptavidin, biotin, or digoxigenin.

28. A method for determining the identity of an amino acid in a spike protein of serotype I feline coronavirus at a position corresponding to amino acid position 1051 as depicted in FIG. 2B (SEQ ID NO:8), the method comprising testing in a sample from a feline having a symptom selected from the group consisting of accumulation of ascetic fluid within the abdomen, retarded growth, lack of appetite, fever, weight loss, diarrhea and combinations thereof whether said sample comprises a serotype I feline coronavirus and, if a serotype I feline coronavirus is present, testing which amino acid is present at said position corresponding to amino acid position 1051 as depicted in FIG. 2B (SEQ ID NO:8).

29. The method according to claim 28, comprising testing whether alanine is present at said position corresponding to an amino acid position 1051.

30. The method according to claim 28, further comprising, if a serotype I feline coronavirus is present, testing which amino acid is present at a position corresponding to amino acid position 1049 as depicted in FIG. 2B (SEQ ID NO:8).

31. The method according to claim 22, wherein testing which amino acid is present at position 1049 comprises testing which nucleotide is present at, or corresponding to, position 3145, 3146 and/or 3147 as depicted in FIG. 2A (SEQ ID NO:6) of a feline coronavirus nucleic acid encoding said spike protein.

32. The method according to claim 28, wherein testing which amino acid is present at position 1051 comprises testing which nucleotide is present at, or corresponding to, position 3151, 3152 and/or 3153 as depicted in FIG. 2A (SEQ ID NO:6) of a feline coronavirus nucleic acid encoding said spike protein.

\* \* \* \* \*